US008901084B2

(12) United States Patent  (10) Patent No.: US 8,901,084 B2
Genove et al.  (45) Date of Patent: *Dec. 2, 2014

(54) SELF-ASSEMBLING PEPTIDE INCORPORATING MODIFICATIONS AND METHODS OF USE THEREOF

(75) Inventors: Elsa Genove, Barcelona (ES);
Shuguang Zhang, Lexington, MA (US);
Carlos Semino, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/724,153

(22) Filed: Mar. 15, 2010

(65) Prior Publication Data

US 2010/0311640 A1 Dec. 9, 2010

Related U.S. Application Data

(63) Continuation of application No. 10/877,068, filed on Jun. 25, 2004, now Pat. No. 7,713,923, which is a continuation-in-part of application No. 10/877,827, filed on Jun. 24, 2004, now abandoned.

(60) Provisional application No. 60/482,261, filed on Jun. 25, 2003.

(51) Int. Cl.
*A61K 38/00* (2006.01)
*C07K 14/78* (2006.01)

(52) U.S. Cl.
CPC .............. *C07K 14/78* (2013.01); *A61K 38/00* (2013.01); *C07K 2319/735* (2013.01)
USPC ........................................................ 514/21.3

(58) Field of Classification Search
None
See application file for complete search history.

(56) References Cited

U.S. PATENT DOCUMENTS

| 6,489,116 B2 | 12/2002 | Wagner et al. |
| 7,449,180 B2 | 11/2008 | Kisiday et al. |

FOREIGN PATENT DOCUMENTS

| WO | 02062969 A2 | 8/2002 |
| WO | 03/046560 A2 | 6/2003 |
| WO | WO 03/070749 | 8/2003 |

OTHER PUBLICATIONS

Beck, et al., "Structure and Function of Laminin: Anatomy of a Multidomain Glycoprotein", *FASEB J.* 4, 148-160, 1990.
Bell, et al., "Differential Gene Expression During Capillary Morphogenesis in 3D Collagen Matrices: Regulated Expression of Genes Involved in Basement Membrane Matrix Assembly, Cell Cycle Progression, Cellular Differentiation and G-Protein Signaling", *J. Cell Science*, 114: 2755-2773, 2001.
Binning, et al., "Atomic Force Microscope" *Phys. Rev. Lett.*, 12, 930-933, 1986.
Brown, S. "Metal Recognition by Repeating Polypeptides", *Nat. Biotechnol.*, 15:269-92, 1997.
Busse, et al., "Regulation of Endothelium-Derived Vasoactive Autacoid Production by Hemodynamic Forces", *Trends in Pharmacological Sciences*, 24: 24-29, 2003.
Caplan, et al., "Self-Assembly of a Beta-Sheet Oligopeptide is Governed by Electrostatic Repulsion", *Biomacromolecules*, 1, 627-631, 2000.
Caplan, et al., "Control of Self-Assembling Oligopeptide Matrix Formation through Systematic Variation of Amino Acid Sequence," *Biomaterials*, 23, 219-227, 2002.
Caplan, et al., "Effects of Systematic Variation of Aminoacid Sequence on the Mechanical Properties of a Self-Assembling, Oligopeptide Biomaterial", *J. Biomater. Sci. Polymer Edition*, 13, 225-236, 2002.
Carmeliet, P., "Mechanisms of Angiogenesis and Arteriogenesis", *Nat.Med.*, 6: 389-395, 2000.
Cassell, et al., "Vascularization of Tissue-Engineered Grafts: The Regulation of Angiogenesis in Reconstructive Surgery and in Disease States", *Br. J. Plast. Surg.*, 55: 603-610, 2002.
Charonis, et al., "Binding of Laminin to Type IV Collagen: a Morphological Study" *J. Cell Biol.* 100, 1848-1853, 1985.
Cines, et al., "Endothelial Cells in Physiology and Pathophysiology of Vascular Disorders", *Blood*, 91, 3527-3561, 1998.
Colton, C., "Implantable Biohybrid Artificial Organs", *Cell Transplantation*, 4: 415-436, 1995.
Davis, et al., "Capillary Morphogenesis During Human Endothelial Cell Invasion of Three-Dimensional Collagen Matrices", *In Vitro Cell. Dev. Biol. Animal*, 36: 513-519, 2000.
Davis, et al., "Molecular Basis of Endothelial Cell Morphogenesis in Three-Dimensional Extracellular Matrices", *Anat. Rec.*, 268: 252-275, 2002.
Dorsett, et al., "siRNAs: Applications in Functional Genomics and Potential as Therapeutics", *Nat. Rev. Drug Discovery*, 3: 318-329, 2004.
Dziadek, et al., "Expression of Nidogen and Laminin in Basement Membranes During Mouse Embryogenesis and in Teratocarcinoma Cells" *Dev. Biol.* 111, 372-382, 1985.

(Continued)

*Primary Examiner* — Christina Bradley
(74) *Attorney, Agent, or Firm* — Carolyn S. Elmore; Elmore Patent Law Group, P.C.

(57) ABSTRACT

The invention provides a self-assembling peptide comprising (a) a first amino acid domain that mediates self-assembly, wherein the domain comprises alternating hydrophobic and hydrophilic amino acids that are complementary and structurally compatible and self-assemble into a macroscopic structure when present in unmodified form; and (b) a second amino acid domain that does not self-assemble in isolated form. In certain embodiments of the invention the second amino acid domain comprises a biologically active peptide motif, e.g., a peptide motif found in a naturally occurring protein, or a target site for an interaction with a biomolecule. In certain embodiments of the invention the naturally occurring protein is a component of the extracellular matrix, e.g., a component of the basement membrane. The invention further provides scaffolds comprising the self-assembling peptides and methods of using the scaffolds including for cell culture, tissue engineering, and tissue repair.

30 Claims, 29 Drawing Sheets

(56) References Cited

OTHER PUBLICATIONS

Eiselt, et al., "Development of Technologies Aiding Large Tissue Engineering", *Biotechnol. Prog.*, 14: 134-140, 1998.
Engel, J., et al., "Shapes, Domain Organizations and Flexibility of Laminin and Fibronectin, Two Multifunctional Proteins of the Extracellular Matrix", *J. Mol. Biol.* 150, 97-120, 1981.
Engel, J. "Laminins and Other Strange Proteins," *Biochemistry*, 31, 10643-10651, 1992.
Fujiwara, et al., "Structure and Interaction of Heparan Sulfate Proteoglycans from a Mouse Tumor Basement Membrane", *Eur. J. Biochem.* 143, 145-157, 1984.
Gloe, et al., "The 67-kDa Laminin-Binding Protein is Involved in Shear Stress-Dependent Endothelial Nitric-Oxide Synthase Expression", *J. Biol. Chem.*, 274: 15996-16002, 1999.
Graf, J., et al., "Identification of an Amino Acid Sequence in Laminin Mediating Cell Attachment, Chemotaxis and Receptor Binding", *Cell* 48, 989-996, 1987.
Grant, et al., "Interaction of Endothelial Cells with a Laminin A Chain Peptide (SIKVAV) in Itro and Induction of Angiogenic Behavior in Vivo", *J. Cell. Physiol.*, 153, 614-25, 1992.
Grant, et al., "Two Different Laminin Domains Mediate the Differentiation of Human Endothelial Cells into Capillary-Like Structures in Vitro", *Cell*, 58, 933-43, 1989.
Han, et al., "Angiogenesis State of the Art" *Int J Hematol*; 70(2):68-82, 1999.
Hartgerink, et al., "Self-Assembly and Mineralization of Peptide-Amphiphile Nanofibers" *Science*; 294: 1684-1688, 2001.
Holmes, et al., "Extensive Neurite Outgrouth and Active Synapse Formation on Self-Assembling Peptide Scaffolds", *PNAS*, 97, 6728-6733, 2000.
Iwamoto, et al., "A Synthetic Laminin Pentapeptide, Inhibits Experimental Metastasis Formation", *Science* 238, 1132-1134, 1987.
Kanemoto, et al., "Identification of an Aminoacid Sequence from the Laminin A Chain that Stimulates Metastasis and Collagenase IV Production", *Proc. Natl. Acad. Sci., USA*, 87, 2279-2283, 1990.
Kavanagh, et al., "Rheological Characterization of Polymer Gels", *Prog. Polym. Sci.*, 23, 533-562, 1998.
Kisiday, et al., "Self-Assembling Peptide Hydrogel Fosters Chondrocyte Extracellular Matrix Production and Cell Division: Implications for Cartilage Tissue Repair", *Proc. Natl. Acad. Sci. USA*, 99: 9996-10001, 2002.
Kisiday, et al., "Effects of Dynamic Compressive Loading on Chondrocyte Biosynthesis in Self-Assembling Peptide Scaffolds", *J. Biomech*, 37(5): 595-604, 2004.
Klein, et al., "Differential Expression of Laminin A and B Chains During Development of Embryonic Mouse Organs", *Development* 110, 823-837, 1990.
Kleinman, et al., "Identification of a Second Active Site in Laminin for Promotion of Cell Adhesion and Migration and Inhibition of Melanoma Lung Colonization", *Arch. Biochem. Biophys.* 272, 39-45, 1989.
Koliakos, et al., "The Binding of Heparin to Type IV Collagen: Domain Specificity with Identification of Peptide Sequences from the Alpha 1(IV) and Alpha 2(IV) Which Preferentially Bind Heparin" *J. Biol. Chem.* 264, 2313-2323, 1989.
Kubota, et al., "Role of Laminin and Basement Membrane in the Morphological Differentiation of Human Endothelial Cells into Capillary-like Structures", *J. Cell. Biol.*, 107, 1589-1598, 1988.
Lendahl, et al., "CNS Stem Cells Express a New Class of Intermediate Filament Protein", *Cell*, 60:585-595, 1990.
Leon, et al., "Mechanical Properties of a Self-Assembling Oligopeptide Matrix", *J. Biomater. Sci. Polymer Edition*, 9, 297-312, 1998.
Lin, et al., "Synthesis, Surface, and Cell-Adhesion Properties of Polyurethanes Containing Covalently Grafted RGD-Peptides", *J. Biomed. Mater. Res.* 3: 329-342, 1994.
Malinda, et al., "Identification of Laminin $\alpha 1$ and $\beta 1$ Chain Peptides Active for Endothelial Cell Adhesion, Tube Formation and Aortic Sprouting", *FASEB*, 13, 53-62, 1999.

Mann, et al., "Cell Adhesion Peptides Alter Smooth Muscle Cell Adhesion, Proliferation, Migration, and Matrix Protein Synthesis on Modified Surfaces and in Polymer Scaffolds", *Biomed. Mater. Res.* 60(1):86-93, 2002.
Martin, et al., "Laminin and Other Basement Membrane Components", *Annu. Rev. Cell. Biol.* 3, 57-85, 1987.
Massia, et al., "Human Endothelial Cell Interactions with Surface-Coupled Adhesion Peptides on Non-Adhesive Glass and Two Polymeric Biomaterials", *J. Biomed. Mater. Res.* 2: 223-242, 1991.
Nomizu, et al., "Identification of Homologous Biologically Active Sites on the N-Terminal Domain of Laminin Alpha Chains", *Biochemistry*, 40, 15310-17, 2001.
Nomizu, et al., "The All-D-Configuration Segment Containing the IKVAV Sequence of Laminin A Chain has Similar Activities to the All-L-Peptide in Vitro and in Vivo", *J. Biol. Chem.* 267, 14118-14121, 1992.
Nomizu, et al., "Identification of Cell Binding Sequences in Mouse Laminin a1 Chain by Systematic Peptide Screening", *J. Biol. Chem.* 272, 32198-32205, 1997.
Paulsson, et al., "Laminin-Nidogen Complex. Extraction with Chelating Agents and Structural Characterization", *Eur. J. Biochem.* 166, 11-19, 1987.
Ponce, et al., "Identification of Endothelial Cell Binding Sites on the Laminin γ1 Chain", *Circ. Res.*, 84, 688-694, 1999.
Poschl, et al., "Site-Directed Mutagenesis and Structural Interpretation of the Nidogen Binding Site of the Laminin Gamma 1 Chain", *EMBO J.* 15, 5154-5159, 1996.
Sagnella, et al., "Human Microvascular Endothelial Cell Growth and Migration on Biomimetic Surfactant Polymers", *Biomaterials*, 25: 1249-1259, 2004.
Sakamoto, et al.. "Inhibition of Angiogenesis and Tumor Growth by a Synthetic Laminin Peptide, CDPGYIGSR-$NH_2$",*Cancer Res*, 51, 903-6, 1991.
Sarikaya, et al., Materials Assembly and Formation Using Engineered Polypeptides, *Annu. Rev. Mater. Res.* 34:373-408. Published online Apr. 2, 2004.
Sarnat, ., et al., "Neuronal Nuclear Antigen (NeuN): a Marker of Neuronal Maturation in Early Human Fetal Nervous System", *Brain Research*, 20:88-94, 1998.
Schmedlen, et al.. "Photocrosslinkable Polyvinyl Alcohol Hydrogels that Can be Modified with Cell Adhesion Peptides for Use in Tissue Engineering", *Biomaterials*; 23: 4325-4332, 2002.
Semino, et al., "Functional Differentiation of Hepatocyte-Like Spheroid Structures from Putative Liver Progenitor Cells in Three-Dimensional Peptide Scaffolds", *Differentiation*, 71: 262-270, 2003.
Semino, et al., "Entrapment of Migrating Hippocampal Neural Cells in 3-D Peptide Nanfiber Scaffold", *Tissue Engineering*, 10(3-4): 643-655, 2004.
Skubitz, et al., "Definition of a Sequence, RYVVLPR, within Laminin Peptide F-9 that Mediates Metastatic Fibrosarcoma Cell Adhesion and Spreading", *Cancer Res.*, 50, 7612-22, 1990.
Stack, et al.., "Modulation of Plasminogen Activation and Type IV Collagenase Activity by a Synthetic Peptide Derived from the Laminin A chain", *Biochemistry*, 30, 2073-2077, 1990.
Tashiro, et al., "A Synthetic Peptide Containing the IKVAV Sequence from the A Chain of Laminin Mediates Cell Attachment, Migration, and Neurite Outgrowth",. *J. Biol. Chem.*, 264, 16174-16182, 1989.
Timpl, R. "Structure and Biological Activity of Basement Membrane Proteins", *Eur. J. Biochem.* 180, 487-502., 1989.
Timpl, R. "Macromolecular Organization of Basement Membranes" *Curr. Opin. Cell Biol.* 8, 618-624, 1996.
Tsilibary, et al., "Identification of a Multifunctional, Cell-Binding Peptide Sequence from the a1(NC1) of Type IV Collagen", *J. Cell Biol.* 111, 1583-1591, 1990.
Tsilibary, et al.,. "Heparin Type IV Collagen Interactions: Equilibrium Binding and Inhibition of Type IV Collagen Self-Assembly", *J. Biol. Chem.* 263, 19112-19118, 1988.
Whaley, et al.,. "Selection of Peptides with Semiconductor Binding Specificity for Directed Nanocrystal Assembly", *Nature*, 405(6787):665-8, 2000.
Whitesides, et al., "Molecular Self-Assembly and Nanochemistry: a Chemical Strategy for the Synthesis of Nanostructures" *Science*, 254, 1312, 1991.

(56) References Cited

OTHER PUBLICATIONS

Yamada, K.M. "Adhesive Recognition Sequences", *J. Biol. Chem.* 266, 12809-12812, 1991.

Yamada, et al., "Functional Domains of Cell Adhesion Molecules", *Curr. Opin. Cell. Biol.* 4, 819-823, 1992.

Yurchenco, et al., "Self-Assembly and Calcium-Binding Sites in Laminin. A three-arm interaction model", *J. Biol. Chem.* 268, 17286-17299, 1993.

Zhang, et al., "Zuotin, A Putative Z-DNA Binding Protein in *Saccharomyces cervsiae*", *EMBO, J.*, 11: 3787-3796, 1992.

Zhang, et al., "Peptide Self-Assembly in Functional Polymer Science and Engineering", *Reactive & Functional Polymers*, 41: 91-102, 1999.

Zhang, et al., "Spontaneous Assembly of a Self-Complementary Oligopeptide to Form a Stable Macroscopic Membrane", *Proc. Natl. Acad. Sci. USA*, 90: 3334-3338, 1993.

Zhang, et al., "Self-Complementary Oligopeptide Matrices Support Mammalian Cells Attachment", *Biomaterials*, 16: 1385-1393, 1995.

Barlow et al. "Sequencing of laminin B chain cDNAs reveals C-terminal regions of coiled-coil alpha-helix," EMBO J., 3, 2235-62, 1984.

Massia et al. "Covalently Immobilized Laminin Peptide Tyr-Ile-Gly-Ser-Arg (YIGSR) Supports Cell Spreading and Co-locatization of the 67-Kilodalton Laminin Receptor with alpha-Actinin and Vinculin," J. Biol. Chem., 268, 8053-9, 1993.

Neal et al. "Laminin Nanofiber Meshes That Mimic Morphological Properties and Bioactivity of Basement Membranes," Tissue Engineering, 14, 1-11, 2008.

Nomizu et al. "Cell adhesive sequences in mouse laminin $\beta1$ chain," Archives of Biochemistry and Biophysics, 378, 2, 311-20, 2000.

Zhang, "Emerging biological materials through molecular self-assembly," Biotechnology Advances, vol. 20, 321-339, 2002.

International Search Report for International Application Serial No. PCT/US04/020549.

Written Opinion of the International Searching Authority for International Application Serial No. PCT/US/020549.

SELF-ASSEMBLING PEPTIDE INCORPORATING MODIFICATIONS AND METHODS OF USE THEREOF

CROSS-REFERENCE TO RELATED APPLICATION

This application is a continuation of U.S. patent application 10/877,068, filed on Jun. 25, 2004, which is continuation-in-part of an application entitled "Self-Assembling Peptides Incorporating Modifications and Methods of Use Thereof", filed Jun. 24, 2004, listing Elsa Genove, Carlos Semino, and Shuguang Zhang as inventors, (Express Mail Label No. EV416226294US, U.S. Ser. No. 10/877,827), each of which claim priority to U.S. Provisional Patent Application Ser. No. 60/482,261, filed Jun. 25, 2003 and all of which are herein incorporated by reference.

GOVERNMENT SUPPORT

This invention was made with Government support under Grant No.F49620-02-1-0333, awarded by the US Air Force and under Grant No. EEC9843342, awarded by the National Science Foundation. The Government has certain rights in this invention.

BACKGROUND OF THE INVENTION

The extracellular matrix (ECM) is composed of a diverse set of macromolecules, including both proteins and polysaccharides, which form the three-dimensional environment within which cells exist in the body and constitute the space-filling material between cells. The ECM can also be organized into a sheetlike layer known as the basal lamina or basement membrane. In many regions of the body, the basement membrane lies beneath layers or tubes of epithelial cells (e.g., endothelial cells lining blood vessels) or surrounds individual cells of various types such as muscle cells, often serving to separate cell layers from one another or from adjacent connective tissue.

The ECM consists primarily of molecules that are secreted locally and assemble into a scaffold that stabilizes and supports the physical structure of cell layers and tissues. However, rather than being merely an inert substrate for cell attachment, the ECM constitutes an environment that is rich in biological information. It is recognized that the ECM, and various biomolecules associated with it (e.g., secreted locally or transported to a particular site from elsewhere), exert a significant influence on many aspects of cell behavior and phenotype, regulating processes such as migration and proliferation, influencing cell development and differentiation, and affecting cell shape and function. The structure of the ECM is, in turn, influenced by the cells within it. Not only do these cells secrete many ECM constituents, but they also help to pattern the matrix. Thus it is evident that cell-ECM interactions are of vital importance.

While a vast amount of useful biological information has been gathered from experiments performed on cells grown on traditional tissue culture substrates such as glass or plastic, there has been increasing interest in developing culture systems and materials that would more accurately reflect the native cellular environment. Such materials would have use not only for cell culture but also for tissue repair and tissue engineering, e.g., for growing cells, tissues, and/or artificial organs or for use in cell-based bioreactors for production of biomolecules.

Many previous efforts to develop such systems have involved the use of materials such as proteins and peptides obtained from animal sources. However, these materials have a number of disadvantages as compared with synthetic materials. For example, they present an increased risk for the transmission of disease. Even when harvested under supposedly sterile conditions, there is a significant risk of contamination. If animal sources are used, there is concern about immunogenicity if the materials are subsequently introduced into the human body, e.g., for tissue repair or as components in artificial organs. In addition, it can be difficult to ensure that different preparations of material have a consistent, reproducible composition. Even when it is possible to achieve consistency with respect to the known components of a material isolated from a natural source, it is hard or impossible to ensure that unknown, perhaps as-yet unidentified components that may affect cell properties, are excluded. Furthermore, in the course of harvesting, processing, and/or reconstituting these natural products they may become damaged or degraded, thus potentially reducing the fidelity with which they replicate the native cellular environment.

Another approach to the development of materials that would mimic the environment provided by the ECM is to produce various ECM constituents by recombinant DNA techniques. For example, expression constructs encoding ECM proteins can be introduced into prokaryotic or eukaryotic cells, and the protein of interest can be purified from the cells or from the medium in the case of secreted proteins. Proteins can be combined in vitro in desired ratios. While likely reducing the likelihood of disease transmission, this approach also suffers from several disadvantages. For example, whenever proteins are manufactured through a biological rather than purely synthetic process, there remains the possibility that undefined components from the culture system will be present even in highly purified preparations. In addition, purification can be time-consuming and costly and can result in protein degradation or denaturation.

Although native ECM consists largely of proteins and proteoglycans, significant efforts have been directed to development of cell culture and tissue engineering materials based on a variety of synthetic, non-amino acid based polymers. For example, aliphatic hydroesters have been widely used for various tissue engineering applications. Among the commonly used fully synthetic materials are polyglycolic acid (PGA), poly(lactic-co-glycolic acid) (PLGA), poly(ethylene glycol) (PEG), poly(propylene glycol), and various copolymers of these and other compounds. However, these materials also suffer from a number of disadvantages. For example, they form fibers with diameters on the order of tens of microns, which is significantly larger than the diameter of fibers found in native ECM. Furthermore, the methods required to introduce cells into matrices formed from such materials may not be readily compatible with physiological requirements for cell viability.

Thus there remains a need for synthetic compositions and materials for cell culture and tissue engineering purposes that would allow the creation of a cellular environment that mimics important aspects of the native cellular environment without the disadvantages associated with products derived from natural sources. For example, it would be desirable to develop a material that could provide biologically relevant stimuli to cells akin to those provided by native ECM components. For applications involving implantation into the body, there remains a particular need for such compositions and materials that elicit no or minimal immune or inflammatory response and for compositions and materials that are degradable within the body. In addition, there remains a need in the art for compositions and materials that would influence cell properties and functions in desirable ways.

SUMMARY OF THE INVENTION

The present invention addresses these needs, among others. The invention encompasses the discovery that it is possible to modify self-assembling peptides by incorporating an additional domain that does not self-assemble, while still permitting assembly of the self-assembling portion. The additional domain can confer a variety of properties on the resulting peptide. Preferably the resulting peptide self-assembles to form nanofibers and, preferably, forms a macroscopic structure. Materials formed by self-assembly of the peptides have a wide variety of uses, particularly in the areas of cell culture, tissue engineering, and tissue repair.

In one aspect, the invention provides a self-assembling peptide comprising (a) a first amino acid domain that mediates self-assembly, wherein the domain comprises alternating hydrophobic and hydrophilic amino acids that are complementary and structurally compatible and self-assemble into a macroscopic structure when present in unmodified form; and (b) a second amino acid domain that does not self-assemble in isolated form. In certain embodiments of the invention the second amino acid domain comprises a biologically active peptide motif, e.g., a peptide motif found in a naturally occurring protein, or a target site for an interaction with a biomolecule. In certain embodiments of the invention the naturally occurring protein is a component of the extracellular matrix, e.g., a component of the basement membrane.

The invention further provides scaffolds comprising the self-assembling peptides, methods of using the scaffolds including for cell culture, tissue engineering, and tissue repair, and methods for selecting amino acid domains.

This application refers to various patents and publications. The contents of all of these are incorporated by reference. In addition, the following publications are incorporated herein by reference: *Current Protocols in Molecular Biology, Current Protocols in Immunology, Current Protocols in Protein Science*, and *Current Protocols in Cell Biology*, all John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001; Freshney, R. I., *Culture of Animal Cells: A Manual of Basic Technique,* 4th ed., John Wiley & Sons, New York, 2000; Harlow, E., Lane, E., and Harlow, E., (eds.) *Using Antibodies: A Laboratory Manual*, Cold Spring Harbor Laboratory Press, Cold Spring Harbor, 1998; *The Extracellular Matrix Factsbook*, by Shirley Ayad, Ray Boot-Handford Academic Press; 2nd edition, 1998; *Guidebook to the Extracellular Matrix, Anchor, and Adhesion Proteins* (The Guidebook Series), by Thomas Kreis, Ronald Vale Sambrook and Tooze Publication at Oxford Univ; 2nd edition, 1999; *The Cytokine Handbook*, 4$^{th}$ ed., A. Thomson, Michael T. Lotze, Angus W. Thomson, Lotze M. Academic Press, 2003; *Goodman and Gilman's The Pharmacological Basis of Therapeutics*, 10$^{th}$ Ed. McGraw Hill, 2001; Katzung, B. (ed.) *Basic and Clinical Pharmacology*, McGraw-Hill/Appleton & Lange; 8th edition (Sep. 21, 2000); and Kandel, E., Schwartz, J. H., Jessell, T. M., (eds.), *Principles of Neural Science*, 4$^{th}$ ed., McGraw Hill, 2000. If there is a conflict between any of the incorporated references and the instant specification, the specification shall control.

DETAILED DESCRIPTION OF CERTAIN EMBODIMENTS OF THE INVENTION

I. Definitions

Figure 1:
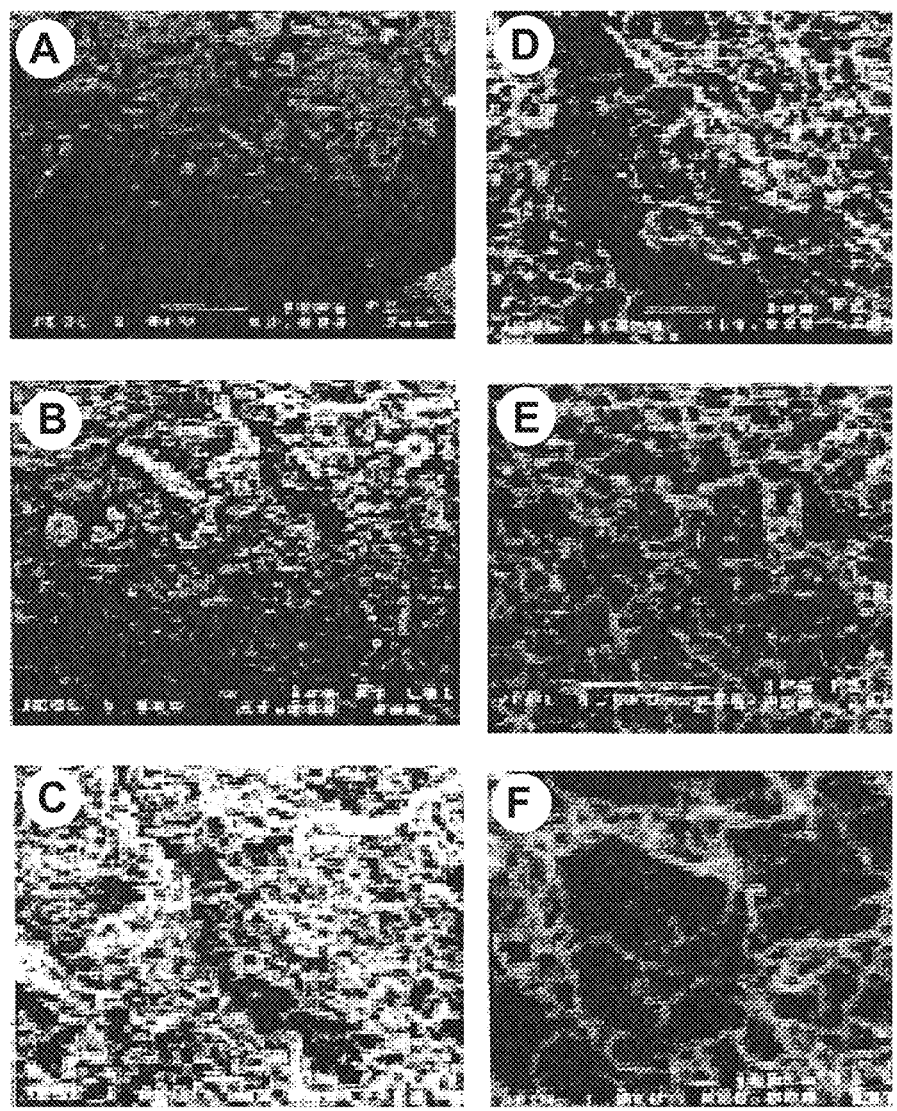
FIGS. 1A-1F show scanning electron microscope (SEM) images of an RAD16-II peptide hydrogel. At low magnifications the scaffold resembles felt (A-C). At high magnifications, the interwoven nanofibers in the structure can be seen (D-F).
Figure 2:
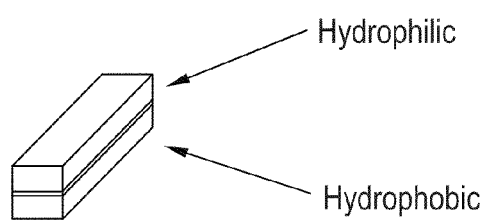
FIG. 2 shows the proposed molecular model of the self-assembly of unmodified self-assembling peptides (in this case an RADA (SEQ ID NO: 4) peptide, RAD16-II). The alanines form an overlapping hydrophobic interaction on one side of the peptide. The arginines and aspartates form complementary ionic bonds on the other side. These ionic self-complementary peptides can undergo molecular self-assembly.
Figure 2:
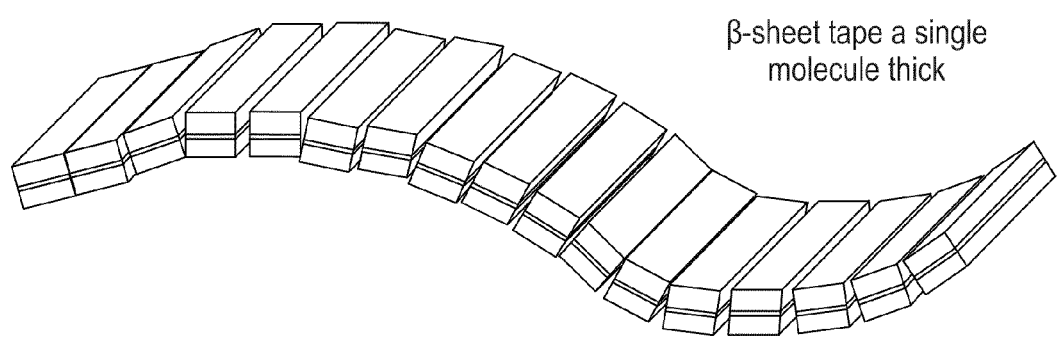

The following definitions are of use in understanding the invention.

Amino acid domain: By "amino acid domain" is meant a contiguous polymer of at least 2 amino acids joined by peptide bond(s). The domain may be joined to another amino acid or amino acid domain by one or more peptide bonds. An amino acid domain can constitute at least two amino acids at the N-terminus or C-terminus of a peptide or can constitute at least two amino acids in the middle of a peptide.

Antibody: In general, the term "antibody" refers to an immunoglobulin, which may be natural or wholly or partially synthetically produced in various embodiments of the invention. An antibody may be derived from natural sources (e.g., purified from a rodent, rabbit, chicken (or egg) from an animal that has been immunized with an antigen or a construct that encodes the antigen) partly or wholly synthetically produced. An antibody may be a member of any immunoglobulin class, including any of the human classes: IgG, IgM, IgA, IgD, and IgE. The antibody may be a fragment of an antibody such as an Fab', F(ab')$_2$, scFv (single-chain variable) or other fragment that retains an antigen binding site, or a recombinantly produced scFv fragment, including recombinantly produced fragments. See, e.g., Allen, T., *Nature Reviews Cancer*, Vol. 2, 750-765, 2002, and references therein. Preferred antibodies, antibody fragments, and/or protein domains comprising an antigen binding site may be generated and/or selected in vitro, e.g., using techniques such as phage display (Winter, G. et al. 1994. *Annu. Rev. Immunol.* 12:433-455, 1994), ribosome display (Hanes, J., and Pluckthun, A. *Proc. Natl. Acad. Sci. USA.* 94:4937-4942, 1997), etc. In various embodiments of the invention the antibody is a "humanized"

antibody in which for example, a variable domain of rodent origin is fused to a constant domain of human origin, thus retaining the specificity of the rodent antibody. It is noted that the domain of human origin need not originate directly from a human in the sense that it is first synthesized in a human being. Instead, "human" domains may be generated in rodents whose genome incorporates human immunoglobulin genes. See, e.g., Vaughan, et al., *Nature Biotechnology*, 16: 535-539, 1998. An antibody may be polyclonal or monoclonal.

Approximately: As used herein, the term "approximately" means that the measurement or number may deviate by up to 10% of the numeral given, in either direction.

Biologically active peptide motif: A "biologically active peptide motif" is a peptide that induces a phenotypic response or change in an appropriate cell type when the cell is contacted with the peptide. The peptide may be present either in isolated form or as part of a larger polypeptide or other molecule. The ability of the peptide to elicit the response may be determined, for example, by comparing the relevant parameter in the absence of the peptide (e.g., by mutating or removing the peptide when normally present within a larger polypeptide). In various embodiments of the invention preferred phenotypic responses or changes include, but are not limited to: enhancement of cell spreading, attachment, adhesion, proliferation, secretion of an ECM molecule, or expression of a phenotype characteristic of a particular differentiated cell type.

Biomolecule: As used herein, a "biomolecule" refers to a molecule such as a protein, peptide, proteoglycan, lipid, carbohydrate, or nucleic acid having characteristics typical of molecules found in living organisms. A biomolecule may be naturally occurring or may be artificial (not found in nature and not identical to a molecule found in nature). For example, a protein having a sequence or modification resulting from the mental process of man, and not occurring in nature, is considered an artificial biomolecule.

Chemotactic substance, as used herein, refers to a substance having the ability to recruit cells to a site at which the substance is present. Such cells may, for example, have the potential to contribute to the formation or repair of a tissue (e.g., by providing growth factors) or to contribute to an immune response. Certain chemotactic substances may also function as proliferation agents.

Complementary: By "complementary" is meant having the capability of forming ionic or hydrogen bonding interactions between hydrophilic residues from adjacent peptides in a fiber of macroscopic scaffold. Each hydrophilic residue in a peptide either hydrogen bonds or ionically pairs with a hydrophilic residue on an adjacent peptide, or is exposed to solvent. Pairing may also involve van der Waals forces.

Endothelial cell: The term "endothelial cell" is to be given its meaning as generally accepted in the art, i.e., the innermost layer of cells that line the cavities of the heart, blood vessels (including capillaries), and lymph vessels. The terms "endothelium" and "vascular endothelium" are used interchangeably herein.

Isolated: As used herein, "isolated" means 1) separated from at least some of the components with which it is usually associated in nature; 2) prepared or purified by a process that involves the hand of man; and/or 3) not occurring in nature.

Iso-osmotic solute: By "iso-osmotic solute" is meant a non-ionizing compound dissolved in an aqueous solution such that the resulting solution (an iso-osmotic solution) has an osmotic pressure or osmolality compatible with cell viability over periods of time greater than 1 minute, preferably greater than 5 minutes, yet more preferably greater than 10 minutes, yet more preferably at least 1 hour. In general, a preferred iso-osmotic solution has an osmotic pressure that approximates the osmotic pressure of the extracellular or intracellular environment of cells (e.g., in tissue culture medium, within a subject, etc.). For example, an iso-osmotic solution may have an osmotic pressure that is within 290±10 mosm/kg $H_2O$. Preferred iso-osmotic solutes include carbohydrates, such as monosaccharides or disaccharides. Examples of preferred carbohydrates include sucrose, glucose, galactose, fructose, ribose, mannose, arabinose, and xylose. Still another preferred iso-osmotic solute is glycerol, such an aqueous solution of glycerol that is between 5 to 20% (v/v) glycerol.

Macroscopic: By "macroscopic" is meant having dimensions large enough to be visible under magnification of 10-fold or less. In preferred embodiments of the invention a macroscopic structure is visible to the naked eye. A macroscopic structure may be transparent and may be two-dimensional, or three-dimensional. If two-dimensional, in certain embodiments of the invention it comprises more than a single layer of molecules, e.g., 2, 3, or more layers of molecules. Typically each dimension is at least 10 µm, in size. In certain embodiments at least two dimensions are at least 100 µm, or at least 1000 µm in size. Frequently at least two dimensions are at least 1-10 mm in size, 10-100 mm in size, or more. The relevant dimensions may be, e.g., length, width, depth, breadth, height, radius, diameter, circumference, or an approximation of any of the foregoing in the case of structures that do not have a regular two or three-dimensional shape such as a sphere, cylinder, cube, etc. Other relevant dimensions may also be used.

Marker: A "marker" may be any gene or gene product (e.g., protein, peptide, mRNA) that indicates or identifies a particular cell type, tissue type, embryological origin, differentiation state, or physiological or metabolic state, or that indicates or identifies a particular diseased or physiological state (e.g., carcinoma, normal, dysplasia). The expression level, or lack of expression, of a marker gene may indicate that the cell or tissue under examination is of a particular cell type or tissue type, or has a particular embryological origin, differentiation state, physiological state, or metabolic state. The expression level, or lack of expression, of a marker gene may indicate a particular physiological or diseased state of a patient, organ, tissue, or cell. Preferably, the expression or lack of expression may be determined using standard techniques such as Northern blotting, in situ hybridization, RT-PCR, sequencing, immunochemistry, immunoblotting, oligonucleotide or cDNA microarray or membrane array, protein microarray analysis, mass spectrometry, etc. In certain embodiments of the invention, the level of expression of a marker gene is quantifiable. The expression of various markers can also be determined by functional assays. For example, expression a cytochrome P450 genes (e.g., in hepatocytes) can be assessed by measuring the ability of a cell or cell lysate to perform a reaction characteristic of the presence of the P450 protein (e.g., to metabolize a particular substrate).

Other markers that indicate or identify a particular cell type can also be used. For example, production of or uptake of a particular compound may be used as a marker. For example, uptake of LDL or production of nitric oxide are useful markers for endothelial cells. Markers are further discussed below.

Microfiber: As used herein, the term "microfiber" refers to a fiber having a diameter of microscale dimensions. Typically a microscale fiber has a diameter of 1000 µm or less, 500 µm or less, 100 µm or less, 50 µm or less, 20 µm or less, between 10 and 20 µm, between 5 and 10 µm (inclusive).

Microscale: As used herein, "microscale" generally refers to structures having dimensions that may most conveniently be expressed in terms of micrometers. For example, the term "microscale structure" may refer to a structure having dimensions of approximately 500 μm or less, approximately 100 μm or less, approximately 50 μm or less, approximately 20-50 μm, approximately 10-20 μm, approximately 5-10 μm, or 1-5 μm. One of ordinary skill in the art will recognize that the length of such structures may run into the millimeters, but that most dimensions are in the micrometer range.

Nanoscale: As used herein, the term "nanoscale" generally refers to materials of structures having dimensions that may most conveniently be expressed in terms of nanometers. For example, the term "nanoscale structure" or "nanoscale scaffold" may refer to a structure having dimensions of less than 1 μm, e.g., approximately 500 nm or less, approximately 100 nm or less, approximately 50 nm or less, approximately 20-50 nm (inclusive), approximately 10-20 nm, approximately 5-10 nm, approximately 1-5 nm, approximately 1 nm, or between 0.1 and 1 nm. The ranges listed are assumed to include both endpoints. The relevant dimensions may be, e.g., length, width, depth, breadth, height, radius, diameter, circumference, or an approximation of any of the foregoing in the case of structures that do not have a regular two or three-dimensional shape such as a sphere, cylinder, cube, etc. Any other relevant dimensions may also be used to determine whether a structure is a nanoscale structure, depending on the shape of the structure. One of ordinary skill in the art will recognize that one or more dimensions of a nanoscale structure need not be in the nanometer range. For example, the length of such structures may run into the micron range or longer. However, generally most dimensions are in the nanometer range.

Nanofiber: As used herein, the term "nanofiber" refers to a fiber having a diameter of nanoscale dimensions. Typically a nanoscale fiber has a diameter of 500 nm or less. According to certain embodiments of the invention a nanofiber has a diameter of 100 nm or less. According to certain other embodiments of the invention a nanofiber has a diameter of 50 nm or less. According to certain other embodiments of the invention a nanofiber has a diameter of 20 nm or less. According to certain other embodiments of the invention a nanofiber has a diameter of between 10 and 20 nm. According to certain other embodiments of the invention a nanofiber has a diameter of between 5 and 10 nm. According to certain other embodiments of the invention a nanofiber has a diameter of less than 5 nm. The ranges listed are assumed to include both endpoints.

Nanoscale environment scaffold: The term "nanoscale environment scaffold" refers to a scaffold comprising nanofibers. According to certain embodiments of the invention at least 50% of the fibers comprising the scaffold are nanofibers. According to certain embodiments of the invention at least 75% of the fibers comprising the scaffold are nanofibers. According to certain embodiments of the invention at least 90% of the fibers comprising the scaffold are nanofibers. According to certain embodiments of the invention at least 95% of the fibers comprising the scaffold are nanofibers. According to certain embodiments of the invention at least 99% of the fibers comprising the scaffold are nanofibers. Of course the scaffold may also comprise non-fiber constituents, e.g., water, ions, growth and/or differentiation-inducing agents such as growth factors, therapeutic agents, or other compounds, which may be in solution in the scaffold and/or bound to the scaffold.

Naturally occurring: As used herein, "naturally occurring" means found in nature. A naturally occurring biomolecule is, in general, synthesized by an organism that is found in nature and is unmodified by the hand of man, or is a degradation product of such a molecule. A molecule that is synthesized by a process that involves the hand of man (e.g., through chemical synthesis not involving a living organism or through a process that involves a living organism that has been manipulated by the hand of man or is descended from such an organism) but that is identical to a molecule that is synthesized by an organism that is found in nature and is unmodified by the hand of man is also considered a naturally occurring molecule.

Peptide, polypeptide, or protein: According to the present invention, a "peptide", "polypeptide", or "protein" comprises a string of at least two amino acids linked together by peptide bonds. A peptide generally represents a string of between approximately 2 and 200 amino acids, more typically between approximately 6 and 64 amino acids. Typically, the self-assembling portion of a self-assembling peptide is about 8-24, frequently about 12-20, or 16-20 amino acids. Peptide may refer to an individual peptide or a collection of peptides. Inventive peptides typically contain only natural amino acids, although non-natural amino acids (i.e., compounds that do not occur in nature but that can be incorporated into a polypeptide chain; see, for example, the Web site having URL www.cco.caltech.edu/~dadgrp/Unnatstruct.gif, which displays structures of non-natural amino acids that have been successfully incorporated into functional ion channels) and/or amino acid analogs as are known in the art may alternatively be employed. In particular, D amino acids may be used. Also, in various embodiments of the invention one or more of the amino acids in an inventive peptide may be altered or derivatized, for example, by the addition of a chemical entity such as an acyl group, a carbohydrate group, a carbohydrate chain, a phosphate group, a farnesyl group, an isofarnesyl group, a fatty acid group, a linker for conjugation or functionalization, etc. In certain embodiments of the invention a peptide is branched, in which case it contains at least two amino acid polymers, each of which consists of at least 3 amino acids joined by peptide bonds, but the two amino acid polymers themselves are not linked by a peptide bond.

Proliferation agent and mitogenic agent are used herein interchangeably to refer to the ability of a substance to enhance the proliferation of cells.

Proteases, as used herein, are protein-cleaving enzymes that cleave peptide bonds that link amino acids in protein molecules so as to generate peptides and protein fragments. A large collection of proteases and protease families has been identified, and specific sites at which these proteases cleave target proteins are known in the art. Some exemplary proteases include serine proteases, aspartyl proteases, acid proteases, alkaline proteases, metalloproteases (e.g. matrix metalloproteases), carboxypeptidase, aminopeptidase, cysteine protease, etc.

Regeneration: In general, in various embodiments of the invention regeneration of tissue may include any aspect of anatomical or functional restoration of the condition of the tissue prior to an injury or a degenerative or degradative process, which involves production of new tissue (by which is meant either cells or portions of cells). In certain embodiments of the invention production of new tissue includes growth of existing cells. For example, in the case of endothelial cells, regeneration may comprise formation of new blood vessels or extension or growth of existing vessels. In the case of neurons regeneration may thus include growth of axons or other neuron processes. Such processes may arise directly from the cell body or may be extensions of processes that were severed or damaged due to injury. The new tissue may replace tissue that was previously present. In certain embodiments of the invention production of new tissue includes division of existing cells.

Repair: In general, in various embodiments of the invention repair of tissue may include any aspect of anatomical or functional restoration of the condition of the tissue prior to damage or degeneration. For example, it may include restoration of physical continuity between portions of tissue that were separated by an injury. Preferably such restoration of physical continuity includes reapposition or reconnection of the portions of tissue without appreciable separation by tissue of a type that was not present prior to the injury, such as scar tissue. Repair may thus include filling of a tissue defect, e.g., by reapposition of portions of tissue separated by the defect and/or by growth of new tissue of the type that was subject to damage or degradation, rather than by development of scar tissue. Repair may, but need not, include growth or development of new tissue. Thus regeneration may be considered one aspect of repair, but repair can occur without evidence of new tissue growth.

Solution that is substantially free of ions: By "solution that is substantially free of ions" is meant a solution to which no ions (or salts thereof) have been added or in which the concentration of ions (or salts thereof) is less than 0.01 or 0.001 mM.

Small molecule: As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

Specific binding: As used herein, the term "specific binding" refers to a physical association between two molecules, which may be referred to as a target molecule (e.g., a target peptide) and a binding molecule. The interaction is typically dependent upon the presence of a particular structural feature of the target molecule such as a target domain that is recognized by the binding molecule. The target molecule may consist entirely a target domain that is recognized by the binding molecule. For example, if a binding molecule is specific for a target molecule that contains target domain A, the presence of a polypeptide comprising target domain A, or the presence of free unlabeled target domain A in a reaction containing both free labeled A and the binding molecule specific thereto, will reduce the amount of labeled A that binds to the binding molecule. It is to be understood that specificity need not be absolute but generally refers to the context in which the binding is performed. Target domains and binding molecules having a sufficient degree of specificity to perform appropriately in any given application can be selected by one of ordinary skill in the art. It is also to be understood that specificity may be evaluated in the context of additional factors such as the affinity of the binding molecule for the target molecule versus the affinity of the binding molecule for other targets, e.g., competitors. Once the specificity of a binding molecule is established in one or more contexts, it may be employed in other, preferably similar, contexts without necessarily re-evaluating its specificity.

Preferred binding molecules in the context of the present invention include proteins that are present on the cell surface, proteins that are present within the body in the extracellular environment (e.g., extracellular matrix proteins, secreted or cell surface proteins including proteases, growth factors, and proteins that circulate in the blood). In certain embodiments of the invention the binding molecule is an antibody. In the context of an interaction between a self-assembling peptide and a binding molecule, according to certain embodiments of the invention, a binding molecule exhibits specific binding if it binds to the target molecule at least 2 times as strongly as to other peptides or polypeptides present in the body within the extracellular environment. According to certain embodiments of the invention, a binding molecule exhibits specific binding if it binds to the target molecule at least 5 times as strongly as to other peptides or polypeptides present in the body within the extracellular environment. According to certain embodiments of the invention, a binding molecule exhibits specific binding if it binds to the target molecule at least 10 times as strongly as to other peptides or polypeptides present in the body within the extracellular environment. According to certain embodiments of the invention, a binding molecule exhibits specific binding if it binds to the target molecule at least 50 times as strongly as to other peptides or polypeptides present in the body within the extracellular environment. According to certain embodiments of the invention, a binding molecule exhibits specific binding if it binds to the target molecule at least 100 times as strongly as to other peptides or polypeptides present in the body within the extracellular environment. It is recognized that since binding is a process that involves an interaction between two molecules in which characteristics such as the strength of binding and the degree of specificity are dependent on features of both molecules, either molecule may be designated as the target molecule or as the binding molecule.

Structurally compatible: By "structurally compatible" is meant capable of maintaining a sufficiently constant intrapeptide distance to allow structure formation. In certain embodiments of the invention the variation in the intrapeptide distance is less than 4, 3, 2, or 1 angstroms. It is also contemplated that larger variations in the intrapeptide distance may not prevent structure formation if sufficient stabilizing forces are present. This distance may be calculated based on molecular modeling or based on a simplified procedure that has been previously reported (U.S. Pat. No. 5,670,483). In this method, the intrapeptide distance is calculated by taking the sum of the number of unbranched atoms on the sidechains of each amino acid in a pair. For example, the intrapeptide distance for a lysine-glutamic acid ionic pair is 5+4=9 atoms, and the distance for a glutamine-glutamine hydrogen bonding pair is 4+4=8 atoms. Using a conversion factor of 3 angstroms per atom, the variation in, the intrapeptide distance of peptides having lysine-glutamic acid pairs and glutamine-glutamine pairs (e.g., 9 versus 8 atoms) is 3 angstroms.

Subject: The term subject, as used herein, refers to an individual to whom an agent is to be delivered, e.g., for experimental, diagnostic, and/or therapeutic purposes. Preferred subjects are mammals, particularly domesticated mammals (e.g., dogs, cats, etc.), primates, or humans.

Substantially uniformly distributed: In general, in the case of a peptide scaffold encapsulating cells, the phrase "substantially uniformly distributed" is intended to convey that the majority of cells are approximately equidistant from one another. For example, cells are considered substantially uniformly distributed if, at any particular time (e.g., immediately after scaffold formation) the center of mass of at least 50, 60, 70, 80, 90, or 100% of the cells encapsulated by the scaffold is separated from the center of mass of the closest cell (i.e., the cell with the closest center of mass) by a distance that varies by less than 500, 100, 50, 20, 10, or 1 µM. Alternatively, cells are considered substantially uniformly distributed if, at any particular time, when the scaffold is divided into contiguous portions (e.g., cubes) having equivalent volumes, the number of cells whose center of mass is contained within a given volume of scaffold differs from the average number of cells whose center of mass is contained within such a volume by less than 50%, less than 40%, less than 30%, less than 20%, or less than 10% of the average number of cells, for at least 50%, at least 60%, at least 70%, at least 80%, or at least 90% of the portions. Scaffolds in which cells are substantially uniformly distributed may retain this property over time, or cells may eventually become substantially uniformly distributed in a scaffold in which cells are not initially substantially uniformly distributed.

Therapeutic molecule, compound, or agent: A "therapeutic molecule, compound, or agent" is a molecule or combination of molecules of any type that, when administered to a subject in need thereof, alleviates one or more symptoms of a disease or undesired clinical condition, reduces the severity of a disease or clinical condition, prevents or lessens the likelihood of development of a disease or undesired clinical condition, or facilitates repair or regeneration of tissue in a manner other than simply providing general nutritional support to the subject. It is to be understood that a therapeutic molecule is generally to be administered in an effective amount, i.e., an amount sufficient to achieve a clinically significant result. A therapeutic molecule can be a small molecule, a biomolecule, etc. See *Goodman and Gilman's The Pharmacological Basis of Therapeutics*, 10$^{th}$ Ed., and Katzung, *Basic and Clinical Pharmacology*, for examples.

Three-dimensional arrangement: By "three-dimensional arrangement" is meant existing in three dimensions. Cells having a three-dimensional arrangement are not all part of the same monolayer. As used herein, a monolayer is a cross section through the peptide scaffold that has a thickness equal to the average diameter of the encapsulated cells and that includes at least one encapsulated cell. The average diameter of a cell may be determined by measuring the average diameter of the cell body. An encapsulated cell is considered part of the monolayer if at least 51% of the volume of the cell is contained in the monolayer. Preferably, immediately after scaffold formation, at least one monolayer contains less than 75, 50, 25, 20, 15, 10, 5, or 1% (in order of preference) of the encapsulated cells. More preferably, immediately after scaffold formation, less than 75, 50, 25, 20, 15, 10, 5, or 1% (in order of preference) of the encapsulated cells are part of the same monolayer.

II. Overview

The development of new biological materials, particularly biologically compatible materials that serve as permissive substrates for cell growth, differentiation, and biological function has broad implications for advancing medical technology and for understanding basic biological characteristics of cells. The present invention encompasses the recognition that it is possible to produce compositions that possess the advantages typically associated with a fully synthetic material and yet possess certain desirable features of materials derived from natural sources. The compositions can be used either in vitro or in vivo for purposes including, but not limited to, cell culture or tissue engineering, tissue regeneration and/or repair, and/or as delivery agents for biologically active molecules such as therapeutic agents.

A class of biologically inspired materials that are made through self-assembly of ionic or polar self-complementary peptides has previously been described (see, e.g., Zhang, S., et al., *Proc. Natl. Acad. Sci. USA*, 90, 3334-3338, 1993; Zhang, S., et al., *Biomaterials*, 16, 1385-1393, 1995; U.S. Pat. Nos. 5,955,343 and 5,670,483). The peptides are complementary and structurally compatible. They are composed of repeating units of alternating hydrophilic and hydrophobic amino acids, in which the charged residues can include alternating positive and negative charges. In general, these peptides self-assemble into various macroscopic structures upon exposure to a sufficient concentration of ions (e.g., monovalent cations) to form a stable macroscopic porous matrix. The matrix can assume various physical forms such as ribbons, tape-like structures, two or three-dimensional scaffolds, etc. Preferred matrices are composed of orderly interwoven filaments typically approximately 10-20 mm or 10-30 nm in diameter, with a pore size on the order of 50-100 mm in diameter (or other relevant dimension). The materials are hydrogels, which typically contain approximately 99% or greater water content. Certain of the peptides undergo self-assembly to form nanofibers that are very highly hydrated (e.g., up to 99.5-99.9%% (1-5 mg/ml) water). Because the hydrogel has such an extremely high water content, cells can freely migrate and form intercellular contacts when cultured on or within the matrix. Such an environment also permits diffusion of small molecules including proteins and signaling molecules. In addition, certain of the hydrogels have a low elastic modulus. While not wishing to be bound by any theory, it has been suggested that the low elastic modulus may facilitate cell-cell communication. The properties of the hydrogels contrast with those of many synthetic materials that are being explored for cell culture and/or tissue engineering or repair. For example, many of these materials comprise microfibers and have much larger pore sizes, presenting an environment that is likely not on the appropriate scale by comparison with cells and their natural environment. In addition, the hydrogels can be formed so as to encapsulate cells during the gel formation process, rather than preformed structures in which cells and seeded and/or embedded.

An important characteristic of these materials is that their properties and mechanical strength can be controlled through manipulation of various peptide parameters (Caplan et al. 2000; Caplan et al. 2000a, Caplan et al. 2002b). For example, it has been shown that the stiffness of the gel increases strongly with peptide concentration. The sequences, characteristics, and properties of the peptides and the structures formed by them upon self-assembly are further discussed in the next section.

The inventors and others have shown that structures made by self-assembly of these peptides are able to support cell attachment, viability, and growth when cells are cultured on the surface of the structure. In addition, a peptide structure formed by self-assembly of RAD16-I (AcN-RADARA-DARADARADA-CONH$_2$) (SEQ ID NO: 46) was able to serve as a substrate for neurite outgrowth and formation of functionally active synapses when neurons were grown on their surface (Holmes, et al., 2000). It has also been demonstrated that the peptide gels support endothelial cell attachment, migration, proliferation and capillary-like structure formation and survival for a period of at least 3 weeks (see WO2003096972). In contrast to other three-dimensional substrates that have been used for studies of angiogenesis in vitro, including collagen or fibrin gels or Matrigel, this angiogenic response was observed in the absence of externally supplied angiogenic factors, and with no significant signs of apoptosis or proteolytic gel degradation.

In addition, it has been shown that cells can be encapsulated within the peptide hydrogels, thus placing the cells in a three-dimensional arrangement within a peptide scaffold, and that the cells maintain viability and function when so encapsulated (see pending U.S. patent applications U.S. Ser. No. 09/778,200, filed Feb. 6, 2001, Entitled "Peptide Scaffold Encapsulation Of Tissue Cells And Uses Thereof", U.S. Ser. No. 10/196,942, entitled "Liver Cellular Reprogramming in Peptide Hydrogel and Uses Thereof". Furthermore, chondrocytes encapsulated within a hydrogel structure formed by self-assembly of KLD12 (AcN-KLDLKLDLKLDL-CONH₂) (SEQ ID NO:47) retained their morphology and developed a cartilage-like, mechanically functional ECM rich in proteoglycans and type-II collagen, indicative of a stable chondrocyte phenotype (Kisiday, et al., 2002). Liver progenitor cells encapsulated within a peptide scaffold made by self-assembly of RAD16-I expressed markers indicative of hepatocyte phenotype (Semino et. al., 2003). Results such as these indicate that the nanoscale environment provided by the self-assembling peptide gels can enhance functional activity of a diverse set of cell types and is permissive for cellular instruction and expression of differentiated cell phenotypes.

Unlike many natural or artificial materials that have been used heretofore in an effort to provide a suitable environment for cell culture, tissue engineering, etc., the materials of the present invention interact with cells on a nanoscale rather than a microscale. The materials are made of nanofibers rather than the microfibers typical of various other materials. While not wishing to be bound by any theory, it is believed that the small size of the fibers and/or the open weave structure of the materials promote extension of cell processes and allow diffusion of nutrients, waste products, etc., in a manner that provides unique advantages for cell growth. The nanofibers that comprise the material may be ordered during self assembly in a complementary fashion due to weak interactive molecular forces. However, they may also be randomly ordered, which may be preferred for certain applications. In other words, while the fibers may have an orderly internal structure, they may lack directionality or alignment with respect to one another. For example, the fibers may not be substantially parallel to one another.

As described further below, the inventors have now unexpectedly discovered that it is possible to extensively modify the previously described self-assembling peptides by incorporating additional amino acid domains (which may also referred to herein as peptide domains if at least 3 amino acids in length) that do not necessarily conform to the structural requirements for self-assembly, without eliminating the ability of the modified peptides to self-assemble to form a macroscopic structure. For example, the self-assembling peptides can be modified to incorporate a non self-assembling amino acid domain which can be, for example, a biologically active peptide motif or a target site for an interaction with a biomolecule. The resulting peptides comprise a self-assembling peptide domain and a non self-assembling amino acid domain. By non self-assembling amino acid domain is meant, an amino acid domain that does not self-assemble when present as an isolated peptide (i.e., when not joined to an unmodified self-assembling peptide) under conditions (e.g., ionic concentration, peptide concentration, pH, temperature) that would result in self-assembly of an unmodified self-assembling peptide designed in accordance with the principles described in section III below. By "does not self-assemble", is meant that the amino acid domain or peptide does not form nanofilaments or nanofibers, does not form a macroscopic structure, or typically, does not form either β sheets, nanofibers, or a macroscopic structure.

The following section describes the self-assembling peptides that can be modified in accordance with the present invention and methods by which the process of self-assembly and/or the features of the assembled structure may be controlled. Subsequent sections describe the methods and compositions of the invention, methods for characterizing structures formed from the inventive modified self-assembling peptides, methods for evaluating cell phenotype and for selecting amino acid domains that are used for modification, etc., in further detail.

III. Self-Assembling Peptides, Structures Made Therefrom, and Methods of Use

A. Peptide Sequences and Macroscopic Structures

The previously described unmodified self-assembling peptides comprise a family of complementary and structurally compatible molecules. The peptides and their properties are described in U.S. Pat. Nos. 5,955,343 and 5,670,483, in co-pending U.S. patent application Ser. No. 09/778,200, filed Feb. 6, 2001, entitled "Peptide Scaffold Encapsulation Of Tissue Cells And Uses Thereof", and elsewhere. These materials are composed of repeating units of hydrophilic and hydrophobic amino acids, in various alternating patterns.

The first molecule of this class, EAK16-II (AEAEAKA-KAEAEAKAK, A, alanine, E, glutamine, and K, lysine; SEQ ID NO:18), a 16 amino acid peptide, was identified as a segment in a yeast protein, zuotin which was originally characterized by binding to left-handed Z-DNA (Zhang et. al., 1992). Based on this peptide, a large number of self-assembling ionic self-complementary peptides have been systematically designed by changing the amino acid sequence and following a periodic pattern. Preferred peptides assume regular secondary structures, e.g., β-sheet structures, in solution (e.g., aqueous solution). This is believed to occur because the peptides contain two distinct surfaces, one hydrophilic and the other hydrophilic and form complementary ionic bonds with regular repeats on the hydrophilic surface (Zhang, et al., 1999). The side-chains of the peptides partition into two faces, a polar face with charged ionic side chains and a non-polar face, e.g., with alanines or other hydrophobic groups. These ionic side chains are self-complementary to one another in that the positively charged and negatively charged amino acid residues can form complementary ionic pairs. These peptides are therefore called ionic, self-complementary peptides.

The complementary ionic sides have been classified into several moduli, i.e., modulus I, II, III, IV, etc., and mixed moduli (Zhang, et al., 1999). If the ionic residues alternate with one positively and one negatively charged residue (−+−+−+−+), the peptides are described as "modulus I;" if the ionic residues alternate with two positively and two negatively charged residues (−−++−−++), the peptides are described as "modulus II."; if the ionic residues alternate with four positively and two negatively charged residues (−−−−++++), the peptides are described as "modulus IV." Peptides meeting the afore-mentioned criteria may be referred to herein as unmodified self-assembling peptides to distinguish them from the self-assembling peptides of the instant invention, which include a peptide domain that does not meet the foregoing criteria and does not self-assemble.

Many modulus I and II self-complementary peptides such as EAKA16-I (SEQ ID NO:6), RADA16-I (SEQ ID NO:1), RAEA16-I (SEQ ID NO:8), and KADA16-I (SEQ ID NO:10) have been analyzed previously (Table 1). These peptides are also referred to as RAD16-I, RAE16-I, KAD16-I, etc. (i.e., the last amino acid in the four amino acid module may be omitted in the abbreviation). Modulus N ionic self-complementary peptides containing 16 amino acids; such as EAK16-W, KAE16-IV, DAR16-IV and RAD16-IV; have also been studied. If the charged residues in these self-assembling peptides are appropriately substituted without changing the overall pattern described above (e.g., the positive charged lysines are replaced by positively charged arginines and the negatively charged glutamates are replaced by negatively charged aspartates), there are essentially no significant effects on the self-assembly process. However, if the positively charged residues, lysine and arginine are replaced by negatively charged residues, such as aspartate and glutamate, the peptides can no longer undergo self-assembly to form macroscopic structures; however, they can still form a beta-sheet structure in the presence of salt.

Other hydrophilic residues, such as asparagine and glutamine, that form hydrogen bonds may be incorporated into the peptides instead of or in addition to charged residues. If the alanines in the peptides are changed to more hydrophobic residues, such as leucine, isoleucine, phenylalanine or tyrosine, these peptides have a greater tendency to self-assemble and form peptide matrices with enhanced strength. Some peptides that have similar compositions and lengths as these aforementioned peptides form alpha-helices and random-coils rather than beta-sheets. Such peptides typically do not form macroscopic structures although structure formation is not absolutely precluded. Thus, in addition to self-complementarity, other factors are likely to be important for the formation of macroscopic structures, such as the peptide length, the degree of intermolecular interaction, and the ability to form staggered arrays.

It is noted that in certain embodiments of the invention a group or radical such as an acyl group (RCO—, where R is an organic group), e.g., an acetyl group ($CH_3CO$—) is present at the N terminus of the peptides in order to neutralize an extra charge positive that may otherwise be present (e.g., a charge not resulting from the side chain of the N-terminal amino acid). Similarly, a group such as an amine group ($NH_2$) may be used to neutralize an extra negative charge that may otherwise be present at the C terminus (e.g., a charge not resulting from the side chain of C-terminal amino acid), thus converting the C terminus into an amide (—$CONH_2$). While not wishing to be bound by any theory, the neutralization of charges on the terminal N and C molecules may facilitate self-assembly. One of ordinary skill in the art will be able to select other suitable groups.

The peptides self-assemble to form macroscopic structures under a variety of conditions, e.g., upon the addition of monovalent cations to an aqueous peptide solution or upon the introduction of a peptide solution to a solution containing monovalent cations. Prior to self-assembly the peptides may be dissolved in a solution that is substantially free of monovalent ions (e.g., cations) or contains only a low concentration of such ions, e.g., less than 10, 5, 1, 0.5, or 0.1 mM. Self-assembly may be initiated or substantially accelerated by the addition of an ionic solute to a peptide solution or by a change in pH. For example, NaCl at a concentration of between 5 mM and 5 M induces the assembly of the peptides to form macroscopic structures within a few minutes. Lower concentrations of NaCl may also induce assembly but at a slower rate. Certain of the peptides can also self-assemble in the absence of significant concentrations of ions, in a process that may be dependent on pH. For example, certain of the peptides may remain in solution at a pH of approximately 3.0 but may self-assemble when the pH is raised.

Alternately, self-assembly may be initiated by introducing the peptides into a solution comprising ions, e.g., standard phosphate buffered saline (PBS), tissue culture medium, or a physiological fluid such as blood, cerebrospinal fluid (CSF), etc. The peptides can thus self-assemble at a location in vivo. Preferred ions include monovalent cations such as $Li^+$, $Na^+$, $K^+$, and $Cs^+$. Preferably, the concentration of the ion is at least 5, 10, 20, or 50 mM in order to induce or substantially accelerate self-assembly. One of ordinary skill in the art will be able to select preferred concentrations of ions based on the particular peptide sequence and/or concentration and desired speed of assembly. In general, the strength of the resulting structure is increased in the presence of ions relative to the strength in the absence of ions, or at a lower ionic concentration (although it is noted that a plateau may be reached at which an increase in ion concentration does not result in increased strength).

As mentioned above, preferred peptides self-assemble to form a network of nanofibers, resulting in hydrogels of water content higher than 99%, when dissolved water in a range of 1-10 mg/ml (Zhang et. al., 1993, Zhang et. al., 1995, Leon et. al., 1998, Holmes et. al., 2000, Caplan et. al., 2000, Caplan et. al., 2002, Kisiday et. al., 2002). FIG. 1 shows the structure of a representative peptide, RAD16-II (RARADA-DARARADADA, R, arginine, A, alanine, D, aspartic acid) (SEQ ID NO: 4) hydrogel as determined by scanning electron microscopy (SEM). As can be seen, the material is self-assembled into interwoven fibers of ~10-20 nm diameter forming enclosures of ~50-100 nm diameter. The nanofiber network can give rise to hydrogel formation, creating a macroscopic structure preferably of a size that can be observed with the naked eye and can be three-dimensional.

The peptides forming the macroscopic structure contain between 8 and 200 amino acids, 8 to 64 amino acids, 8 to 36 amino acids, or 8 to 16 amino acids, inclusive. Lengths of 12-16 amino acids are typically used. The concentration of the peptides prior to self-assembly can range, for example, between 0.01% (0.1 mg/ml) and 99.99% (999.9 mg/ml), inclusive. More preferably the concentration of the peptides prior to self-assembly is between 0.1% (1 mg/ml) and 10% (100 mg/ml), inclusive, particularly for cell culture and/or therapeutic applications. In certain embodiments of the invention the concentration of the peptides prior to self-assembly is between 0.1% (1 mg/ml) and 5% (50 mg/ml), inclusive, or between 0.5% (5 mg/ml) and 5% (50 mg/ml), inclusive. In certain embodiments of the invention the concentration of the peptides prior to self-assembly is approximately 5 mg/ml, approximately 10 mg/ml, approximately 15 mg/ml, or approximately 20 mg/ml.

If desired, peptide scaffolds may be formed with a predetermined shape or volume. To form a scaffold with a desired geometry or dimension, an aqueous peptide solution may be placed in a pre-shaped casting mold, and the peptides induced to self-assemble into a scaffold by the addition of an ion, as described herein. Alternately, the ion may be added to the peptide solution shortly before placing the solution into the mold, provided that care is taken to place the solution into the mold before substantial assembly occurs. The resulting material characteristics, time required for assembly, and geometry and dimensions of the macroscopic peptide scaffold are governed by parameters including the concentration and amount of peptide solution that is applied, the concentration of ion used to induce assembly of the scaffold, the pH, the particular self-assembling peptide sequence, and the dimensions of the casting apparatus. Where the peptide structure or scaffold is to be implanted into the body, the shape may be selected based upon the intended implantation site. The scaffold can exist as a thin layer, e.g., coating the bottom of a conventional tissue culture or floating in a solution, according to various embodiments of the invention. The layer can be several microns thick, e.g., 10 microns, 10-50 microns, 50-100 microns, 100-200 microns, etc. The layer may comprise multiple β sheets layers.

Self-assembled nanoscale scaffolds can be formed with varying degrees of stiffness or elasticity. The peptide scaffolds typically have a low elastic modulus, e.g., in the range of 1-10 kPa as measured in a standard cone-plate rheometer. Such low values permit scaffold deformation as a result of cell contraction, and this deformation may provide a means for cell-cell communication. Scaffold stiffness can be controlled by a variety of techniques including changes in peptide sequence, changes in peptide concentration, and changes in peptide length. Other methods for increasing stiffness can also be used, such as by attaching a biotin molecule to the amino- or carboxy-terminus of the peptides or between the amino- and carboxy-termini, which may then be cross-linked.

The peptides may include L-amino acids, D-amino acids, natural amino acids, non-natural amino acids, or a combination thereof. If L-amino acids are present in the scaffold, degradation produces amino acids that may be reused, e.g., by cells in culture or by cells in a host tissue. The fact that the basic monomeric subunit of the peptides in certain embodiments of the invention are L-amino acids, which occur naturally within the body, distinguishes this class of compounds from numerous other biocompatible substances and may

TABLE 1

Representative Self-Assembling Peptides

| Name | Sequence (n-->c) | Modulus | |
|---|---|---|---|
| RADA16-I | n-RADARADARADARADA-c | I | (SEQ ID NO: 1) |
| RGDA16-I | n-RADARGDARADARGDA-c | I | (SEQ ID NO: 2) |
| RADA8-I | n-RADARADA-c | I | (SEQ ID NO: 3) |
| RAD16-II | n-RARADADARARADADA-c | II | (SEQ ID NO: 4) |
| RAD8-II | n-RARADADA-c | II | (SEQ ID NO: 5) |
| EAKA16-I | n-AEAKAEAKAEAKAEAK-c | I | (SEQ ID NO: 6) |
| EAKA8-I | n-AEAKAEAK-c | I | (SEQ ID NO: 7) |
| RAEA16-I | n-RAEARAEARAEARAEA-c | I | (SEQ ID NO: 8) |
| RAEA8-I | n-RAEARAEA-c | I | (SEQ ID NO: 9) |
| KADA16-I | n-KADAKADAKADAKADA-c | I | (SEQ ID NO: 10) |
| KADA8-I | n-KADAKADA-c | I | (SEQ ID NO: 11) |
| EAH16-II | n-AEAEAHAHAEAEAHAH-c | II | (SEQ ID NO: 12) |
| EAH8-II | n-AEAEAHAH-c | II | (SEQ ID NO: 13) |
| EFK16-II | n-FEFEFKFKFEFEFKFK-c | II | (SEQ ID NO: 14) |
| EFK8-II | n-FEFKFEFK-c | I | (SEQ ID NO: 15) |
| ELK16-II | n-LELELKLKLELELKLK-c | II | (SEQ ID NO: 16) |
| ELK8-II | n-LELELKLK-c | II | (SEQ ID NO: 17) |
| EAK16-II | n-AEAEAKAKAEAEAKAK-c | II | (SEQ ID NO: 18) |
| EAK12 | n-AEAEAEAEAKAK-c | IV/II | (SEQ ID NO: 19) |
| EAK8-II | n-AEAEAKAK-c | II | (SEQ ID NO: 20) |
| KAE16-IV | n-KAKAKAKAEAEAEAEA-c | N | (SEQ ID NO: 21) |
| EAK16-IV | n-AEAEAEAEAKAKAKAK-c | N | (SEQ ID NO: 22) |
| RAD16-IV | n-RARARARADADADADA-c | N | (SEQ ID NO: 23) |
| DAR16-IV | n-ADADADADARARARAR-c | N | (SEQ ID NO: 24) |
| DAR16-IV* | n-DADADADARARARARA-c | N | (SEQ ID NO: 25) |
| DAR32-IV | n-(ADADADADARARARAR)-c | N | (SEQ ID NO: 26) |
| EHK16 | n-HEHEHKHKHEHEHKHK-c | N/A | (SEQ ID NO: 27) |
| EHK8-I | n-HEHEHKHK-c | N/A | (SEQ ID NO: 28) |
| VE20* | n-VEVEVEVEVEVEVEVEVEVE-c | N/A | (SEQ ID NO: 29) |
| RF20* | n-RFRFRFRFRFRFRFRFRFRF-c | N/A | (SEQ ID NO: 30) |

N/A denotes not applicable
*These peptides form a n-sheet when incubated in a solution containing NaCl, however they have not been observed to self-assemble to form macroscopic structures.

offer unique advantages. The peptides may be chemically synthesized or purified from natural or recombinant sources, and the amino- and carboxy-termini of the peptides may be protected or not protected. The peptide scaffold may be formed from one or more distinct molecular species of peptides which are complementary and structurally compatible with each other. Peptides containing mismatched pairs, such as the repulsive pairing of two similarly charged residues from adjacent peptides, may also form structures if the disruptive force is dominated by stabilizing interactions between the peptides. Peptide scaffolds may also be referred to herein as peptide hydrogels or peptide hydrogel scaffolds.

Peptides, including peptides capable of being cross-linked, and modified self-assembling peptides of the invention may be synthesized using standard f-moc chemistry and purified using high pressure liquid chromatography. The formation of a peptide scaffold may be initiated by the addition of ions or salts thereof as described herein. Hydrophobic residues with aromatic side chains may be cross-linked by exposure to UV irradiation. The extent of the cross-linking may be precisely controlled by the predetermined length of exposure to UV light and the predetermined peptide concentration. The extent of cross-linking may be determined by light scattering, gel filtration, or scanning electron microscopy using standard methods. Furthermore, the extent of cross-linking may also be examined by HPLC or mass spectrometry analysis of the structure after digestion with a protease. Material strength may be determined before and after cross-linking.

B. Cell Culture and Encapsulation

Peptide hydrogels formed either from unmodified self-assembling peptides or the modified self-assembling peptides of the instant invention may be used in a variety of ways for culturing cells and tissues. Cells and tissues can be cultured on the surface of a hydrogel structure. While not wishing to be bound by any theory, inventors suggest that such an environment more closely mimics the natural cellular environment than culture on a rigid substrate such as a conventional plastic tissue culture dish. If the hydrogel forms a three-dimensional structure, cells can extend processes into the structure or migrate into it.

Cells can also be encapsulated within the hydrogel. To encapsulate cells within a peptide structure, peptides and living cells may be incubated in an aqueous solution having an iso-osmotic solute at an appropriate concentration to support cell viability, under conditions that in which the peptides are not substantially self-assembled. In certain embodiments of the invention the solution contains a monovalent cation concentration of less than 10, 5, 1, or 0.1 mM or is substantially free of monovalent cations. The solution may also contain less than less than 10, 5, 1, or 0.1 mM or be substantially free of other ionic species, e.g., other cations or anions. Sufficient ion (e.g., monovalent cation) is added to the solution to initiate self-assembly of the peptides into a macroscopic structure, preferably a β-sheet macroscopic structure, whereby the cells are encapsulated by the formation of the macroscopic structure. The encapsulated cells are preferably present in the macroscopic structure in a three-dimensional arrangement. The solution may be contained in a pre-shaped mold dimensioned to establish a desired volume or shape of the macroscopic structure.

In certain embodiments of the invention the concentration of the added ion is at least 5, 10, 20, or 50 mM. Suitable ions include, but are not limited to, $Li^+$, $Na^+$, $K^+$, and $Cs^+$. In some embodiments, the concentration of the iso-osmotic solute is at least 50, 150, or 300 mM. In other embodiments, the concentration of the iso-osmotic solute is contained in one of the following ranges 200 to 250 mM, 250 to 270 mM, 270 to 300 mM, 300 to 400 mM, 400 to 500 mM, 500 to 600 mM, 600 to 700 mM, 700 to 800 mM, or 800 to 900 mM, inclusive. Suitable iso-osmotic solutes include, but are not limited to, carbohydrates, such as sucrose, mannitol, etc. Other iso-osmotic solutes. preferably non-toxic to cells at the concentration used, may be employed. Self-assembly can also be effected by a change in pH (e.g., a rise from a low pH to a higher pH).

Cells and agents such as bioactive molecules (e.g., differentiation-inducing agents, proliferation agents), therapeutic compounds, may be introduced into the peptide solution prior to self-assembly. The self-assembly process then forms a structure that encapsulates the cells or molecules. To achieve even distribution of the cells or molecules within the structure it may be desirable to thoroughly mix the solution prior to initiation of self-assembly. It may be desirable to maintain the cells or agents in a solution that contains substantially no ions or only low concentration of ions in order to avoid initiation or acceleration of self-assembly immediately upon combining the cells or agents with the peptide solution. In this case the cells are preferably maintained in an iso-osmotic solute such as sucrose prior to combination with the peptide solution. The peptides themselves may be dissolved in an iso-osmotic solution to which cells (e.g., a cell pellet) or agents are added. The resulting composition may be mixed to achieve a more uniform distribution of cells and/or agents, following which the composition is exposed to ions (e.g., ions are added to the composition, or the composition is mixed with a solution containing ions).

Cells may be cultured on the surface of a peptide hydrogel structure in a similar manner to that in which they are cultured on a conventional substrate such as a tissue culture dish or slide, or a tissue culture dish or slide that is coated with a biologically derived material such as collagen, Matrigel, etc. In general, cells can be cultured at any desired degree of confluence. If encapsulated, the cells are preferably present in the macroscopic structure in a three-dimensional arrangement. The density of the cells may be, for example, between $5\times10^3$/ml and $5\times10^4$/ml, between $5\times10^4$/ml and $5\times10^5$/ml, between $5\times10^5$/ml and $5\times10^6$/ml, or between $5\times10^6$/ml and $5\times10^7$/ml, with endpoints included. Other ranges may also be used. Conditions for culturing should preferably be close to physiological conditions. For example, the pH of the culture medium should preferably be close to physiological pH, preferably between pH 6-8, for example about pH 7 to 7.8, in particular pH 7.4. Physiological temperatures range between about 30° C. to 40° C. Mammalian cells are preferably cultured at temperatures between about 32° C. to about 38° C., e.g., between about 35° C. to about 37° C.

Cells may be cultured on or within the peptide structure for any appropriate time, depending upon the cell number and density desired, the proliferation rate of the cells, and the time required for the desired cellular reprogramming to occur. These parameters will vary depending upon the particular cells and purposes for which the invention is to be used. One of ordinary skill in the art will be able to vary these parameters and to observe the effects of doing so, in order to determine the optimal time for maintaining cells in culture on or within the structure. In certain embodiments of the invention the cell are cultured for approximately 3 days, 7 days, 14 days, 21 days, 28 days, 56 days, or 90 days. In certain embodiments of the invention the cells are cultured for between 1 and 3 days inclusive, between 4 and 7 days inclusive, between 8 and 14 days inclusive, between 15 and 21 days inclusive, between 22 and 28 days inclusive, between 29 and 56 days inclusive, or between 57 and 90 days inclusive. Longer or shorter culture periods may also be used.

Preferably, at least 40, 50, 60, 70, 80, 90, or 95% of the cells (either cultured on a surface or encapsulated) are viable 1, 2, 4, 6, or more weeks after formation of the macroscopic scaffold. In another preferred embodiment, at least 50%, at least 60%, at least 70%, at least 80% or 90% of the cells are viable one day or one week after formation of the macroscopic scaffold.

In general, any cell type can be cultured and/or encapsulated in accordance with the present invention including, but not limited to, vascular endothelial cells and precursors thereof, bone marrow cells, periosteal cells, perichondrial cells, fibroblasts, skeletal myoblasts or myocytes, neuronal cells, hippocampal cells, epidermal cells, non-vascular endothelial cells or smooth muscle cells, keratinocytes, basal cells, spinous cells, granular cells, embryonic stem cells, lung cells, immune system cells, ovarian cells, pancreatic cells, cervical cells, liver cells, or foreskin cells. The cells may comprise embryonic, fetal, or adult stem cells, e.g., stem cells that are able to or can be induced to differentiate into any of the preceding cell types.

Sources of the cells may also include fetal or adult organisms, particularly mammals or established cell lines. Numerous established cell lines are known in the art, many of which are available through the American Type Culture Collection (see web site having URL www.atcc.org, which also provides references describing these cell lines). In discussing cells and cell lines, the phrase "derived from" indicates that a cell is obtained from a particular source, or that the cell is a descendant of a cell obtained from that source. For example, a liver-derived cell is a cell that is obtained from the liver or the progeny or descendant of such a cell. When the term "progeny" is used herein, it refers not only to the immediate products of cell division but also to the products of subsequent cell divisions, i.e., to cells that are descendants of a particular cell. A cell that is derived from a cell line is a member of that cell line or is the progeny or descendant of a cell that is a member of that cell line. A cell derived from an organ, tissue, individual, cell line, etc., may be modified in vitro after it is obtained. Such a cell is still considered to be derived from the original source.

Methods for isolating cells are known in the art. Cells harvested from an individual may be used either with or without a period of expansion in culture. Alternately, cells that have been propagated in culture as a stable cell line may be used. In certain embodiments of the invention, e.g., in certain therapeutic applications (see below) the cells are autologous while in other embodiments of the invention the cells are allogeneic or xenogeneic. When non-autologous cells are used, the cells may be treated in various ways prior to introduction into the body in order to reduce the likelihood or reduce the extent of an immune system response by the subject. Such treatments can include modifying, masking, or eliminating an antigen on the surface of a cell as described, for example, in PCT/US00/20129.

In certain embodiments of the invention cells are harvested from a subject, e.g., a patient, and a clonal cell line is derived from one or more of these cells. Clonal lines may be obtained by limiting dilution plating or single cell sorting. Methods for deriving clonal cell lines are well known in the art and are described for example in Puck, T. T. and Marcus, P. I., J. (1956) Experimental Medicine 103, 653; Nias, A. H. W. and Lajtha, L. G. (1965) "Clone size distribution in the study of inhomogeneity of growth rates in tissue culture" in Cell Culture, C. V. Ramakrishnan, ed. (Dr. W. Junk Publishers, Netherlands), and Leong, P.-M., Thilly, W. G., and Morgenthaler, S. (1985) "Variance estimation in single-cell mutation assays: comparison to experimental observations in human lymphoblasts at 4 gene loci", *Mutat Res.*, June-July; 150(1-2):403-10. Cells from the cell line are used in the practice of the invention. When intended for treatment of a particular patient, cells from a matched donor may be advantageously used. Cells isolated from an individual or maintained as a cell line may be cultured according to any appropriate technique including standard cell culture techniques prior to their use in the practice of the present invention.

It may be desirable to genetically alter the cells prior to their use in the invention. Numerous methods for introducing exogenous genetic material into cells are well known in the art. (See, e.g., PCT/US00/20129). Such methods typically include introducing genetic material such as a nucleic acid molecule (e.g., DNA) into the cell, wherein the nucleic acid molecule encodes a product to be expressed by the cell. The product can be, for example, a reprogramming agent such as a growth factor, a transcription factor which will in turn induce expression of other gene products, etc. In certain embodiments of the invention it may be desirable to introduce a selectable marker into the cells. In certain embodiments of the invention it may be desirable to introduce a gene that encodes a selectable marker (e.g., a gene encoding a protein that confers drug resistance) or a detectable marker (e.g., GFP) under the control of a tissue-specific promoter. Expression of the detectable marker may then be used as a means to determine whether the cell or its progeny has differentiated, dedifferentiated, or transdifferentiated along a particular cell lineage pathway characteristic of that tissue. The marker may also be used as a means of isolating cells that have differentiated, dedifferentiated, or transdifferentiated along a particular pathway, e.g., by using immunological methods, FACS, etc., or such other methods as are well known in the art. Numerous selectable and detectable markers are known in the art. In addition, tissue-specific, organ-specific, and lineage-specific promoters are well known. Genes may be introduced under the control of either a constitutive or an inducible promoter of which many are known in the art.

Scaffolds on which cells are cultured or in which cells are encapsulated may be subjected to various environmental conditions that may affect cell phenotype. For example, scaffolds may be subjected to various defined or predetermined mechanical stresses, e.g., shear stress, compression schemes, etc., that may result in altered synthesis of ECM components. It is well known, for example, that flow, e.g., pulsatile flow, can alter the secretion of proteins by cells cultured in vitro. Cells in native articular cartilage and in tissue-engineered constructs respond to mechanical stimuli through multiple regulatory pathways. Such stimuli result in altered intra- and intercellular signalling, alterations in transcription level, protein translation, post-translational modifications, and synthesis of intracellular and extracellular macromolecules (Lee, et al., 2003).

IV. Modified Self-Assembling Peptides and Structures Formed by Self-Assembly Thereof A. Modification of Self-Assembling Peptides by Addition of Amino Acid Domain The previously identified self-assembling peptides conform to particular structural requirements that allow them to self-assemble, as described above. These requirements accord with both theoretical studies of peptide self-assembly and experimental observations of the self-assembly behavior, or lack thereof, of a number of different peptides. However, the possibility that the peptides may be significantly modified by addition of amino acid domains that do not conform to the above-described structural requirements, without eliminating the ability of a peptide containing the modification to self-assemble, has not previously been explored.

The inventors have discovered an unanticipated flexibility in that the self-assembling peptides can be modified by the addition of amino acid domains that would not self-assemble if present in isolated form under conditions (e.g., ionic strength, peptide concentration, pH, temperature) in which the previously described peptides (modulus I, II, III, IV, etc.) would self-assemble. Furthermore, in preferred embodiments of the invention the addition of the non self-assembling amino acid domain does not prevent the modified peptide from self-assembling, e.g., to form nanofibers, a macroscopic structure, or both. Preferably the modified peptide self-assembles to form a macroscopic structure composed of nanofibers. Although the resulting structure may be less strong and/or stable than a structure resulting from self-assembly of the unmodified peptide, visual observation and/or rheological studies, as described in the examples, confirm that gel formation occurs. The modified peptides may thus be used for the various purposes described herein. For purposes of the present invention, a self-assembling peptide that possesses the structural features described in the previous section and does not include a portion lacking those characteristics will be referred to as an unmodified self-assembling peptide. (It is to be understood that an unmodified self-assembling peptide may be altered in any of a number of ways described above that do not include addition of amino acids to the peptide. Such altered self-assembling peptides are not referred to as "modified" within the meaning of the term as used herein but rather as "altered" or "derivatized".) The modified self-assembling peptides of the invention are distinct from naturally occurring molecules, i.e., they are not found in naturally occurring molecules, although one or more of the amino acid domains in an inventive peptide may occur in a naturally occurring molecule. They can therefore be considered "isolated" or "synthetic", meaning that the total sequence of the peptide does not occur in nature without the intervention of man.

A peptide that includes an amino acid domain comprising an unmodified self-assembling peptide and a second amino acid domain that lacks one or more of the structural features of an unmodified self-assembling peptide, and thus does not self-assemble to form nanofibers or to form a macroscopic structure under conditions that would result in self-assembly of an unmodified self-assembling peptide, is referred to as a "modified self-assembling peptide" if it is capable of self-assembly (e.g., to form nanofibers, a macroscopic structure, or preferably, both) under conditions that would result in self-assembly of an unmodified self-assembling peptide. It will be appreciated that, in general, a modified self-assembling peptide will correspond to a particular unmodified self-assembling peptide that does not include the second amino acid domain but that has the same self-assembling portion. In certain embodiments of the invention the conditions under which self-assembly of the modified self-assembling peptide occurs are the same as the conditions under which the corresponding unmodified self-assembling peptide assembles. In other embodiments of the invention, the conditions under which self-assembly of the modified self-assembling peptide occurs are different from the conditions under which the corresponding unmodified self-assembling peptide assembles. In this case the conditions for self-assembly of the modified self-assembling peptide are the same as the conditions under which a different (non-corresponding) unmodified self-assembling peptide self-assembles.

The inventive modified self-assembling peptides thus comprise (a) a first amino acid domain that mediates self-assembly, wherein the domain comprises alternating hydrophobic and hydrophilic amino acids that are complementary and structurally compatible and self-assemble into a macroscopic structure; and (b) a second amino acid domain that does not self-assemble in isolated form (i.e., when present as the only peptide in a solution under conditions that would result in assembly of an unmodified self-assembling peptide as described above). Preferably the second amino acid domain permits assembly of the first amino acid domain so that the peptide assembles to form nanofibers, and/or a macroscopic structure. In preferred embodiments of the invention the peptide forms β sheets.

In certain embodiments of the invention an amino acid domain is at least 3 amino acids, at least 4 amino acids, at least 5 amino acids, at least 6 amino acids, at least 7 amino acids, at least 8 amino acids, at least 9 amino acids, at least 10 amino acids, or more, e.g., 15 or 16 amino acids, 20 amino acids, etc. However, it will generally be desirable to limit the length of the second amino acid domain so as not to interfere too greatly with self-assembly. For example it may be preferable to limit the length of the second amino acid domain to 20 amino acids or less, 16 amino acids or less, 12 amino acids or less, 10 amino acids or less, 8 amino acids or less, etc. It may be desirable to maintain a certain ratio of amino acids in the self-assembling and non self-assembling portions of the peptide. For example, in certain embodiments of the invention it may be desirable for the non self-assembling domain to constitute 50% of less of the total number of amino acids in the peptide.

It may be desirable for the self-assembling portion to be 12 amino acids or greater in length, e.g., 16 amino acids or longer. In particular, if a non self-assembling domain is present between two self-assembling domains, it may be desirable for each of the self-assembling domains flanking the non self-assembling domain to be greater than 8 amino acids in length, e.g., 12 amino acids, 16 amino acids, etc. While not wishing to be bound by any theory, it is possible that including a non self-assembling domain between self-assembling portions rather than at an N or C terminus will be more likely to disrupt self-assembly, since the non self-assembling portion cannot freely extend from a self-assembled structure in such a case. Furthermore, if contained between two self-assembling portions, there is likely to be less opportunity for the motif to interact freely with cells and/or molecules such as proteins present in the culture environment. Thus for various reasons it may be preferable to add the non self-assembling portion to the N or C terminus rather than to insert it between two self-assembling portions.

Figure 3:
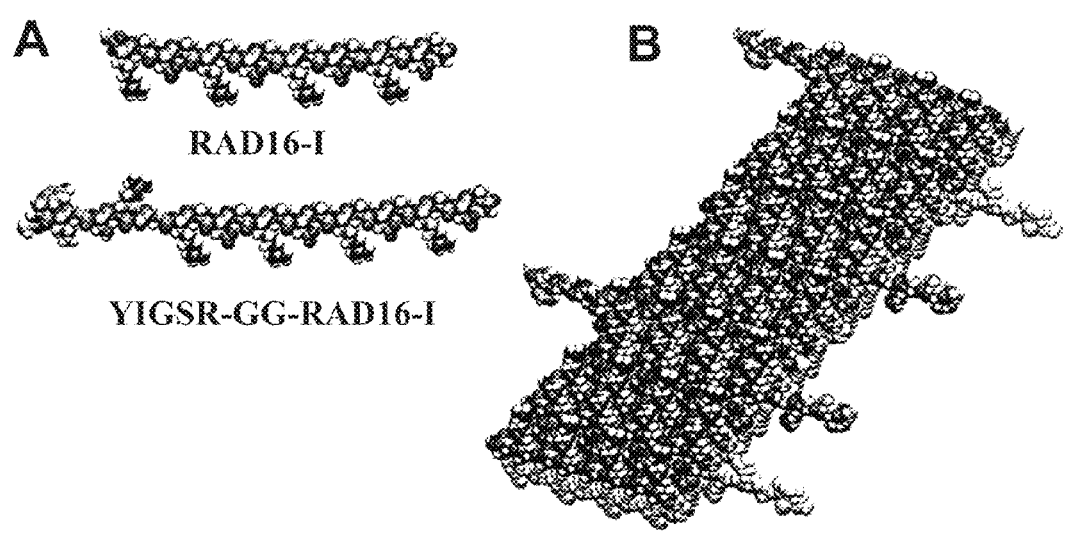
FIG. 3A shows molecular models representing peptide RAD16-I (top) and peptide RAD16-I modified to include a YIGSR (SEQ ID NO: 33) peptide motif at its N terminus (bottom). Molecular models were built with CHARMM (Brooks, et al., 1983) and visualized using VMD (Humphrey, et al., 1996).
FIG. 3B shows a molecular model representing a double β-sheet tape of a self-assembled peptide nanofiber obtained from a mix composed of peptide RAD16-I and peptide YIGSR (SEQ ID NO:33) in a 9:1 v/v ratio. Note the sequences YIGSR (SEQ ID NO:33) extending out from the nanofiber tape.
FIG. 3C shows a schematic representation of a generic peptide hydrogel network in which some of the peptides are modified to include bioactive peptide motifs extending from the amino termini of the base peptide. Close up: stacked self-assembling peptide nanofiber and the extended sequence of the bioactive peptide motif at the amino termini of one of the sequences.
FIG. 3D shows a variety of possible configurations for modified self-assembling peptides. Domain A represents a self-assembling peptide domain. Domain B represents a modifying peptide domain. As indicated in the figure, a modifying domain may be present at the N and/or C terminus of the self-assembling domain, or may be present between two self-assembling domains. (Not to scale.)

FIG. 3A shows molecular models representing a representative self-assembling peptide RAD16-I (top) and peptide RAD16-I modified to include a non self-assembling amino acid domain (YIGSR; SEQ ID NO:33) at its N terminus (bottom). FIG. 3D shows a variety of possible configurations for modified self-assembling peptides in accordance with the invention. Domain A represents a self-assembling amino acid domain. Domain B represents a non self-assembling amino acid domain (modifying domain). As indicated in the figure, a modifying domain may be present at the N and/or C terminus of the self-assembling domain, or may be present between two self-assembling domains.

The amino acid domains may be joined via a linker or bridge, which may be one or more amino acids or a different molecular entity. The linker may allow a non self-assembling domain (e.g, a biologically active peptide motif as described below) to extend from an edge or surface of the macroscopic structure. While not wishing to be bound by any theory, this may facilitate interactions of such an active motif with cells cultured on or in a peptide structure. A linker domain consisting of one or more glycine (G) residues, e.g., 1, 2, 3, 4, 5, etc.

glycines, may be used. Glycine may be preferred because it is small and has a nonpolar side chain, thus minimizing the likelihood of substantial interference with self-assembly. Alanine or other amino acids having nonpolar side chains could also be used.

While the modified peptides described in the examples were made by solid phase synthesis of the extended peptide, resulting in a linear chain, variations in which the modifying motif is conjugated or cross-linked to a side chain are also encompassed within the present invention. Methods for achieving such conjugation or cross-linking are well known in the art. For example, a peptide containing a cysteine residue (or any amino acid modified to include a sulfur atom) can be coupled to a second peptide containing a sulfur atom by formation of disulfide bonds. Thus, in general, the modified self-assembling peptide may be a single linear polymer of amino acids joined by peptide bonds (a structure that may be preferred), or may have a branched structure in which two polymers of amino acids (each being a polymer of amino acids joined by peptide bonds) are attached to one another either covalently or non-covalently (e.g., via a biotin-avidin interaction).

Examples of cross-linking methods include, but are not limited to, the glutaraldehyde method which couples primarily through the α-amino group and ε-amino group, maleimide-sulfhydryl coupling chemistries (e.g., the maleimidobenzoyl-N-hydroxysuccinimide ester (MBS) method), and periodate oxidation methods. In addition, numerous cross-linking agents are known. Exemplary cross-linking agents include, e.g., carboiimides, N-Hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), etc. For additional information on conjugation methods and crosslinkers see generally the journal *Bioconjugate Chemistry*, published by the American Chemical Society, Columbus Ohio, PO Box 3337, Columbus, Ohio, 43210. See also "Cross-Linking", Pierce Chemical Technical Library, available at the Web site having URL, www.piercenet.com and originally published in the 1994-95 Pierce Catalog and references cited therein and Wong S S, *Chemistry of Protein Conjugation and Crosslinking*, CRC Press Publishers, Boca Raton, 1991. Bifunctional crosslinking reagents contain two reactive groups, thereby providing a means of covalently linking two target groups. The reactive groups in a chemical crosslinking reagent typically belong to the classes of functional groups including succinimidyl esters, maleimides, and iodoacetamides. A number of common schemes for forming a heteroconjugate involve the indirect coupling of an amine group on one biomolecule to a thiol group on a second biomolecule, usually by a two- or three-step reaction sequence. The high reactivity of thiols and their relative rarity in most biomolecules make thiol groups good targets for controlled chemical crosslinking. If neither molecule contains a thiol group, then one or more can be introduced using one of several thiolation methods. The thiol-containing biomolecule may then be reacted with an amine-containing biomolecule using a heterobifunctional crosslinking reagent, e.g., a reagent containing both a succinimidyl ester and either a maleimide or an iodoacetamide. Amine-carboxylic acid and thiol-carboxylic acid crosslinking may also be used. For example, 1-Ethyl-3-(3-dimethylaminopropyl)carbodiimide (EDAC) can react with biomolecules to form "zero-length" crosslinks, usually within a molecule or between subunits of a protein complex. In this chemistry, the crosslinking reagent is not incorporated into the final product.

Several methods are available for introducing thiols into biomolecules, including the reduction of intrinsic disulfides, as well as the conversion of amine, aldehyde or carboxylic acid groups to thiol groups. Disulfide crosslinks of cystines in proteins can be reduced to cysteine residues by dithiothreitol (DTT), tris-(2-carboxyethyl)phosphine (TCEP), or tris-(2-cyanoethyl)phosphine. Amines can be indirectly thiolated by reaction with succinimidyl 3-(2-pyridyldithio)propionate (SPDP) followed by reduction of the 3-(2-pyridyldithio)propionyl conjugate with DTT or TCEP. Amines can be indirectly thiolated by reaction with succinimidyl acetylthioacetate followed by removal of the acetyl group with 50 mM hydroxylamine or hydrazine at near-neutral pH. Tryptophan residues in thiol-free proteins can be oxidized to mercaptotryptophan residues, which can then be modified by iodoacetamides or maleimides.

B. Peptide Mixtures

The invention encompasses the recognition that it is possible to mix one or more unmodified self-assembling peptides together with one or more modified self-assembling peptides of the present invention in various ratios and that macroscopic structures comprising both unmodified and modified self-assembling peptides can be formed from such mixtures. The resulting structures can have certain advantageous features relative to structures formed by self-assembly of a homogeneous self-assembling peptide (i.e., 100% of a single peptide). For example, as mentioned above, the modified self-assembling peptides may result in macroscopic structures that are weaker than structures formed from the corresponding unmodified peptide, e.g., they may have less gel-like character. However, the modified peptides may induce desirable cell phenotypes, may desirably alter cell behavior, may desirable alter the binding of ECM molecules, etc. A macroscopic structure formed from a composite (also referred to as a blend) of unmodified and modified self-assembling peptide(s) may have mechanical properties resembling those of macroscopic structures formed by self-assembly of the unmodified peptide while possessing the ability to influence cell behavior, phenotype, etc., in desirable ways. It is also recognized that a peptide scaffold composed of only a modified self-assembling peptide may be less than optimal from the point of view of effects on cells. For example, if every peptide in the gel is modified, the resulting concentration of a biologically active peptide motif may be greater than is desirable and may actually inhibit cell attachment, proliferation, etc., or be toxic to cells.

In general, a wide variety of ratios of unmodified to modified peptide can be used, depending on the desired properties of the macroscopic scaffold to be formed. For example, the ratio of unmodified to modified can be 100:1, 50:1, 25:1, 10:1, 5:1, 2:1, 1:1, 1:2, 1:5, 1:10, 1:25, 1:50, 1:100, etc. These ratios are listed for exemplary purposes and are not intended to be limiting. As described in the Examples, a ratio of 9:1 has been tested with a number of peptides. The peptides can be mixed on a molar basis or based on weight, volume of peptide solution, etc. The peptides can be mixed in dry form, following which a mixed peptide solution is formed. Alternately, each peptide may be dissolved, and the resulting solutions mixed together. The invention also encompasses mixing multiple modified self-assembling peptides with or without the addition of an unmodified self-assembling peptide so as to generate a macroscopic structure that combines desired features of the different modified self-assembling peptides. The various modified self-assembling peptides may contain different amino acid domains, either from the same naturally occurring protein or from different proteins, or entirely artificial amino acid domains, etc.

In certain embodiments of the invention a modified self-assembling peptide does not self-assemble when present as the only peptide in a solution under conditions that would result in assembly of the corresponding unmodified peptide, but does self-assemble together with unmodified self-assembling peptides when present in combination with such peptides. Self-assembly may result in a composition composed of nanofibers, preferably forming a macroscopic structure, that contain a mixture of both unmodified peptides and modified peptides, e.g., primarily unmodified peptides. Alternately, the composition may contain some nanofibers that do not contain any modified peptides while other nanofibers do contain such peptides. While not wishing to be bound by any theory, the inventors suggest that in general, the lower the concentration of modified peptide, the more likely the resulting mixture is to form nanofibers and/or a macroscopic structure, and the stronger the resulting structure will be, relative to the situation in which only modified peptides are provided.

FIG. 3B shows a molecular model representing a double β-sheet tape of a self-assembled peptide nanofiber formed by self-assembly of a mix composed of peptide RAD16-I and a modified RAD16-I peptide extended at its N terminus with the amino acid domain YIGSR (SEQ ID NO:33) in a 9:1 blend (based on volume ratio of peptides dissolved at equal concentrations on a w/w basis). Note the sequences YIGSR (SEQ ID NO:33) extending out from the nanofiber tape. In general, the modifying amino acid domain may extend from a lateral edge of an assembly of peptides (e.g., a nanofiber or macroscopic structure) or from a surface. Other arrangements are also possible.

Figure 3C:
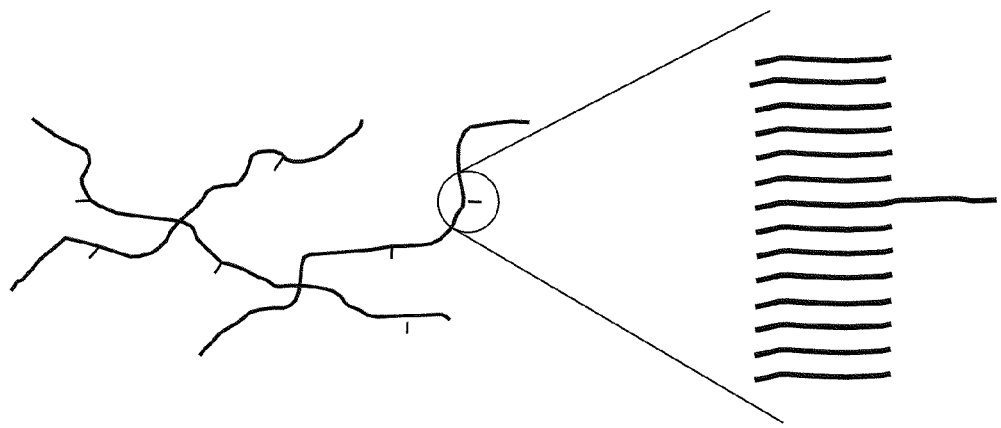
Figure 3D:
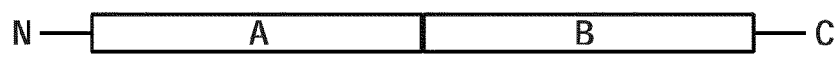
Figure 3D:
Figure 3D:
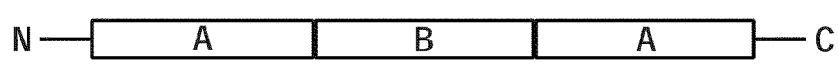
Figure 3D:
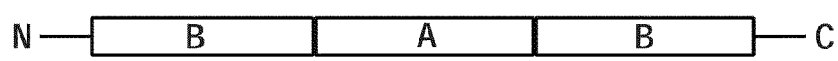

FIG. 3C shows a schematic representation of a generic peptide hydrogel network (black lines) in which some of the peptides are modified to include bioactive peptide motifs (red lines) extending from the amino termini of the base peptide. Close up: stacked self-assembling peptide nanofiber (black lines) and the extended sequence of the bioactive peptide motif at the amino termini of one of the sequences (red line).

V. Amino Acid Domains for Use in Modified Self-Assembling Peptides

In general, any of a wide variety of different amino acid domains may be added to the unmodified self-assembling peptides, provided that the presence of the additional domain does not prevent self-assembly (to form nanofibers, a macroscopic structure, or, preferably, both). The additional domains may confer any of a number of desirable properties on the resulting peptides. For example, the additional domain may mediate a biological activity, e.g., may affect the behavior of cells contacted with a scaffold made by self-assembly of the peptides. The additional domain may bind to either a naturally occurring or artificial biomolecule, such as an ECM protein, cell-surface molecule, antibody, etc. The additional domain may bind to an inorganic substance such as a metal, ion, etc.

The presence of the additional domain may alter the material properties (e.g., strength, elasticity, etc.) of a macroscopic structure created by self-assembly of the peptide, relative to the properties of a macroscopic structure created by self-assembly of the unmodified peptide. Thus by modifying a self-assembling peptide to include a non self-assembling domain, the material properties of a macroscopic structure can be tuned according to the needs of the user. For example, for implantation into the body it may be desirable to employ materials with different material properties, depending on the site of implantation and/or the tissue that the implant is to replace (e.g., bone, connective tissue, soft tissue such as muscle, ocular tissue, solid organ tissue, etc.). The following sections provide a non-limiting description of exemplary amino acid domains that can be added to an unmodified self-assembling peptide and methods for their selection.

A. Biologically active peptide motifs

Efforts to modify the previously identified self-assembling peptides were inspired in part by a desire to create a fully synthetic material that would recreate important features of the microenvironment provided by the cellular basement membrane. The cellular basement membrane is a three-dimensional network mainly composed primarily of laminins, collagens and proteoglycans. Basement membranes underlie sheets and tubes of epithelial cells and also surround individual cells of various types such as muscle cells, fat cells, and Schwann cells. In certain locations (e.g., lung, kidney glomerulus) the basement membrane separates sheets of cells and serves as a filter. Under electron microscopic visualization, basement membranes can be seen to include two distinct layers: an electron-lucent layer adjacent to the basal plasma membrane of cells resting on the basement membrane and an electron-dense layer below. Basement membranes may also include a third layer that connects the lower layer to underlying connective tissue (Alberts, et al., referenced above).

In addition to its importance as a structural component, supporting cell attachment and acting as a barrier that separates various cells, tissues, and organs, it also provides cells with an instructive microenvironment that interacts with them and modulates their function. Cell polarity, metabolism, differentiation, and migration are among the aspects of cell function modulated by the basement membrane. In addition, molecules in the basement membrane can contribute to the structural organization of plasma membrane and intracellular molecules. Basement membrane molecules also interact with one another.

The role of the ECM in modulating cell function is of particular interest in the context of the vascular system, in which vessels and heart chambers contain an inner endothelial cell monolayer resting atop a basement membrane that separates the endothelial cells from muscular layers below. The basement membrane is believed to play an important role in processes such as vascularization, and its integrity is important in maintaining proper vascular function. Damage or alterations in the endothelial cell layer and/or underlying basement membrane are likely to play a key role in various disease processes such as atherosclerosis.

Short peptide sequences present in proteins of the basement membrane have been identified as participating in a variety of important biological functions including cell attachment, proliferation, differentiation and migration (Iwamoto et. al., 1987, Kleinman et. al., 1989, Koliakos et. al., 1989, Skubitz et. al. 1990, Tsilibary et. al., 1990, Sakamoto et. al., 1991). Peptide sequences that mediate binding between different ECM molecules or binding between ECM molecules and non-ECM molecules in the body have also been identified. The following sections describe features of various basement membrane molecules that may contain and/or interact with such peptide motifs and provide further details regarding relevant aspects of the vascular system, endothelial cells, and the endothelial basement membrane.

Laminin-1. Laminins represent a protein family of heterotrimers containing α, β and γ chains. Laminins are primarily located in basement membranes but also in mesenchymal compartments. Laminins create physical boundaries between stromal matrix and epithelial, endothelial, muscle, and nerve cells. So far at least 11 laminin isoforms (containing various combinations of α, β and γ chains have been identified. Common to all of them is a coiled-coil domain which plays a key role in heterotrimer assembly. Laminin-1 is the earliest laminin produced during mouse development prior to the blastocyst stage, contributing to epithelial tissues during organogenesis (Dziadek & Timpl, 1985; Klein et al., 1990). Laminin-1 ($M_r$=900,000) is formed from α1, β1 and γ1 subunits, which assemble into a cross-like structure (Engel et al., 1981). It forms a complex with nidogen, resulting in networks with a quasi-hexagonal pattern and three-dimensional structures. Formation of the complex occurs in a calcium, temperature, and concentration manner (Yurchenco & Cheng, 1993).

Laminin-1 is involved in a number of important interactions including both homotypic interactions or between different isoforms. It also interacts with other proteins of the extracellular matrix forming bridges between the protein complex and cell membranes through cell-membrane receptors, or directly interacting with cells through several integrin and non-integrin receptors (Kreis & Vale, 1999). Major biological functions attributed to laminin-1 include promoting cell adhesion, cell migration, cell differentiation and proliferation, enhancing neurite outgrowth, regulation of cell shape, and establishment of cell polarity of a variety of cell types (Martin & Timpl, 1987, Timpl, 1980, Beck et. al., 1990; Engel, 1992).

The different biological activities of laminin-1 have been characterized using proteolytic fragments, recombinant fragments or subunits, and short synthetic peptides (Yamada & Kleinman, 1992, Yamada, 1991, Table 2). For instance, the sequence AASIKVAVSADR (SEQ ID NO: 31) derived from the laminin a chain promoted activity of neurite extension by PC12 cells (Yasumitsu et. al., 2002). In addition, the peptide CSRARKQAASIKVAVSADR (SEQ ID NO:32), which includes this sequence (underlined) induced degradation of Matrigel matrix by human umbilical vein endothelial cells (HUVEC) and zymogram analysis demonstrated collagenase IV activity, a key enzyme in basement membrane remodeling and/or degradation (Grant et. al., 1992).

The sequences YIGSR (SEQ ID NO:33), PDSGR (SEQ ID NO: 34), RYVVLPR (SEQ ID NO:35) located on the β1 chain promoted cell adhesion and, in addition, YIGSR (SEQ ID NO:33) promoted cell migration and human umbilical vein endothelial cell (HUVEC) tube formation (Iwamoto et. al., 1987, Sakamoto et. al., 1991, Kleinman et. al., 1989; Skubitz et al., 1990, Grant et. al., 1989). The sequence KAFDITYVRLKF (SEQ ID NO:36) from the laminin γ1 chain also promoted HUVEC adhesion and tube formation, as well as neuronal cell adhesion and neurite outgrowth, suggesting that laminin-1 may interact specifically with various cellular receptors through different domains (Nomizu et. al., 1997, Ponce et. al., 1999).

Collagen IV. Collagenous proteins constitute a superfamily of extracellular matrix proteins with a structural role as their primary function. All collagens have domains with a triple helical conformation. Such domains are formed by three subunits (α chains), each containing a (Gly-X—Y)$_n$ repetitive sequence motif.

Collagen IV is the major collagenous component of the basement membrane, forming a network structure that involve the interaction with other basement membrane components including laminin, nidogen, and heparan sulfate proteoglycan (Kreis & Vale, 1999). Collagen molecules are composed of two α1(IV) chains and one α2(IV) chain. Collagen IV is believed to interact with cells indirectly through laminin via direct low affinity interactions (Yurchenco & O'Rear, 1994, Charonis et. al., 1985) or by strong binding mediated by nidogen, a glycoprotein of about 150 Kda, which binds tightly to laminin (Paulsson et. al., 1987, Poschl et. al., 1996) and has binding sites also for collagen IV (Timpl, 1996). Type N collagen also binds to heparin and heparan sulfate proteoglycan (Yurchenco & O'Rear, 1994, Tsilibary et. al., 1988, Koliakos et. al., 1989, Fujiwata et. al., 1984).

Many cell types adhere to type N collagen, and peptide sequences within it have specific biological activities. For instance the peptide TAGSCLRKFSTM (SEQ ID NO:37) was found to specifically bind to heparin and intact type N collagen in a dose dependent manner (Koliakos et. al., 1989, Tsilibary et. al., 1990) and, in addition, the same peptide also was able to promote the adhesion and spreading of bovine aortic endothelial cells (Tsilibary et. al., 1990). The peptide sequence also inhibited collagen N matrix assembly when both were incubated together in solution. Thus, the role of this type N collagen derived peptide sequence is diverse, influencing matrix assembly, heparin binding and cell adhesion (Tsilibary et. al., 1990).

Nidogen. Nidogen (previously referred to in the literature as entactin) consists of a single polypeptide chain that binds to the laminin-1 γ chain by a single module (LE) of 56 residues (Poschl et. al., 1996). Nidogen also interacts with collagen type N via a separate epitope and it is considered to act as a linker molecule between laminin-1 and collagen IV in basement membranes. In addition, nidogen contains RGD sequences which may serve as cell attachment sites via integrin molecules (Timpl, 1989).

Proteoglycans. Proteoglycans are a set of proteins found in a variety of locations including cell surfaces, within intracellular vesicles, and incorporated into extracellular matrices. They are defined and classified by the presence of a common post-translational modification, a special type of polysaccharides, the family of glycosaminoglycans. Proteoglycans are a diverse set of macromolecules composed of a core protein which can consist of a small or large polypeptide chain (10-400 kDa) carrying from one to hundreds of glycosaminoglycan chains. There are many known activities of proteoglycans. Among those, they are known to regulate cell-cell and cell-matrix interactions by binding with other extracellular matrix proteins. They regulate extracellular matrix assembly and structure and they immobilize diffusible molecules within the extracellular matrix as storing and releasing compartments (Kreis & Vale, 1999).

Additional basement membrane components. In addition to the proteins described above, a number of other proteins are present in the basement membrane and play significant roles. Among them are perlecan, agrin, BM-40/SPARC, fibulin-1, fibulin-2 (Timpl 1996, and references therein). A number of proteins related to these have also been discovered.

Vascular system and the ECM. Vascular endothelial cells provide an interface between the systemic circulation and soft tissues and participate in critical processes including inflammation, coagulation and hemostasis. Vascular endothelium also plays a role in a diverse set of pathological conditions ranging from atherosclerosis to diabetic nephropathy. Extension of pre-existing blood vessels and/or generation of new blood vessels from existing vasculature (angiogenesis) plays an essential role in tissue repair and regeneration as well as in embryonic development. In general, these processes involve the formation of a three-dimensional vascular network that provides nutrients and oxygen and removes waste products from the cells. Angiogenesis has been the subject of intensive research efforts during the past two decades (Carmeliet, 2000, Han & Liu, 1999).

The generation of vascularised three-dimensional structures is today one of the major challenges in tissue engineering (Eiselt et. al., 1998). Cells can stay alive by diffusion of nutrients only when they are located within ~100-200 μm of a blood supply (Colton, 1995). It would be desirable to develop methods of creating artificial vascular networks for use in tissue engineering applications that go beyond thin structures such as skin in which nutrients and oxygen can be delivered by diffusion (Cassell et. al., 2002), or avascular tissues such as cartilage.

Figure 8:
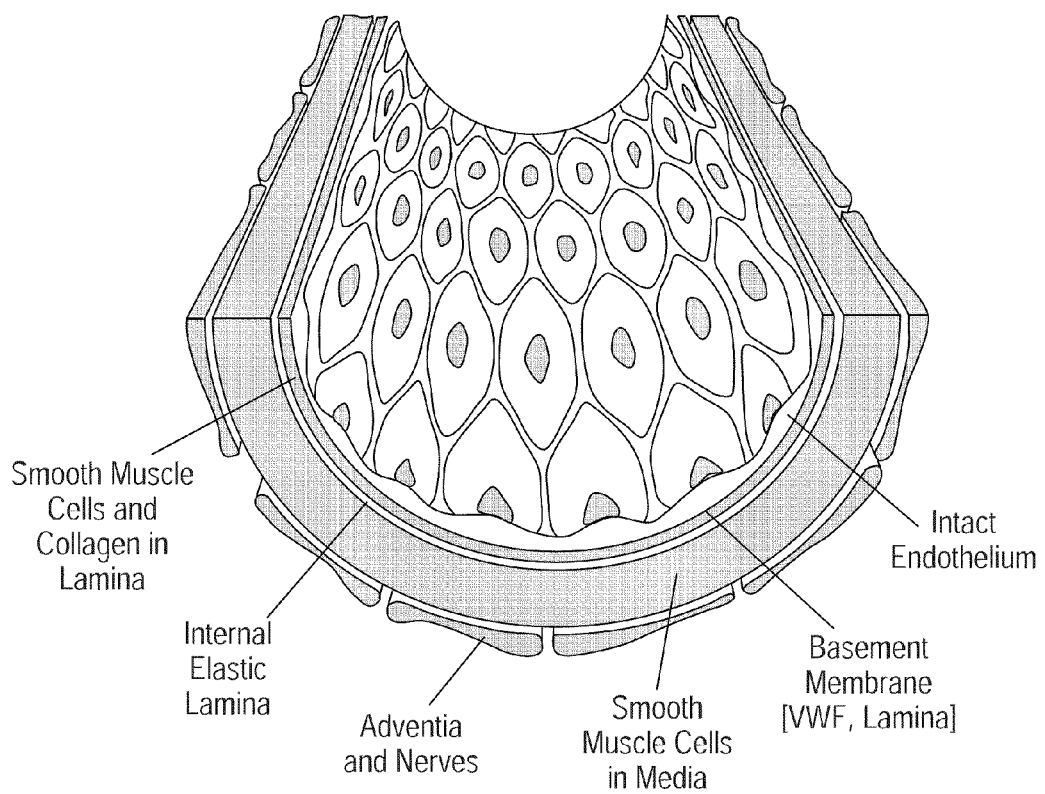
FIG. 8 shows a simplified schematic diagram of the structure of a blood vessel.
Figure 9:
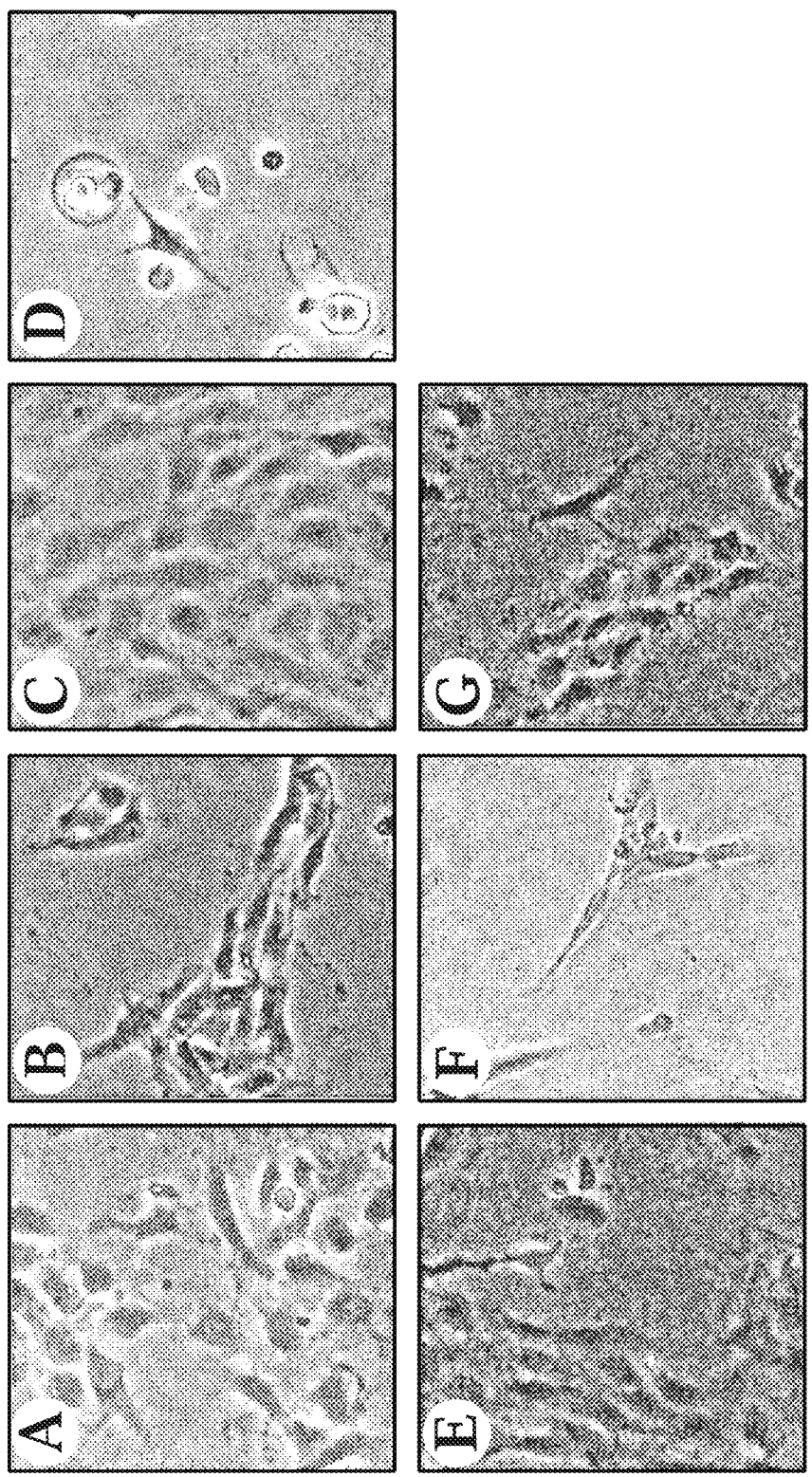
FIGS. 9A-9G show phase contrast microscopy images of human aortic endothelial cells (HAEC) on (A) RAD16-I; (B) AAS; (C) YIG; (D) PDS; (E) RYV; (F) KAF; (G) TAG. All peptides are at 100% (no blending).
Figure 10:
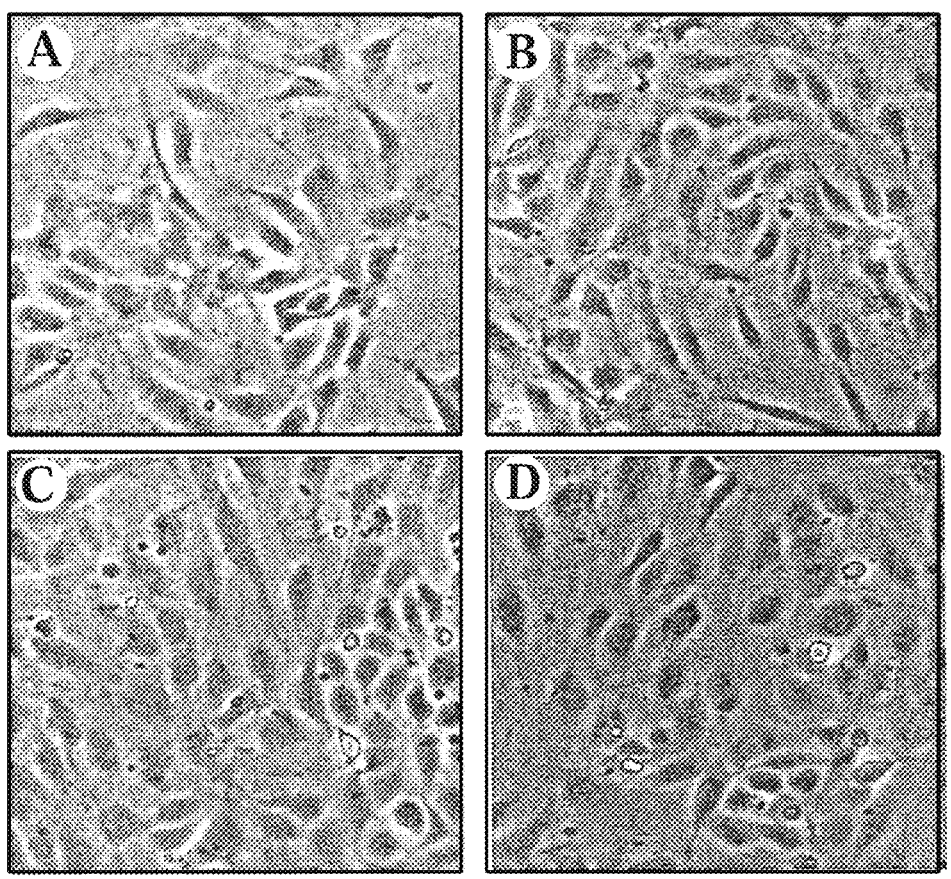
FIGS. 10A-10D show phase contrast microscopy images of HAEC monolayer formation on (A) RAD16-I; and blending 9:1 of (B) YIG; (C) RYV; (D) TAG.
Figure 11:
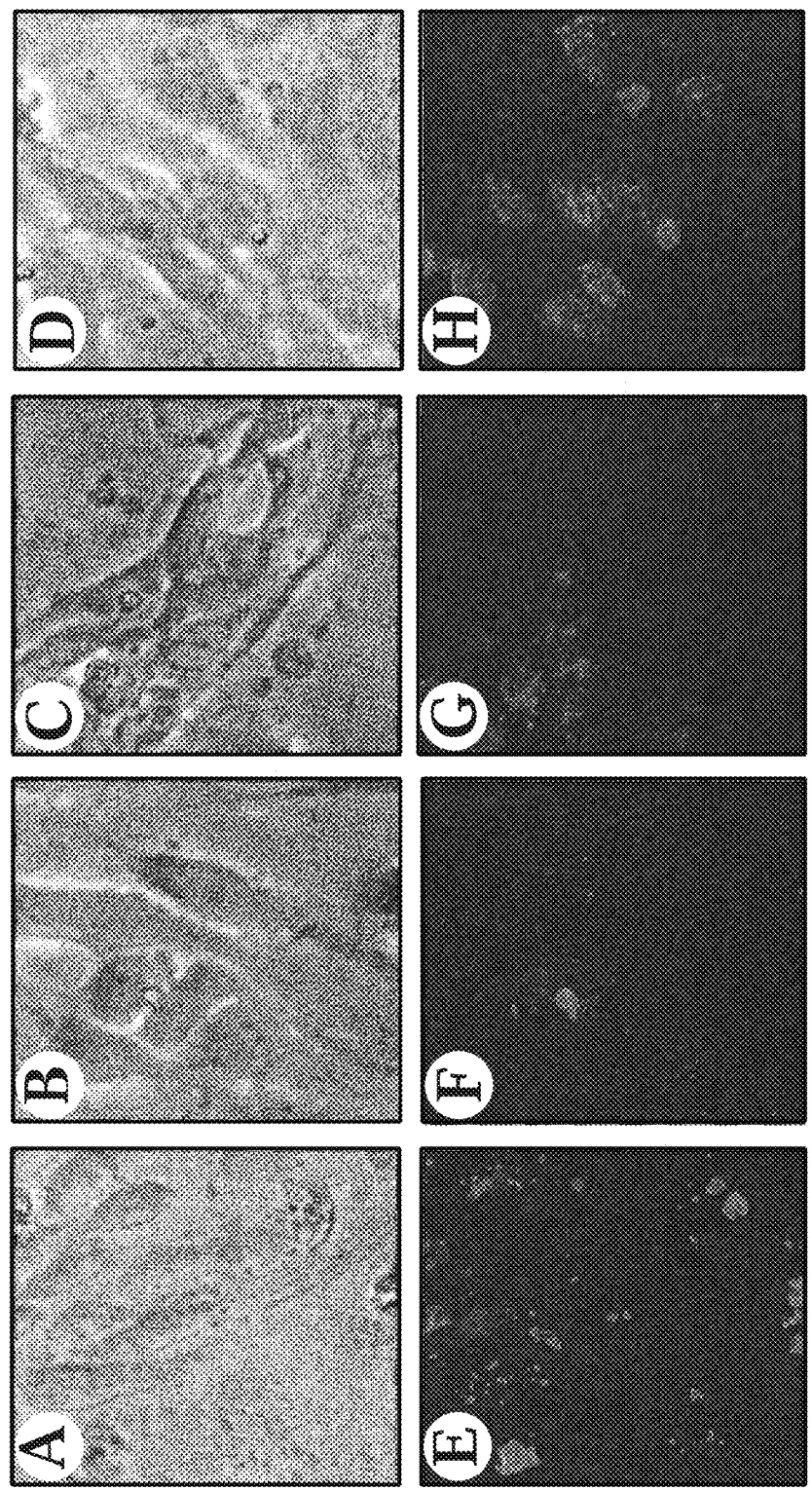
FIGS. 11A-11H show phase contrast microscopy images of HAEC seeded on peptide scaffolds (A) RAD16-I; (B) YIG; (C) RYV; (D) TAG, and fluorescent staining with Di-Ac-LDL (red, indicative of LDL uptake) and DAPI nuclear staining (blue) for (E) RAD16-I; (F) YIG; (G) RYV; (H) TAG. Each image in the lower panel represents the same field of cells as the corresponding image directly above. RAD16-I was present at 100%; the other peptide scaffolds were formed from a 9:1 blend of RAD16-I:modified peptide.

The general structure of a blood vessel comprises an inner lining of flattened endothelial cells with a cobblestone morphology forming a cell monolayer that is separated from the underlying smooth muscle cells by a thin extracellular matrix, the basement membrane (FIG. 8). Endothelial cells possess a negative outer charge that repels platelet adherence, produce glycosaminoglycans that bind antithrombin III, as well as tissue plasminogen activator, which facilitate the anticoagulant and fibrinolytic activities of endothelial cells. In common with most other basement membranes, the basement membrane of blood vessels is mainly composed of laminin-1, collagen IV, nidogen, and proteoglycans. It is well established that the behavior of endothelial cells is influenced by interaction with the basement membrane (Tsilibary et. al., 1988, Tashiro et. al., 1989, Grant et. al., 1989, Skubitz et. al., 1990, Sakamoto et. al., 1991, Kanemoto et. al., 1990, Grant et. al., 1990, Nomizu, et. al., 1997, Ponce et. al., 1999, Malinda et. al., 1999).

Endothelial cell function. The endothelial monolayer has multiple functions including facilitating blood flow by providing a nonthrombogenic surface, being a permeable barrier and transport interface for metabolites, modulating the inflammatory response, modulating the contractility of the vascular smooth muscle and the myocardium, and regulating vascular tone and homeostasis, among others (Boeynaems & Pirroton, 1994, Cines et. al., 1998).

Endothelial cells continuously produce, secrete, and remodel their own basement membrane and also synthesize vasoactive autacoids (from Greek autos-self and akos-remedy), that contribute to regulate vascular tone and homeostasis (Busse & Fleming, 2003). Nitric oxide (NO) is one of the best known vasodilators. In biological systems, NO is synthesized from L-arginine by the action of nitric oxide synthase being the other reaction product L-citrulline. Another potent vasodilator and inhibitor of platelet aggregation is prostacyclin (or also called prostaglandin $I_2$, $PGI_2$). $PGI_2$ belongs to the family of eicosanoids, and it is formed from arachidonic acid via prostaglandin $H_2$ ($PGH_2$) by prostacyclin synthetase. A 21 aminoacid peptide, endothelin-1 (ET-1) has been shown to promote vasoconstriction. These three substances (and likely others as well) act together as regulators of vessel tone.

It is known that the lack of a healthy endothelium can contribute to major vascular pathologies such as thrombosis. For example, disruption of the smooth endothelial monolayer may occur due to the deposition of lipids and other materials found in atherosclerotic plaques and/or may contribute to the development of atherosclerotic lesions (Cines, et al., 1998). The presence of a confluent monolayer of endothelial cells could improve thromboresistance. It may also prevent or ameliorate other diseases such as pseudointimal hyperplasia, e.g., by preventing the adhesion of platelets, which release bioactive factors that can contribute to smooth muscle recruitment and/or proliferation. In addition, the ability to generate a smooth endothelial monolayer would be useful to restore the integrity of the endothelium following invasive procedures such as angioplasty, catheterization, etc. Therefore, considerable efforts are currently directed to the study of endothelization, both in vitro and in vivo.

A number of researchers have studied the role of extracellular matrix in vascularization. Many such studies involved observation of EC behavior on extracellular matrix derived materials such as Matrigel, a basement membrane derived material obtained from the Engelbreth-Holm-Swarm mouse tumor, or collagen (Grant et. al., 1989, Davis et. al., 2000, Bell et. al., 2001, Davis et. al., 2002). Angiogenic processes such as tube formation have been studied in both 2D and 3D systems (Davis et. al., 2000, Bell et. al., 2001, Davis et. al., 2002). The interaction of EC with several synthetic peptides (Grant et. al., 1989, Grant et. al., 1992, Ponce et. al., 1999, Nomizu et. al., 2001) has been explored.

It has been previously shown that seeding EC cells in environments that mimic physiological conditions existing in vivo can stimulate the production of various vasodilator and vasoconstrictor substances such as those described above (Gloe et. al., 1999, Busse & Fleming, 2003) and/or enhance various angiogenic processes such as tube formation, e.g., relative to the situation when EC cells are seeded on conventional substrates. As mentioned above, scaffolds formed by self-assembly of unmodified peptides provide an environment that replicates an in vivo environment in a number of respects. The inventors hypothesized that modification of the self-assembling peptides to incorporate biologically active peptide motifs may enhance their ability to act as basement membrane analogs, which mimic the extracellular microenvironment of EC.

As described in the examples, the inventors created a variety of modified peptides and tested their ability to assemble into macroscopic structures that could be used for purposes such as cell culture, tissue engineering, or therapeutic applications either with or without cells. Surprisingly, it was found that extensive modifications may be made without preventing scaffold formation. The inventors tested the capability of these new biomimetic materials to support monolayer formation, growth, and function of human aortic endothelial cells (HAEC). The addition of a number of the peptide motifs conferred new biological activities on the peptides as evidenced by alteration in HAEC behavior when cultured in the presence of scaffolds made from the modified peptides (Example 2). It was discovered that altering the effective concentration of peptide motifs presented to cells by the scaffolds alters the effects on cells. For the peptides tested, composite scaffolds in which only a portion of the self-assembling peptides incorporate the biologically active peptide motif appears to be preferable in terms of enhancing functional activity of the cells.

Figure 16:
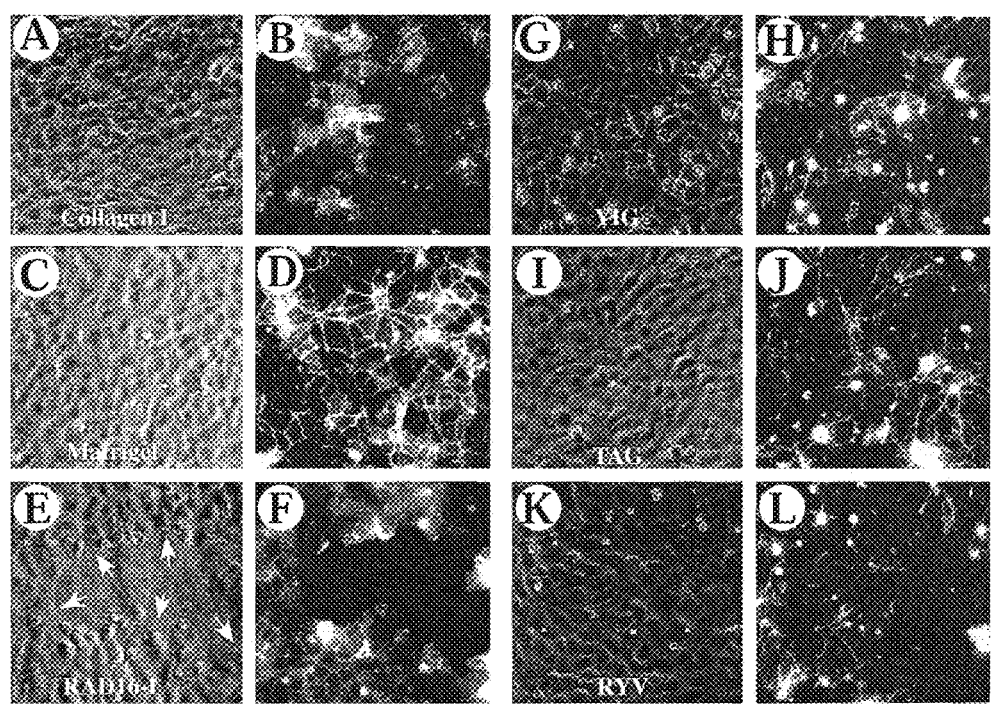
FIGS. 16A-16L shows a comparison of monolayer formation of Human Aortic Endothelial Cells (HAEC) cultured on different gel systems. Phase contrast microscopy images of HAEC seeded on Collagen I gel (A), Matrigel (C), 100% peptide scaffold RAD16-I (E), blending 90% RAD16-I/10% (v/v) YIG (G), blending of 90% RAD16-I/10% (v/v) TAG {1), and blending of 90% RAD16-I/10% (v/v)RYV (J). Fluorescent staining with TRITC Phalloidin and DAPI to detect Actin fibers and nucleus, respectively, for A (B), C (D), E (F), G (H), I {J), K (L). Phase contrast images depict a typical cobblestone monolayer also observed with the actin/DAPI staining.

The inventors discovered that scaffolds comprising the modified self-assembling peptides YIG, RYV, or TAG (blended with unmodified peptide RAD16-I as described in Example 2) supported increased monolayer formation relative to monolayer formation on scaffolds made of unmodified peptides, while also supporting NO release and synthesis of basement membrane components (laminin 1 and collagen IV) to a greater extent than occurs when HAEC are cultured on conventional plastic substrates. Cell growth and morphology on unmodified or modified peptide scaffolds was also compared with cell growth and morphology when cells were cultured on materials obtained from natural extracellular matrix materials, i.e., Matrigel (Matrigel™; Becton Dickinson) or collagen I-coated surfaces (Example 2). Qualitatively, monolayer formation, morphology, and cell number appeared similar on the modified peptide scaffolds to the appearance on Matrigel or collagen-1. HAEC attained confluence and exhibited a typical cobblestone morphology (FIG. 16). In contrast, HAEC grown on a scaffold made of unmodified peptide (RAD16-I) did not attain confluence, exhibiting large gaps in the monolayer (FIG. 16).

Figure 17:
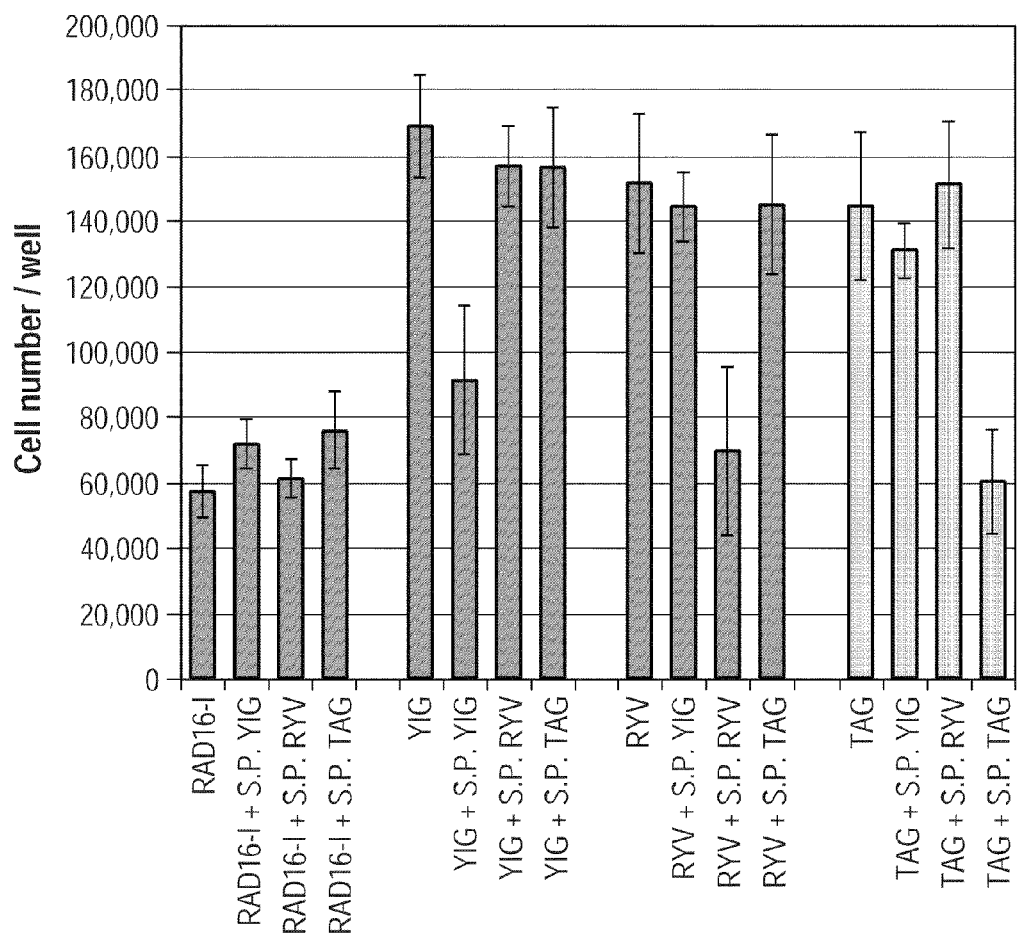
FIG. 17 presents bar graphs showing results of competition assays measuring HAEC growth on various peptide scaffolds with soluble peptide (S.P.) motifs. Cells were cultured for three days on different peptide scaffold compositions in presence or absence of soluble peptide (S.P.) motifs: RAD16-1, 100% of control peptide scaffold; RAD16-I+S.P.YIG, control peptide scaffold with soluble peptide motif YIGSR (SEQ ID NO:33) (400 µM); RAD16-I+S.P.RYV, control peptide scaffold with soluble peptide motif RYVVLPR (SEQ ID NO:35) (400 µM); RAD16-I+S.P.TAG, control peptide scaffold with soluble peptide motif TAGSCLRKFSTM (SEQ ID NO:37) (400 µM); YIG, blending of 90% of RAD16-I/10% YIG peptide (v/v); YIG+S.P.YIG, YIG peptide scaffold with soluble peptide motif YIGSR (SEQ ID NO:33) (400 µM); YIG+S.P.RYV, YIG peptide scaffold with soluble peptide motif RYVVLPR (SEQ ID NO:35) (400 µM); YIG+S.P.TAG, YIG peptide scaffold with soluble peptide motif TAGSCLRKFSTM (SEQ ID NO:37) (400 µM); RYV, blending of 90% of RAD16-I/10% RYV peptide (v/v); RYV+S.P.YIG, RYV peptide scaffold with soluble peptide motif YIGSR (SEQ ID NO:33) (400 µM); RYV+S.P.RYV, RYV peptide scaffold with soluble peptide motif RYVVLPR (SEQ ID NO:35) (400 µM); RYV+S.P.TAG, YIG peptide scaffold with soluble peptide motif TAGSCLRKFSTM (SEQ ID NO:37) (400 µM); TAG, blending of 90% of RAD16-I/10% TAG peptide (v/v); TAG+S.P.YIG, TAG peptide scaffold with soluble peptide motif YIGSR (SEQ ID NO:33) (400 µM); TAG+S.P.RYV, TAG peptide scaffold with soluble peptide motif RYVVLPR (SEQ ID NO:35) (400 µM); TAG+S.P.TAG, TAG peptide scaffold with soluble peptide motif TAGSCLRKFSTM (SEQ ID NO:37) (400 µM).

Furthermore, it was discovered that competition with soluble peptide motif reduced the proliferation rate to similar levels to those observed on the scaffold made from unmodified RAD16-I peptide, suggesting that the presentation of the peptide motif by the culture substrate is significant. As shown in the bar graphs in FIG. 17 (see Example 2), in the absence of added soluble biologically active peptide, HAEC proliferation on peptide scaffolds made from 100% RAD164 peptide is significantly lower, by about 2-2.5 fold, than proliferation on scaffolds made from peptide blends. Adding a soluble biologically active peptide to cultures grown on a scaffold containing that peptide reduces HAEC proliferation to approximately the same level as on unmodified RAD16-I scaffolds. Importantly, the data also indicates that when HAEC are cultured on a scaffold containing peptides with a specific biologically active amino acid domain, the competition only reduces cell proliferation when the same amino acid domain is provided in soluble form, in other words, by competing with the same sequence tag on the nanofibers comprising the scaffold.

Table 2 presents a non-limiting list of various peptide motifs that have been shown to have biological activities in various systems, together with the protein in which the motif naturally occurs, and the biological activity observed. Any of these peptide motifs can be used as the second amino acid domain for modification of a self-assembling peptide. Certain of these peptide motifs contain subsequences that are believed to be the active domain (e.g., IKVAV (SEQ ID NO:48) is contained in the first two peptides listed), which may be used. It is to be understood that any of these motifs, or others, should be tested by actually synthesizing the modified peptide and testing its ability to self-assemble, e.g., to form sheets, nanofibers, and/or a macroscopic structure, preferably a gel, under conditions that would result in self-assembly of an unmodified peptide. Methods for performing such tests are described below, and the tests themselves require no more than routine experimentation. Thus the teachings provided herein, showing that a diverse set of amino acid domains can be added to the previously described self-assembling peptides without preventing self-assembly, supports the identification of numerous other suitable amino acid domains. The invention thus provides a method of selecting a self-assembling peptide comprising (a) modifying a self-assembling peptide comprising a first amino acid domain that mediates self-assembly, wherein the domain comprises alternating hydrophobic and hydrophilic amino acids that are complementary and structurally compatible and self-assemble into a macroscopic structure when present in unmodified form by adding a second amino acid domain that does not self-assemble in isolated form; and (b) testing the resulting peptide to determine whether it self-assembles. Testing can be carried out under conditions suitable for self-assembly of unmodified self-assembling peptides. Preferably modified peptides that self-assemble into β sheets, nanofibers, and/or macroscopic structures are selected.

TABLE 2

Peptide sequences from basement membrane proteins and their biological activities.

| Peptide sequence | Protein | Biological activity |
|---|---|---|
| AASIKVAVSADR (SEQ ID NO: 31) | Laminin-1 | Neurite extension in PC12 cells |
| CSRARKQAASIKVAVSADR (SEQ ID NO: 32) | Laminin-1 | Degradation of Matrigel matrix, endothelial mobilization, capillary branching, vessel formation (in vivo) |
| YIGSR (SEQ ID NO: 33) | Laminin-1 | Cell adhesion, cell migration, endothelial tubular formation |
| PDGSR (SEQ ID NO: 34) | Laminin-1 | Cell adhesion |
| RYVVLPR (SEQ ID NO: 35) | Laminin-1 | Cell adhesion |
| KAFDITYVRLKF (SEQ ID NO: 36) | Laminin-1 | Endothelial cell adhesion and tubular formation, neurite outgrowth |
| TAGSCLRKFSTM (SEQ ID NO: 37) | Collagen-IV | Binds to heparin and heparan sulphate, promotes adhesion and spreading of bovine aortic endothelial cells |

Any of a wide variety of additional peptide motifs in addition to those listed in Table 2 can be used as biologically active peptide motifs to modify the unmodified self-assembling peptides. The motifs may be derived from any of a diverse range of naturally occurring proteins and peptides including ECM components, cell adhesion molecules, cell surface receptors, growth factors, cytokines, chemokines, etc. The RGD sequence is a prototypic cell recognition sequence found in fibronectin and well known to be recognized by integrins and to mediate cell attachment. LDV is another such motif.

A large number of additional biologically active peptides have been identified as described in the various references cited herein. For example, RNIAEIIKDI (SEQ ID NO:49) is an active peptide also derived from laminin-1 (γ chain) (Liesi, P., Narvanen, A., Soos, J., Sariola, H. and Snounou, G., (1989) FEBS Letters, 244:141-148). Biologically active peptide motifs that mediate cell binding, including peptides comprising the sequences YVRL (SEQ ID NO:50), IRVTLN (SEQ ID NO: 51), TTVKYIFR (SEQ ID NO:52), and SIKIRGTY (SEQ ID NO: 53) have been identified by systematic screening of synthetic peptides derived from the sequence of the mouse laminin γ1 chain (Nomizu 1997). A number of biologically active peptide domains have been identified in the N-terminal domain of various laminin α chains, for example RQVFQVAYIIIKA (SEQ ID NO: 54), FQIAYVIVKA (SEQ ID NO:55), GQLFHVAYIIIKA (SEQ ID NO:56), FHVAYV-LIKA (SEQ ID NO:57), and LENGEIVSLVNGR (SEQ ID NO:58) (Nomizu, et al., 2001).

HAV is derived from the cell adhesion protein N-cadherin and has been shown to mediate interaction between axons and associated glial cells (Schense, J C and Hubbell J A (1999), *Bioconjugate Chemistry*, 10:75-81). REDV (SEQ ED NO:59) is an adhesion ligand from fibronectin that is believed to be specific for the endothelial cell integrin receptor α4β1, which is present on endothelial cells but not on platelets (Hubbell, J A., Massia, S. P., Desai, N P, Drumheller P D (1991) Biotechnology 9:568-72)). LGTIPG (SEQ ID NO:60) and DGEA (SEQ ID NO:61) represent additional sequences known to mediate cell adhesion (Yamada 1991). GVGVP (SEQ ID NO:62 is a domain that is found in repeated form in elastin and may mediate cell adhesion. GVGVAP (SEQ ID NO:63) is a chemoattractant that attracts monocytes. It is noted that biologically active peptide domains may be identified in the version of a protein found in a particular species, e.g., human, mouse, rat, but may display biological activity with respect to cells of other species as well and can be tested using cells of various cell types and species. A large number of peptides derived from laminin α1, β1, or γ1 chains that were active in assays of HUVEC attachment and/or tube formation have been identified (Malinda 1999; Ponce 1999).

Candidate peptides for use as biologically active peptide motifs may be tested for their ability to affect any of a number of cellular processes when incorporated into a peptide scaffold of the present invention. Certain useful tests are described below. Altered versions of the candidate peptides can also be used to modify the unmodified self-assembling peptides, and scaffolds comprising these altered candidate peptides can be used as a control. A range of different peptide concentrations can be tested, and various combinations can be used.

A peptide can be identified as a biologically active peptide motif according to a number of criteria including, but not limited to, those described by Yamada (1991). While Yamada describes tests for biological relevance for the case of adhesive recognition sequences, the criteria he gives may be applied more widely. A putative active peptide motif may be identified as biologically relevant is a synthetic peptide containing the sequence displays activity after conjugation to a carrier (e.g., IgG, albumin, beads), even if inactive when adsorbed directly on a substrate such as glass, plastic, etc., though they may also display activity when conjugated to a substrate. A soluble form of a biologically active peptide motif may competitively inhibit the function of an intact protein in which the motif is naturally found. Alteration of the peptide sequence may eliminate the function of the peptide. For example, site-directed mutagenesis of a protein in which the peptide is naturally found, or amino acid substitution in a synthetic peptide may cause loss of biological activity. Anti-peptide antibodies may eliminate function of the protein in which the motif is naturally found. A biologically active peptide may bind to the same cellular receptor or naturally occurring biomolecule as a naturally occurring protein containing the peptide.

In addition to amino acid domains whose sequence is derived from naturally occurring proteins such as those mentioned above, amino acid domains from growth factors, cytokines, chemokines, peptide hormones, peptide neurotransmitters, other biologically active peptides found in the body, etc., can also be used. See Goodman and Gilman 2001, referenced above, and Kandel 2000, referenced above, for examples.

B. Tests for Biological Activity

This section describes a variety of tests that can be used to determine whether a candidate peptide comprises or consists of a biologically active peptide motif. The tests described below are provided for exemplary purposes only, and one of ordinary skill in the art will be able to select and employ a variety of additional tests and variations of the tests described herein, depending on the cell type and cell behavior of interest. In any of these tests, soluble peptide can be used as a control. A range of peptide concentrations (both substrate-bound, present as part of a modified self-assembling peptide, or in soluble form) may be used.

Also, it may be desirable to assess and/or monitor any of a variety of indicators of cell phenotype, cell viability or proliferation, cell phenotype, and/or the functional state of the cells or various cellular behaviors. As is well known in the art, there are a number of methods for assessing cell viability, proliferation, and for assessing various aspects of cell behavior and phenotype. In general, any appropriate method may be employed to investigate and assess the effects of culturing cells under the conditions described herein. In addition, the effects of the cells on the overall composition and properties of a cell/hydrogel assembly may be monitored. Such features as protein content, strength, etc., can be examined.

Cell viability and proliferation. Cell viability may be assessed by examining vital dye exclusion (e.g., trypan blue exclusion). Cell division may be observed by light microscopy and is indicated by the presence of mitotic figures. An increase in cell number accompanying division may also be observed, e.g., by counting with a hemacytometer. Morphological changes such as cell rounding may also accompany division. DNA synthesis may be monitored by detecting and/or measuring incorporation of various substances such as radiolabeled nucleotides (e.g., $^3$[H] thymidine), bromodeoxyuridine (BrdU), etc., into DNA. Numerous other assays are also available. For example, according to the MTS assay, when the MTS reagent (a tetrazolium salt) is applied to living cells, it is converted to a color compound (formazan) with the emission of light at 490 nm. Kits such as the LIVE/DEAD™ Viability/Cytotoxicity Assay Kit (Molecular Probes, catalog #L-3224) are widely available. Immunostaining using antibodies that bind to proteins indicative of cell proliferation such as proliferating cell nuclear antigen (PCNA) can also be used. Methods for assessing apoptosis are well known in the art and include visual examination, TUNEL, and determination of the level of mRNA or proteins associated with apoptosis, e.g., caspases.

Cell attachment. A convenient method to measure cell attachment promoting activity of a peptide is to conjugate the peptide to beads (e.g., sepharose beads) and incubate cells in the presence of the functionalized beads with or without added soluble peptide. Nonfunctionalized beads can be used as a control. Following incubation, cells can be detached using various methods such as treatment with an EDTA-containing solution, stained, and analyzed by microscopy, FACS, etc. (See Nomizu 2001 for further details). Similar methods can be used to test cell attachment to scaffolds comprising modified and/or unmodified self-assembling peptides (see Example 2).

Cell morphology and spreading. Cell spreading involves a number of morphological features that may differ depending on the cell type. For example, human foreskin fibroblasts typically assume an elongated polygonal cell shape (Hem and Hubbell, 1998) when spread and display an organized F-actin stress fiber network (see below). Cell morphology can be assessed by light microscopy, and the number of cells assuming a morphology characteristic of cell spreading on the modified versus unmodified scaffolds and/or in the presence or absence of competitor soluble peptide can be assessed.

Cytoskeletal organization. Certain peptides affect the organization of the cytoskeleton, which influences cell shape and migration. The organization of F-actin stress fibers within cells can be examined by staining with rhodamine-conjugated phalloidin (Hem and Hubbel, 1998). For example, cells cultured on a peptide scaffold can be fixed in 4% formaldehyde solution, permeabilized (e.g., with 0.1% Triton X-100 in PBS), incubated with rhodamine-conjugated phalloidin, and fixed again. They can then be visualized microscopically, e.g., using epifluorescence microscopy.

Cell migration. A number of assays are available to quantify cell migration on or through various substrates including scaffolds comprising the modified self-assembling peptides of the invention. For example, migration can be assessed using a fence-style assay in which cells are cultured on a substrate, e.g., a scaffold comprising modified self-assembling peptides, in the presence of a barrier. The location of the barrier is recorded. The barrier is then removed, and the cells are maintained for a period of time. The number of cells that cross the barrier in a given period of time is a measure of cell migration. Values can be corrected to account for cell proliferation, which may differ depending on the substrate. In a variation of the above approach, substrates comprising two or more different surfaces can be created by separating regions of a container by a barrier which is then removed. Differential migration onto various surfaces can be assessed. Migration can also be quantified using a radial Teflon fence migration assay as described for smooth muscle cells (Mann 2002) and human microvascular endothelial cells (FIMVEC) (Sagnella 2004).

Cell differentiation, dedifftrentiation, and transdifferentiation. These features can be assessed based on a number of parameters, including morphology. Cell differentiation, dedifferentiation, and transdifferentiation may also be assessed by detecting and/or measuring the presence of certain polypeptides or polynucleotides known as markers. The latter approach is widely used, and cellular markers characteristic of numerous different cell types have been identified. mRNA and/or protein expression may be detected by techniques well known in the art. For example, mRNA may be detected and quantified using Northern blots, cDNA or oligonucleotide microarray analysis, RT-PCR, etc. Protein expression may be detected and quantified using immunoblotting analysis, immunofluorescence, FACS analysis, ELISA assays, etc. Such immunological techniques may employ monoclonal or polyclonal antibodies that bind to the protein.

The variety of markers is immense, and new markers are routinely being identified. For example, nestin is an intermediate filament protein expressed in neuroepithelial neuronal precursor stem cells, and its expression decreases with neuronal maturation (Lendahl 1990). Nestin is considered a marker for immature neurons, and nestin-positive cells can differentiate into either neurons or glia. NeuN is a neuron-specific marker expressed in postmitotic cells (Sarnat 1998). Glial fibrillarary acidic protein (GFAP) is a classic glial astrocyte marker. Beta III tubulin is another neuron-specific protein. Expression of CYP450 proteins is characteristic of hepatocytes.

Of particular significance in the context of the present invention are markers that may be used to identify vascular endothelial cells and to evaluate functional activity of vascular endothelial cells. Von Willebrand factor is a widely recognized marker for vascular endothelial cells. Other markers for vascular endothelial cells include CD31, DC102, CD106, and isolectin B4 (Williams K S, 1995; "Microvascular endothelium from adipose tissue" *Endothelial Cell Culture*. Roy Bicknell (ed). Cambridge University Press, 1996). In certain embodiments of the invention the peptide scaffold desirably promotes angiogenesis. Markers of angiogenesis include angiogenesis-related growth factors VEGF, Angiopoietins 1 and 2, and their receptors Flt-1, Flk-1, Tie2 (Ferrara, 2001; Gale and Yancopoulos, 1999). Monoclonal antibodies directly conjugated with fluorescent dyes that bind to various of these markers are commercially available, e.g., from Dako, Chemicon, etc.

Functional assays can also be used to assess cell phenotype or state. For example, the ability of a cell to take up, produce, or secrete a certain molecule characteristic of a particular cell type, or to perform an enzymatic reaction characteristic of a particular cell type, can be assessed. As described in the Examples, uptake of low density lipoprotein (LDL) and release of NO are characteristic of endothelial cells.

ECM component production. It may be of particular interest to assess the effect of various candidate biologically active peptide motifs, active biomolecules, environmental parameters such as application of mechanical forces, etc., on production of ECM components and/or to monitor production of such components over time. A variety of methods for doing so are available. As described in Example 3, Western blots (or other immunological methods) can be used to quantify production of ECM proteins. For histological analysis, toluidine blue staining of glycosaminoclycan (GAG), a proteoglycan component, can be performed according to standard protocols. Collagen deposition can be measured using known techniques (Ioannidis et al., Cell Tissue Res. 297:141-147, 1999; Domm et al., Orthopäde 29:91-99, 2000). Extracellular protein production can be measured by addition of [$^3$H]-proline to the media. The radiolabeled proline is taken up by the cells and incorporated into newly synthesized proteins. Following a time period (e.g., 16-24 hours) in the radiolabeled media, free [$^3$H]-proline is removed by rinsing. The extracellular protein may be digested, e.g., by incubation in a proteinase K solution overnight at approximately 60° C., and the radioactivity present in the digested protein quantitated by scintillation counting. Proteoglycan production can be measured similarly, except that [$^{35}$S]-sulfate is added to the media instead of [$^3$H]-proline. The total accumulation of GAG can be measured based on fluorometric analysis of the amount of DMMB dye bound (Chandrasekhar et al., Analytical Biochemistry 161(1): 103-108, 1987).

Nervous system assays. There is considerable interest in developing materials that would be useful for in vitro culture of nervous system tissue (e.g., nerves, glial cells), repair and regeneration of nervous system tissue. Various parameters indicative of nervous tissue function can be measured. For example, neurite outgrowth can be assessed by microscopic examination (and, optionally digital image processing) of isolated cells cultured on top of peptide scaffolds, e.g., PC12 cells (Holmes, et al., 2000). Such cells can also be encapsulated. Another approach is to encapsulate dorsal root ganglia dissected from animals such as chicken and measure average neurite length extending from the ganglia at different time points (Schense and Hubbell 1999; Schense J C, Bloch J., Aebischer P., and Hubbell J A (2000) *Nature Biotechnology*, 18: 415-419). Synapse formation can be assessed as described, for example, in Holmes 2000. Production of neurotransmitters and enzymes known to be involved in neurotransmitter synthesis provide additional means of assessing nervous tissue functional activity.

Endothelial sprouting. An aortic ring assay, in which aortic rings are isolated from animals such as rats, cultured on top of peptide scaffolds for a period of time to allow sprouting, followed by fixing and microscopic examination can be used to quantify the ability of a candidate biologically active peptide to induce endothelial sprouting, an important aspect of angiogenesis (Malinda 1999).

Endothelial tube formation. Cell organization and formation of capillary-like structures following culture of ECs on the surface of or encapsulated within peptide scaffolds can be quantitated at various time points, e.g., 2 hr, 8 hr, 12 hr, 24 hr, 3 days, 1 week and 2 weeks after seeding by determining the correlation length as described in WO2003096972. Staining with hematoxylin and eosin, Massone's trichrome, as well as immunostaining for actin enables visual assessment of endothelial cell cluster formation, sprouting, capillary-like structure formation. The presence of a lumen in the capillary-like structures can be assessed visually and by using automated imaging systems including three-dimensional imaging systems. Methods for assessing tube formation are well known in the art (e.g., Davis et. al., 2000, Bell et. al., 2001, Davis et. al., 2002).

C. Biomolecule Interaction Motifs

In addition to biologically active peptide motifs that affect cell phenotype and/or function, a variety of other biologically relevant motifs, which may also affect cell function, are of use to modify the unmodified self-assembling peptides. In particular, it may be desirable to use a peptide motif that is known to bind to a naturally occurring protein, e.g., an ECM component such as those mentioned above (proteins, proteoglycans, GAGs, etc.). A number of peptides that mediate specific binding have been identified. For example, the peptides TAG-SCLRKFSTM (SEQ ID NO:37), LAGSCLSARFSTM (SEQ ID NO: 64), and GEFYDLRLKGDK (SEQ ID NO:65) are naturally found within collagen IV and were identified as specifically binding to heparin (Koliakos 1989). Others can be identified by systematic screening of synthetic peptides for binding activity, by two-hybrid screens, etc.

As an additional example, amino acid domains that comprise protease cleavage sites can be used. Such amino acid domains may also comprise a biologically active peptide motif, so that cleavage at the cleavage site releases the biologically active peptide. Cleavage can also alter the physical properties of a peptide scaffold which may, for example, alter the overall degradation rate and/or facilitate remodeling, cell migration, etc. In this regard it may be desirable to include an amino acid domain between two self-assembling domains in the modified peptide.

Protease cleavage sites that can serve as substrates for proteases commonly found in the ECM, which may be involved in ECM remodeling, cell migration, etc, are of particular interest. Examples are matrix metalloproteases (MMP) and members of the ADAM (a disintegrin and metalloprotease) family. The peptide GPQGIWGQ (SEQ ID NO:66) is a fast-degrading substrate for several members of the MMP family and is derived from the sequence GPQGIWGQ (SEQ ID NO:67) found in the α(1) chain of calf and chicken type I collagen (Nagase H., Fields G B, *Biopolymers* (1996), 40:339). Cleavage occurs between the adjacent G and I residues in both sequences. This motif provides an example of a situation in which alteration of a naturally occurring peptide motif is used to confer particular desired properties on an amino acid domain, in this case increasing the degradation rate. Additional cleavage sites for various MMPs and for elastase and various cathepsins (cathepsin L, B, K) have been identified (in the NC1 domain of human collagen XVIII α1 chain) (Ferreras, M, Felbor, U, Lenhard, T, Olsen, B R, and Delaisse, J-M, (2000) *FEBS Lett*. 486. 247-51). LIKMKP (SEQ ID NO:68) is a functional substrate for plasmin (cleavage occurs between K and M). Amino acid domains incorporating such cleavage sites or others known in the art can be used.

Additional biomolecule interaction motifs that may be used include binding sites for antibodies. The small amino acid domains used to modify the self-assembling portion of a peptide can serve as epitopes for the binding of a wide range of antibodies including therapeutic antibodies, labelled antibodies, etc. Such antibodies can be added to a peptide solution prior to self-assembly in vitro or prior to introducing the solution into the body for assembly in vivo. Alternately, the antibody can be an antibody that naturally occurs in a subject into which an inventive peptide scaffold is introduced or can be administered to such a subject. In the latter case, the antibodies may localize at the site of the scaffold, where they may be useful therapeutically and/or deliver a molecule, e.g., a therapeutic molecule at the site of the scaffold. Labelled antibodies may facilitate visualization of the scaffold, or monitoring of degradation products of the scaffold, etc.

D. Inorganic molecule binding domains

According to certain embodiments of the invention a amino acid domain that binds to an inorganic atom or molecule is used as the non self-assembling portion of an inventive self-assembling peptide. A number of such amino acid domains have been identified in naturally occurring proteins, and many others have been identified through various selection techniques such as phage display (see below). (Sarikaya 2004). A large number of other inorganic-binding peptides are known (Sarikaya 2004; Brown 1997; Whaley 2000, etc.). Peptides that bind to Au, Ag, Pt, Pd, $SiO_2$, ZnO, $Cu_2O$, zeolites, $CaCO_3$, $Cr_2O_3$, $FeO_3$, GaAs, ZnS have been identified. These compounds include heavy metals, semiconductors, and can even show selective binding to particular crystal structures and faces. Peptides incorporating these amino acid motifs may find wide use in nanotechnology, in areas such as nanoelectronics, nanophotonics, and nanomagnetics (Sarikaya 2004). Self-assembling peptides comprising such inorganic-binding peptides may be of particular utility as it is widely recognized that self-assembly is a fundamental principle in nanotechnology.

Amino acid domains that bind to inorganic materials found in bone, such as calcium or phosphorus, are of particular relevance in the context of tissue repair. Peptides that may nucleate deposition of hydroxyapatite have been identified. For example, the amino acid sequences DSS and SD are found as repeated units in the phosphophoryn family of proteins, which are massively phosphorylated proteins found in close association with the ECM in dentin, for example, and are known to play an important role in hydroxyapatite deposition (Hartgerink 2001 and references therein). Single or multiple repeats of DSS and/or SD can be used as the non self-assembling amino acid domain in the inventive peptides. Scaffolds containing such peptides may facilitate biomineralization when implanted into a subject.

E. Identification of Additional Amino Acid Domains of Interest

One approach to identifying additional amino acid domains that may be used as the non self-assembling portion of an inventive peptide is to systematically screen synthetic peptides derived from the sequence of a naturally occurring protein that is believed to interact with cells, bind to a particular molecule, etc. This approach has been used to identify numerous biologically active peptides as described above. In general, a set of peptides, optionally overlapping, that together encompass all or a significant portion of the sequence is synthesized in vitro. Cells, or a potential binding molecule, are then contacted with individual peptides, and the cellular response, degree of binding, etc., is assessed. The peptides can be labelled to facilitate detection.

In general, peptides obtained from the sequence of any naturally occurring protein can be screened including, but not limited to, the proteins specifically discussed above, e.g., laminin-1, which includes the biologically active peptide motifs YIGSR (SEQ ID NO:33) and RYVVLPR (SEQ ID NO:35) and collagen IV, which includes the biologically active peptide motif TAGSCLRKFSTM (SEQ ID NO:37). One of ordinary skill in the art will readily be able to locate the complete sequence for these proteins, related proteins, other proteins of interest (e.g., other ECM proteins), genes encoding the proteins, etc., in publicly available databases such as those available through the National Center for Biotechnology Information (see web site having URL www.ncbi.nlm.nih.gov) using, for example, the Entrez search engine. Databases can be searched by gene or protein name, by nucleotide sequence (e.g. by searching GenBank) or protein sequence, etc. For example, genes encoding collagen IV proteins can be identified by searching the Gene database using the term "collagen".

As mentioned above, other proteins of interest include additional ECM proteins, e.g., additional basement membrane proteins. Peptide scaffolds particularly suitable for different cell types may be created by screening proteins known to be present in the ECM on or in which that cell type is typically found. For example, the basement membrane in which different cell types are commonly found may contain different isoforms of laminin, collagen, etc. Amino acid domains can be selected from proteins present in the extracellular environment of any cell type of interest. While not wishing to be bound by any theory, it is possible that such proteins will be favorable for culture of that cell type and/or for introduction into the body at a site known to contain cells of that type or at which it is desired to implant or attract cells of that type.

Thus the invention provides a method for designing a self-assembling peptide for formation of a peptide scaffold for a cell type of interest comprising identifying an amino acid domain present in a naturally occurring protein present in the extracellular environment of that cell type (e.g., in the ECM or basement membrane on or in which the cell type is naturally found), screening the peptide to determine whether it produces a biological effect on the cell (either when present in a peptide scaffold or otherwise present in the environment of a cell, as described above), utilizing the amino acid domain as the second amino acid domain of a modified self-assembling peptide, and testing a scaffold comprising the modified self-assembling peptide to determine whether it is favorable for cell growth, results in altered cell phenotype, etc. The screening step can be omitted, i.e., the candidate peptide can be directly incorporated as part of a modified self-assembling peptide without first testing it for biological effect, if desired.

Another approach is to employ display techniques involving peptide libraries such as phage display, cell surface display, or ribosome display (see Sarikaya 2004 and references therein). Phage display and cell surface display employ chimeric proteins that are naturally present on the surface of a phage or cell. The chimeric protein generally contains all or part of a naturally occurring phage or cell surface protein, and a second domain that contains a random peptide sequence encoded by a nucleic acid expressed by the phage or cell. A portion of the nucleic acid has typically been randomized by any of various molecular biological techniques prior to its introduction into the phage or cell (or a precursor thereof), or can be altered thereafter by mutation. A library of phage or cells, each expressing a different version of the chimeric protein on its surface, is contacted with a target (e.g., a ligand (which can be immobilized) or a population of cells). Following the contacting step, weakly binding cells or phage expressing chimeric proteins are washed away while strong binders remain. The process is repeated to enrich for tight binders (biopanning). Various methods of performing directed evolution can also be used.

Another approach to identifying useful amino acid domains is to make a limited number of mutations to known biologically active peptide motifs, binding peptides, etc., e.g., by substitution of one or more amino acids. This may identify peptides with improved properties relative to the starting sequence. The invention encompasses the use of amino acid domains whose sequence differs from that of sequences listed herein by 1, 2, or 3 amino acid residues.

VI. Characterization of Self-Assembling Peptides and Compositions Comprising Them Structures (e.g., nanofibers, macroscopic structures, hydrogels) formed by any of the unmodified self-assembling peptides or the modified self-assembling peptides of the present invention, or composites thereof, may be characterized using various biophysical and optical techniques. Suitable techniques include visual inspection, circular dichroism (CD), dynamic light scattering, Fourier transform infrared spectroscopy (FTIR), rheological assays such as oscillatory rheometry, atomic force microscopy (ATM), scanning electron microscopy (SEM), and transmission electron microscopy (TEM). For example, biophysical methods may be used to determine the degree of beta-sheet secondary structure in the peptide scaffold. Additionally, filament and pore size, fiber diameter, length, elasticity, and volume fraction may be determined using quantitative image analysis of scanning and transmission electron microscopy.

Peptide scaffolds may also be examined using several standard mechanical testing techniques to measure the extent of swelling, the effect of pH and ion concentration on scaffold formation, the level of hydration under various conditions, and the tensile strength. Parameters such as the elastic modulus can be measured. These methods allow one of ordinary skill in the art to determine which of the various modifications and additions to the peptides described below are suitable for use in the methods of the invention. Example 1 describes a variety of methods that were used to characterize an unmodified peptide (RAD16-I), various modified peptide derivatives of RAD16-I, and structures formed from a composite of RAD16-I and various modified peptide derivatives (i.e., structures formed from a solution in which both RAD16-I and modified peptides were present). Non-limiting descriptions of certain techniques that may be used are described in the following sections.

In addition to, or instead of, assessing gel formation in a quantitative manner, e.g., using the rheological tests described herein, more qualitative assessments, including simple visual examination, can be used. A reproducible assessment of gel formation involves probing a composition using a paperclip by stirring and sweeping the material up the sides of a vessel containing the composition, such as a microfuge tube (Sperinde, J C and Griffith L G, *Macromolecules* (2000), 33:5476-5480). A composition can be considered to undergo gelation when it seizes to the paper clip. Further gelation or reversibility of the gel state can be assessed with additional probing. Further gelation would result in a stronger, less viscous material.

Rheometry. Rheological assays can be performed to test the vicoelastic properties of the peptide scaffolds. For example, oscillatory rheometry, which subjects samples to oscillating stresses or oscillating strains, can be performed, e.g., using a controlled strain rheometer, which shears the sample at a controlled strain within a range of frequencies. Various rheometers that can be used are commercially available. Principles of rheometry and its applications to gels, are described, for example, in Clark, 1987 and in Kavanagh & Ross Murphy, 1998.

In general, the output from such a test is G*, the complex modulus. This complex modulus can be defined as:

$$G^* = G' + iG'' \qquad [\text{eq. 1}]$$

In this equation:

G' is the storage modulus which represents the elastic/solid character of the material.

G" is the loss modulus which represents the viscous/fluid character of the material.

In oscillatory rheometry, for a viscous solution, the viscous component of the complex modulus, the loss modulus (G") typically decreases with decreasing oscillatory frequencies, and the storage modulus G' is low. For gels, G' and G" are relatively constant with oscillatory frequency. For example, in preferred embodiments of the invention, the magnitudes of dG'/dw and dG"/dw are less than 2 or, more preferably, less than 1, over a frequency range within the linear region, when measured with a dynamic frequency sweep test, where G' and G" are measured in Pascals (Pa) and w represents frequency in rad/s. The frequency range can be, for example, between 0.1 and 1 rad/s, between 1 and 10 rad/sec, etc. In other preferred embodiments of the invention, the magnitudes of dG'/dw and dG"/dw are less than 0.5, less than 0.2, or less than 0.1 over a frequency range within the linear region, when measured with a dynamic frequency sweep test, where G' and G" are measured in Pa and w represents frequency in rad/s.

For gels, G' is typically greater than zero. In preferred embodiments of the invention G' of a composition formed by self-assembly of an inventive modified self-assembling peptide is greater than or equal to 0.5 Pa. In other preferred embodiments of the invention, G' of a composition formed by self-assembly of an inventive modified self-assembling peptide is greater than or equal to 1.0 Pa, greater than or equal to 5 Pa, greater than or equal to 10 Pa, between 10 and 100 Pa, or greater than 100 Pa when measured in a linear region using a dynamic frequency sweep test. The linear region may be, for example, between 0.1 and 1 rad/s, between 1 and 10 rad/sec, or between 10 and 100 rad/sec. When performing such measurements, a dynamic strain sweep may first performed on the material to set the linear viscoelastic region of the test and to select a fixed strain for dynamic frequency sweep tests. This linear viscoelastic range is generally defined by constant moduli, G' and G". It is important to select a strain within this range to obtain reliable results (Schramm, 1994). For example, for the peptide scaffolds tested in Example 1 the strain selected was 0.01 (dimensionless) and was applied in all assays.

The above description is not intended to limit the invention but simply relates to certain embodiments thereof. Indeed it is noted that a gel has been defined as "any substance that in solution or not creates cross-linking interactions (covalent or non-covalent) to form a network", with the understanding that the substance retains some elastic properties in terms of the deformation of the material under low stress (*Scaling Concepts in Polymer Physics* by Pierre-Gilles de Gennes, Cornell University Press (1979)). In the case of a hydrogel, the network retains a significant amount of water.

Atomic Force Microscopy. Atomic force microscopy (AFM) is a technique that allows resolution of surface structures down to the nanometer scale by measuring the interaction of a microscopic sharp tip used to scan the sample surface and the sample. AFM involves scanning a sharp tip on the end of a flexible cantilever across a sample surface while maintaining a small, constant force. The scanning motion is conducted by a piezoelectric tube scanner which scans the tip in a raster pattern with respect to the sample (or scans the sample with respect to the tip). The tip-sample interaction is typically monitored by a reflecting laser off the back of the cantilever into a split photodiode detector. By detecting the difference in the photodetector output voltages, changes in the cantilever deflection or oscillation amplitude can determined.

There are two most commonly used modes of operation: contact mode AFM and TappingMode™ AFM which are conducted in air or liquid environments. Contact mode AFM operates by measuring repulsive forces between a tip and the sample (Binning et al, 1986). The instrument lightly touches the tip. In TappingMode™ AFM, the images are derived from measurements of attractive forces, the tip does not touch the sample. It oscillates at its resonance frequency lightly "tapping" on the surface during scanning. TappingMode™ AFM may be particularly appropriate for assessing nanofiber formation in peptide scaffolds of the invention because it allows measurements to be made on soft, fragile and adhesive surfaces without damaging them, which can be a drawback for contact mode AFM.

VII. Therapeutic Applications

A peptide structure made by self-assembly of the modified self-assembling peptides of the invention or by self-assembly of combinations of modified and unmodified self-assembling peptides described herein, may be used to treat a variety of tissue defects and diseases. Peptide hydrogel structures, either with or without cells growing on the surface or encapsulated within may be implanted into the body, e.g., surgically or using any other type of suitable procedure. Other routes, including oral, percutaneous, intramuscular, intravenous, and subcutaneous may be employed. One of ordinary skill in the art will be able to select an appropriate delivery technique.

It is noted that the peptide structures have the advantage of eliciting minimal or no detectable immune or inflammatory response in mammals. Further, the peptide structures exhibit no detectable swelling when added to a saline solution. This lack of swelling is probably due to the high water content of the structure (typically >99%). This property reduces the probability of an unregulated expansion of the structure that could lead to adverse physiological effects on neighboring tissues.

In general, the methods and compositions of the invention may be useful in any situation involving injury or damage to tissue. Such injury may occur as a result of surgery, trauma, tumor, degenerative disease, or other diseases or conditions. The injury may, but need not, involve death of cells. The methods and compositions are useful to restore structural and/or functional integrity to the tissue, i.e., to aid in restoring the tissue to the functional or structural condition that existed prior to the injury. Certain injuries may result in physical barriers that can impede regeneration or repair of tissue. Such barriers may include areas of necrosis, cavitation, or scar tissue formation. In certain embodiments of the invention introducing the materials described herein at a site of injury allows cell or tissue growth from a location proximal to the site of injury or barrier to a location distal to the site of injury or barrier.

Certain compositions and methods of the present invention may be used to ameliorate the effects of disease or degeneration of an organ, to repair an injury to an organ or other body structure or to form an organ or other body structure. Such organs or body structures include, but are not necessarily limited to, vascular tissue, brain, nervous tissue, esophagus, fallopian tube, heart, intestines, gallbladder, kidney, liver, lung, ovaries, pancreas, prostate, bladder, spinal cord, spleen, stomach, testes, thymus, thyroid, trachea, ureter, urethra, uterus, and skin.

In general, a variety of devices may be used to introduce the scaffold material at the site of injury. Delivery via a syringe is one convenient technique. Peptides can also be introduced by catheter or directly at a site of surgery. In certain embodiments of the invention a peptide solution in which peptides are unassembled or minimally assembled (i.e., a solution that has not formed a gel) is introduced into the body. In other embodiments of the invention scaffold formation is allowed to occur in vitro and the assembled scaffold is introduced into the body.

Peptide scaffods encapsulating cells may be used for a variety of therapeutic purposes. Unassembled peptides and cells may be mixed in vitro and the structure may then self-assemble after administration and encapsulate the cells in vivo. As described above, in certain embodiments of the invention the administered solution contains less than 10, 5, 1.0, or 0.1 mM ion (e.g., cation) or is substantially free of ions (e.g., cations), and the concentration of the iso-osmotic solute is at least 50, 150, or 300 mM. In other embodiments, the concentration of iso-osmotic solute is contained in one of the following ranges 200 to 250 mM, 250 to 270 mM, 270 to 300 mM, 300 to 400 mM, 400 to 500 mM, 500 to 600 mM, 600 to 700 mM, 700 to 800 mM, or 800 to 900 mM, inclusive. Suitable iso-osmotic solutes include, but are not limited to, carbohydrates, such as sucrose.

Any of the cell types mentioned above may be used. Thus in addition to or instead of vascular endothelial cells, the compositions of the present invention may include a variety of other cell types and/or precursors of such cell types. The cell(s) may be autologous or non-autologous. They may be allogeneic or non-allogeneic. They may be from the same species as the subject into which they are to be introduced or from a different species. They may be fetal or adult.

In various embodiments of the invention one or more additional substances is added to the peptide scaffold either prior to or following self-assembly. The substance may serve any of a number of purposes, including, but not limited to, those described below. If the scaffold is implanted into the body, growing cell processes or tissues may contact the substance as they extend or grow into the area occupied by the peptide scaffold. In certain embodiments of the invention the substance is released from the scaffold, e.g., by diffusion, or by release from the scaffold as it degrades over time. The particular peptide sequence, and/or peptide concentration and parameters such as degree of cross-linking may be selected to provide a desired rate of degradation and release of the substance. The substance may contact cells and tissues at or near the site of implantation and/or may enter the bloodstream and travel to more distant locations. Substances that can be added include, but are not limited to, antibiotics or antifungal agents to treat or reduce the risk of infection, chemotherapeutic agents to treat tumors, etc. The peptide solution, of a macroscopic structure formed therefrom may thus comprise a therapeutically active compound or chemoattractant. Examples of such compounds include natural or synthetic small molecules; nucleic acid molecules such as nucleic acid molecules that mediate RNA interference (RNAi) (Dorsett and Tuschl 2004, and references therein), e.g., short interfering RNAs (siRNAs) or short hairpin RNAs (shRNAs), ribozymes, or plasmids; peptides or proteins such as integrins or cell adhesion molecules; proteins such as antibodies, etc.

In certain embodiments of the invention the peptide solution, or a macroscopic structure formed therefrom, incorporates an agent that enhances or promotes differentiation, dedifferentiation, or transdifferentiation, e.g., a growth factor, such as vascular endothelial growth factor, granulocyte macrophage colony stimulating factor, angiopoietin 1 or 2, epidermal growth factor, nerve growth factor, transforming growth factor-$\alpha$, transforming growth factor-$\beta$, tumor necrosis factor $\alpha$, platelet-derived growth factor, insulin-like growth factor, acidic fibroblast growth factor, basic fibroblast growth factor, hepatocyte growth factor, brain-derived neurotrophic factor, keratinocyte growth factor, a bone morphogenetic protein, or a cartilage-derived growth factor. Combinations of growth factors and/or therapeutic agents or chemoattractants may be used. Peptide hormones may also be used. Naturally occurring peptides or modified versions including peptides such as atrial natriuretic peptide may be used.

The macroscopic structure may incorporate an agent that induces reentry into the cell cycle. Such agents may be added to the peptide solution or to the electrolyte solution prior to initiation of self-assembly. In this case the concentration of the agent will likely be substantially uniform within the assembled structure. In certain embodiments of the invention the agent is added to media with which the peptide structure is incubated before or after addition of cells. After addition to the media, a portion of the agent enters the peptide structure, e.g., through diffusion. This process may create a gradient. Cells on or in different regions of the structure may exhibit different responses to the agent depending upon the concentration of the agent at the location of the cell. Substances that counteract the effect of a molecule that is inhibitory for tissue regeneration or repair, whether by causing degradation, sequestering, reducing expression, or blocking interaction of the molecule with a cell, may also be incorporated.

Growth factors are typically used at concentrations ranging between about 1 fg/ml to 1 mg/ml. Frequently growth factors are used at concentrations in the low nanomolar range, e.g., 1-10 nM. In certain embodiments of the invention growth factors are used at concentrations that are not typically used in the prior art or that are not typically found in vivo under normal conditions. For example, growth factors may be used at concentrations that are 5 fold greater, 10 fold greater, 20 fold greater, 100 fold greater, etc., than is typically required to produce effects or than typically occurs in vivo. Titration experiments can be performed to determine the optimal concentration of a particular agent, such as a growth factor, depending upon the particular effects desired. Factors may be added in purified form or as components of a complex biological mixture such as serum.

As described above, repair and regeneration of tissue can be enhanced by supplying factors such as growth factors, cell adhesion molecules, integrins, etc. One way to provide such molecules (or others), is to deliver cells at the site of injury. The cells may produce molecules that promote regeneration or otherwise contribute to producing an environment permissive for regeneration. Various progenitor cells may also be useful. Any of these cell types may be incorporated into the scaffold. In addition, any of these cell types (or others) can be genetically modified, e.g., to increase the production of a regeneration promoting factor, prior to incorporation into the scaffold.

Gene therapy techniques may be used to increase expression of genes that encode desirable products. Gene therapy encompasses delivery of nucleic acids comprising templates for synthesis of a molecule of interest to a cell of interest. The nucleic acid (or a nucleic acid derived from the nucleic acid as, for example, by reverse transcription) may be incorporated into the genome of the cell or remain permanently in the cell as an episome. However, gene therapy also encompasses delivery of nucleic acids that do not integrate or remain permanently in the cell to which they are delivered. Such approaches permit temporary or transient synthesis of a molecule of interest.

Vectors and vehicles that provide nucleic acids comprising templates for synthesis of desirable molecules may be incorporated into peptide scaffolds, from which they may be taken up by cells at or near a site of injury. Preferably the nucleic acid includes a coding sequence for a gene to be expressed in a cell of interest and also includes appropriate expression signals, e.g., promoters, terminators, etc., to ensure proper expression. In certain embodiments of the invention the expression signal(s) are cell type specific, so that the gene will only be expressed in cells of a particular cell type.

In general, either viral or non-viral vectors may be used. In certain embodiments of the invention the vector is a viral vector that is able to infect neurons. For example, herpes virus, adenovirus, adeno-associated virus, retroviruses, or lentiviruses may be used. It may be preferable to avoid the use of intact viruses in delivering templates to cells. Thus it may be preferable to deliver DNA vectors or linear DNA molecules. These vectors may, but need not, include viral sequences such as long terminal repeats, etc. Any of a wide variety of agents useful for transfection may be used to enhance uptake of nucleic acids by cells. Such agents include a wide variety of cationic polymers and modified cationic polymers, lipids, etc. Cell-type specific targeting ligands, e.g., ligands or antibodies that specifically bind to a molecule expressed on a cell type of interest may be attached to a gene therapy delivery agent to allow introduction of the agent into only certain cell types. In general, the nucleic acid and any appropriate gene therapy delivery agent (e.g., a cationic polymer) may be incorporated into the scaffold in any of the ways discussed herein.

In certain embodiments of the invention a therapeutically desirable genetic modification may be made. For example, in a case where an individual harbors a mutation in a particular gene it may be desirable to introduce a wild-type copy of the gene into the progenitor cell for gene therapy purposes. In certain embodiments of the invention it may be desired to introduce a gene encoding a particular receptor, e.g., a growth factor receptor, in order to confer or enhance a particular differentiation, dedifferentiation, or transdifferentiation potential by allowing cells to respond to the growth factor.

The number of cells to be administered for therapeutic purposes, the relative proportion of cells of different phenotypes, and/or the concentration of cells within a peptide structure can be altered as appropriate for the particular condition or injury to be treated.

In certain embodiments of the invention cells, e.g., vascular endothelial cells and/or their progeny that have proliferated and/or differentiated on or within a peptide structure are removed or extracted from the structure. Removal or extraction may be accomplished by any suitable means, including removal with a suction pipette, mechanical disruption of the scaffold, enzymatic degradation of the structure in vitro, etc. In certain embodiments of the invention the method selected results in removal or extraction of approximately 10% of cells, between 10% and 25% of the cells inclusive, between 25% and 50% of the cells inclusive, between 50% and 75% of the cells inclusive, or between 75% and 100% of the cells inclusive. Methods that result in any convenient range may be selected. The method selected may depend upon the purposes for which the cells are to be used, the number of cells required, etc. In certain embodiments of the invention the viability of the removed or extracted cells is approximately 10% of cells, between 10% and 25% inclusive, between 25% and 50% of cells inclusive, between 50 and 75% of cells, inclusive, or between 75% and 100% of cells inclusive. Methods that result in any convenient range may be selected. The method selected may depend upon the purposes for which the cells are to be used, the number of cells required, etc.

The extracted cells may be further cultured in vitro, either on or in a peptide hydrogel structure or in any other culture vessel. The extracted cells may be administered to a subject by any appropriate route, including intravenous, subcutaneous, oral, percutaneous, intramuscular, or surgical. The administered cells may be used to supplement a tissue, organ, or body structure, e.g., a tissue, organ, or body structure suffering from a deficiency of vascular tissue. The administered cells may synthesize or otherwise supply a therapeutic agent. For example, the administered cells may supply a protein, e.g., an enzyme that the individual lacks. The administered cells may be genetically modified and thus used as a means to deliver gene therapy.

The self-assembling peptides of the invention may be used to promote formation of a layer of vascular endothelium at a site of injury, e.g., following a procedure such as angioplasty. They can also be used as coating materials, e.g., for devices such as vascular grafts or stents, to promote endothelialization. In an alternate approach, the peptides form a layer on the inner surface of an artificial conduit such as an artificial blood vessel. Endothelial cells are cultured on the layer formed by self-assembly of the peptides for a period of time. The cells secrete ECM components. The cells may then be removed, leaving behind an intact basement membrane layer containing ECM molecules synthesized by the cells. The artificial conduit is then implanted into a host. In another approach, the conduit is implanted into a host without removal of the endothelial cells.

The inventive self-assembling modified peptides and structures containing them can be used as or within nerve guides, e.g., to promote regeneration of axons and nerves in the peripheral nervous system.

VIII. Additional Embodiments and Equivalents

The invention provides kits that may be used for culturing cells and/or for forming peptide scaffolds that can be introduced into the body of a subject. The kits comprise one or more self-assembling peptides of the invention, which may be provided in dry or lyophilized form, in solution, or in assembled or partially assembled form. The kits may further comprise one or more of the following items: a population of cells, cell or tissue culture medium, a predetermined amount of a growth factor, a predetermined amount of an ion or salt thereof, instructions for preparing the self-assembling peptide for cell culture, instructions for culturing cells on or within a peptide hydrogel structure (e.g., for encapsulating cells), instructions for introducing the self-assembling peptide into a subject, a vessel in which cell culture may be performed, a liquid in which the peptide can be dissolved, a syringe, an ion or salt thereof for initiating peptide self-assembly, one or more growth or differentiation factors, medium for tissue culture, cells (e.g., vascular endothelial cells), control peptide, etc. Additional items may also be included.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance, which can be adapted to the practice of this invention in its various embodiments and the equivalents thereof.

EXAMPLES

Example 1

Physicochemical Characterization of Peptide Scaffolds

Materials and Methods

Certain of the following materials and methods are relevant to a number of the following examples. Catalog numbers are listed in parentheses.

General Reagents.

PBS: Phosphate buffered saline, 1 mM $KH_2PO_4$, 10 mM $Na_2HPO_4$, 137 mM NaCl, 2.7 mM KCl, pH 7.4, (166789, Roche Diagnostics Corp., IN).

Trypsin: Trypsin-EDTA (25300-054, GibcoBRL, US), 0.05% trypsin, 0.53 mM EDTA·4Na in HBBS, without calcium or magnesium, mycoplasma tested.

EGM-2: Endothelial semi-defined media (CC-3162, Cambrex, MD) containing hEGF, hydrocortisone, hFGF-B, VEGF, $R^3$-IGF-1, ascorbic acid, gentamicin-amphoterin, heparin and only 2% FBS.

HAEC: Human aortic endothelial cells (CC-2535, Cambrex, MD).

Triton-X-100: was purchased from Sigma (T 0284, MO).

Protease inhibitor cocktail: Complete mini protease inhibitors cocktail was purchased from Roche (1836153, Indianapolis, Ind.).

TNE: Buffer containing 10 mM Tris base, 1 mM EDTA, 200 mM NaCl, pH 7.4.

BSA: Bovine serum albumin (100030, Boehringer Manheim, Ind.).

Peptides. All peptides used in this work were obtained from SynPep Corporation (www.synpep.com; Dublin, Calif.). The identity of the peptides was confirmed by measuring their molecular weight by mass spectrometry and comparing with the theoretical molecular weight (Table 3). Abbreviations for the peptides are as in Table 4, in the Results section of this example.

TABLE 3

Expected and obtained M.W. for peptide scaffolds.

| Peptide | Theoretical M.W. | Obtained M.W. |
|---|---|---|
| RAD16-I | 1713 | 1712.8 |
| AAS | 2995.5 | 2996 |
| CSR | 3825.5 | 3826 |
| YIG | 2403.7 | 2404 |
| PDS | 2338.4 | 2339 |
| RYV | 2710.1 | 2711 |
| KAF | 3308.9 | 3309 |
| TAG | 3110.4 | 3110 |

Peptides were dissolved in deionized water at a final concentration of 0.5% (5 mg/ml) by sonicating for ~20 min (Aquasonic, model 50T, VWR, PA). Peptide hydrogel formation was achieved on top of a cell chamber insert (10 mm diameter, 0.5 cm² area, pore size=0.2 μm, cat# 136935, Nalge Nunc International, IL), as described further below.

Circular dichroism (DC). CD spectra were gathered on an Aviv model 202 spectropolarimeter. Samples were prepared by diluting stock peptide solutions in water (0.5%) to a working concentration of 25 μM. Samples were analysed at room temperature in a quartz cuvette with a path length of 0.3 cm and in the wavelength range 195-250 nm.

Atomic force microscopy (AFM). Peptide from stock solutions (0.5%) were diluted to a working concentration of 0.01% (w/v). AFM images were obtained with a Multi 75 silicon scanning probe (MPP-21100, Nanodevices Inc., CA) with a resonance frequency of 75 KHz, spring constant 3 N/m, tip curvature radius <10 nm and 225 μm length. Images were obtained with a Multimode AFM microscope (Nanoscope Ma, Digital Instruments, CA) operating in Tapping-Mode. Typical scanning parameters were as follows: tapping frequency 75 KHz, RMS amplitude before engage 1-1.2 V, setpoint 0.7-0.9 V, integral and proportional gains of 0.2-0.6 and 0.4-1.0 respectively, and scan rate 1.51 Hz.

Rheometry. Rheological assays were performed on a 50 mm parallel plate ARES strain controlled rheometer (Rheometric Scientific, NJ). Samples were dissolved in deionized water at a final concentration of 2.9 mM and sonicated for one hour the day prior to the analysis. A volume of 1 ml was loaded on the lower plate, and the upper plate was set to a gap size between 0.4-0.45 mm. Dynamic frequency sweep tests were performed in a range of frequencies from 100 to 0.1 rad/s. After the test, PBS was added around the lower plate in order to promote gelation. The peptide was allowed to gel for 10 min at room temperature before the test was performed once again. After a dynamic frequency sweep test, the behavior of samples over time was tested. A dynamic time sweep test was performed at 10 rad/s for 5 min.

Data analysis. Standard deviations were calculated for the data and are represented as error bars on the graphs.

Results

The peptides used in the examples are based on the self-assembling peptide RAD16-I. The peptide was modified to include a variety of peptide motifs previously identified as mediating various biological activities. Physicochemical and structural properties of the peptides were assessed using a variety of techniques. Peptide solubility in aqueous solution was tested. The ability of the peptides to self-assemble into higher order structures was examined. In particular, the ability of the peptides to form various secondary structures (e.g., β-sheet) was determined using circular dichroism. The ability of the peptides to self-assemble into nanofibers was evaluated using atomic force microscopy (AFM). Gel formation was assessed by visual observation and rheology.

Table 4 summarizes the physicochemical and structural properties found for RAD16-I and the modified peptides. To simplify the nomenclature of each designed peptide, an abbreviation is given for each peptide. In the table, Ac stands for an acetyl group, and the N to which it is attached represents the N terminus of the peptide and is not part of the sequence. C represents the C terminus of the peptide and is not part of the sequence. $CONH_2$ indicates that the carboxylic acid group of the C terminal amino acid is converted to an amide. Results are further described below.

TABLE 4

Physicochemical and structural properties of modified peptides.

| Peptide sequence | Abbreviation | Solubility in water 1% (w/v) | Gel formation (visual) | Secondary structure (CD) | Presence of nanofibers (AFM) |
|---|---|---|---|---|---|
| AcN-(RADA)$_4$-CONH$_2$ (SEQ ID NO: 38) | RAD16-I | + | + | β-sheet | + |
| AcN-AASIKVAV-GG-(RADA)$_4$-CONH$_2$ (SEQ ID NO: 39) | AAS | + | + | β-sheet | + |
| AcN-CSRARKQAASIKVAV-GG-(RADA)$_4$-CONH$_2$ (SEQ ID NO: 40) | CSR | − | | | |
| AcN-YIGSR-GG-(RADA)$_4$-CONH$_2$ (SEQ ID NO: 41) | YIG | + | + | β-sheet | + |
| AcN-PDSGR-GG-(RADA)$_4$-CONH$_2$ (SEQ ID NO: 42) | PDS | + | + | β-sheet | + |
| AcN-RYVVLPR-GG-(RADA)$_4$-CONH$_2$ (SEQ ID NO: 43) | RYV | + | + | β-sheet | + |
| AcN-KAFDITYVRLKF-GG-(RADA)$_4$-CONH$_2$ (SEQ ID NO: 44) | KAF | + | + | Random coil | − |
| AcN-TAGSCLRKFSTM-GG-(RADA)$_4$-CONH$_2$ (SEQ ID NO: 45) | TAG | + | + | β-sheet | + |

Solubility. All the sequences were found to form clear solutions in water at a concentration of 1% (w/v, 10 mg/ml) except for CSR which was insoluble. This last peptide was not used for the next series of assays.

Gel formation. Each peptide solution at 1% was used to assess hydrogel formation. Increased viscosity was observed by visual inspection after standing overnight at room temperature in two cases, RAD16-I and AAS, but longer periods of time were required to observe an increase in the viscosity for the rest of the peptides. For all the soluble peptides, gel formation was readily observed upon the addition of equal volumes of phosphate buffered saline (PBS).

Circular dichroism. CD spectra were obtained for each peptide sequence to assess its secondary structure. The secondary structure identifies ordered structures within a polypeptide such as α-helices and β-sheets. If the polypeptide shows no regular order the structure is a random coil. A typical spectrum for a β-sheet structure shows a minimum molar ellipticity around 218 nm, while the CD spectrum for a α-helix shows two minima at 209 and 222 nm. (Havel, 1996).

Figure 4:
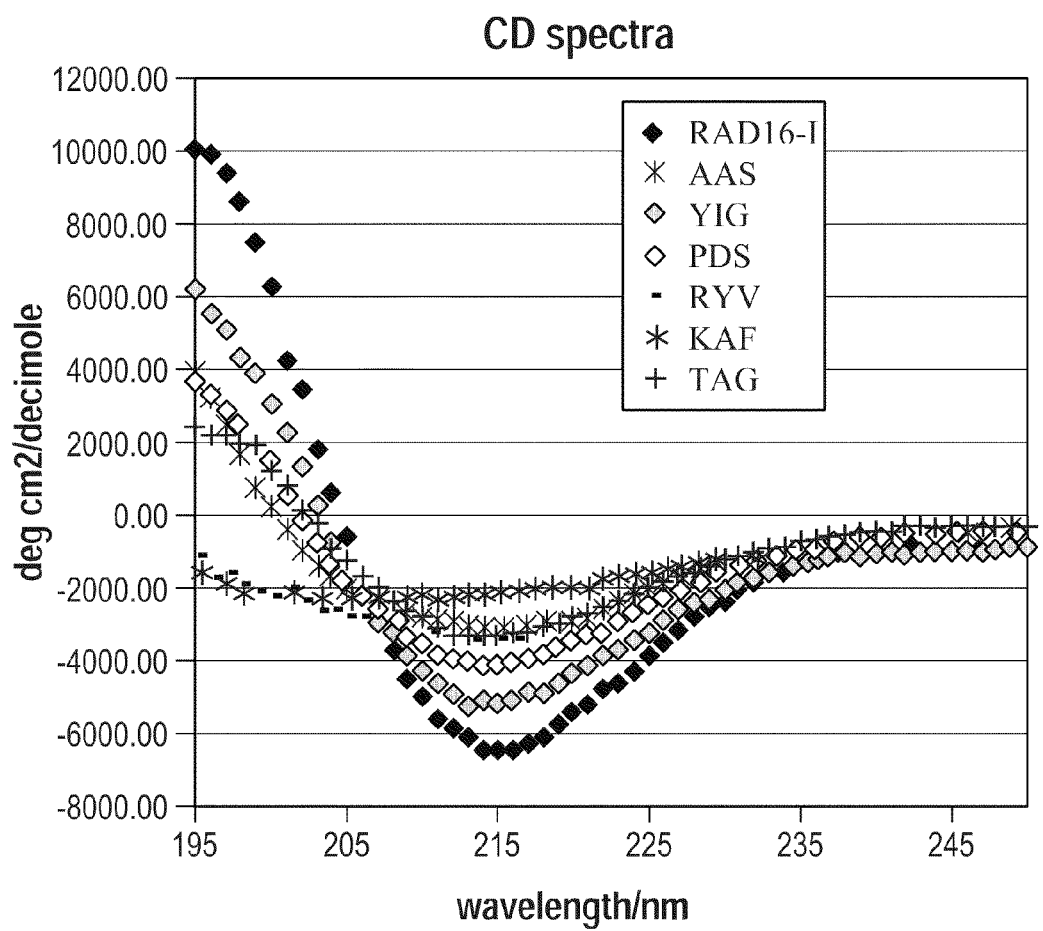
FIG. 4 illustrates physicochemical characterization of peptides RAD16-I, AAS, YIG, PDS, RYV, KAF, and TAG by circular dichroism (CD). The graph presents CD spectra of 25 mM peptide solutions in water in the absence of added ions.
Figure 5A:
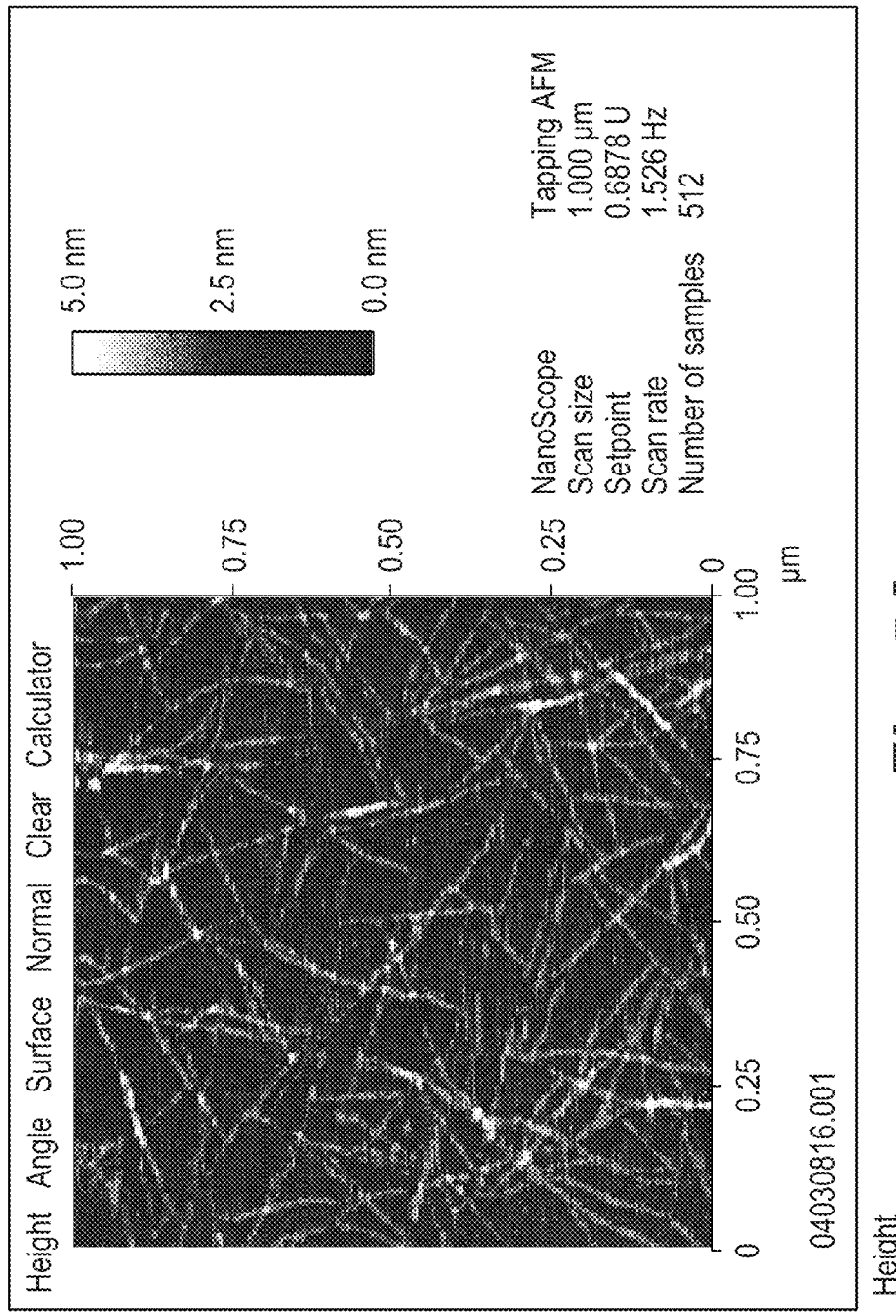
FIGS. 5A-5G show physicochemical characterization of peptides RAD16-I, AAS, YIG, PDS, RYV, KAF, and TAG by Atomic Force Microscopy and demonstrates the formation of nanofibers by all peptides except KAF.
Figure 5B:
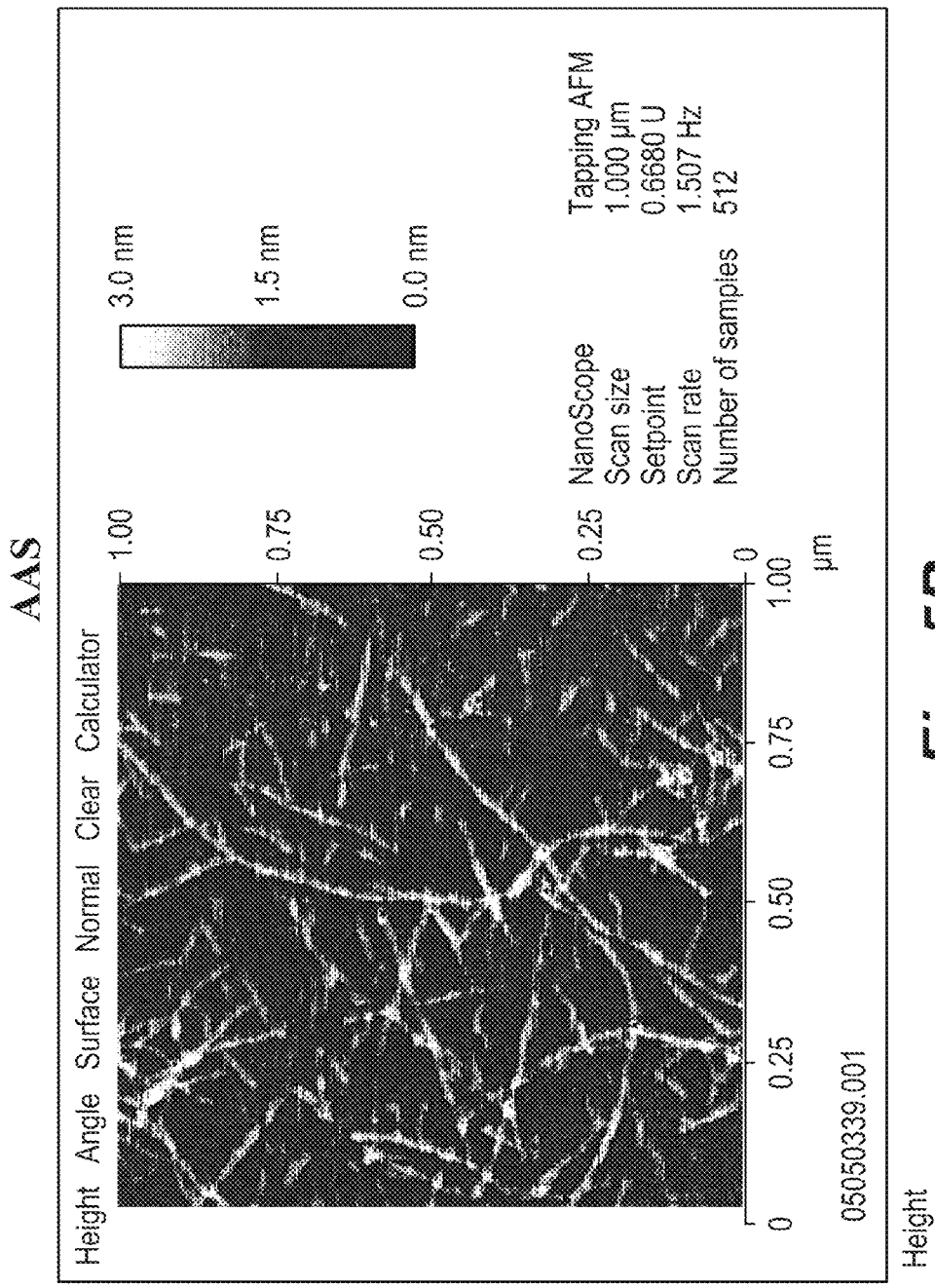
Figure 5C:
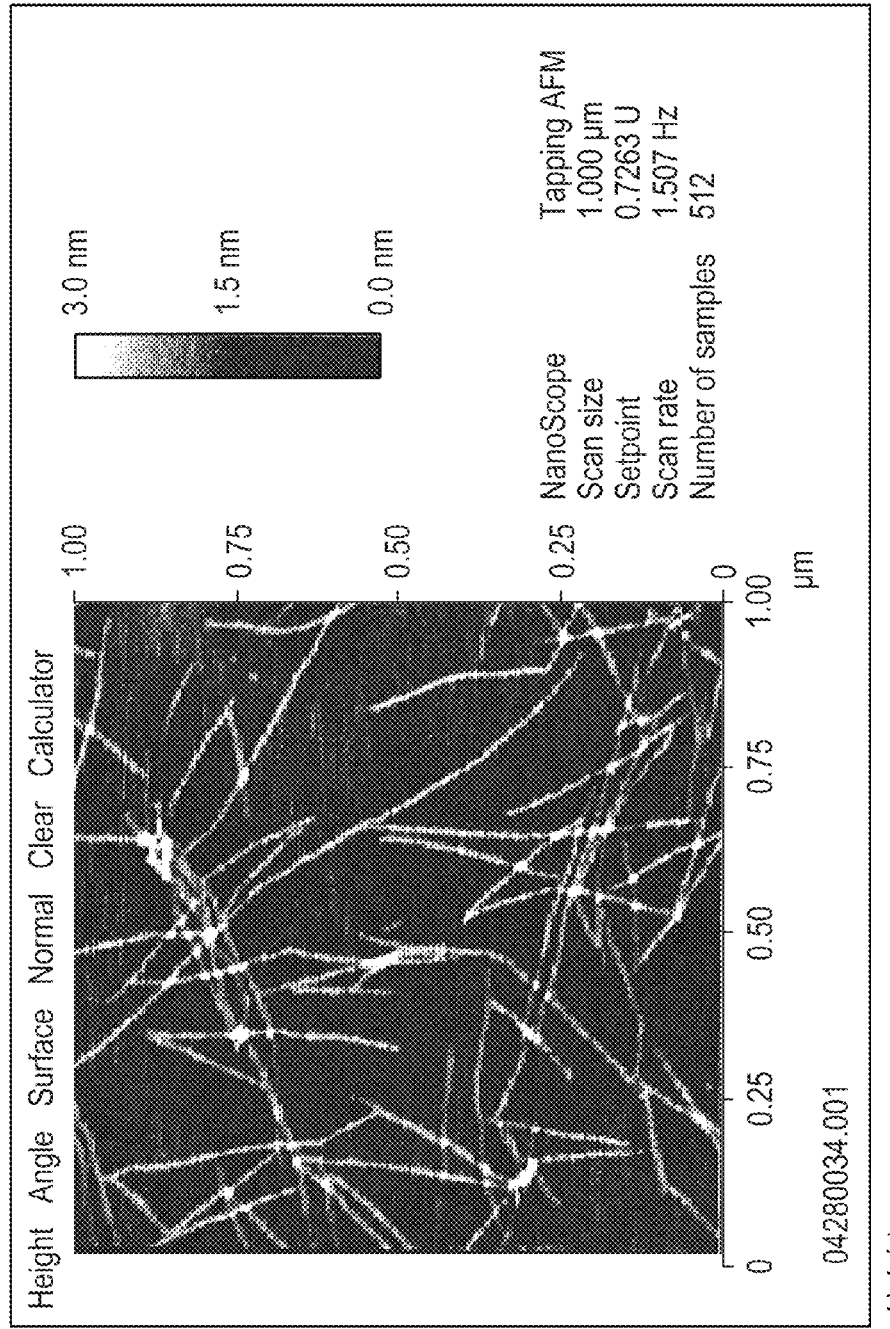
Figure 5D:
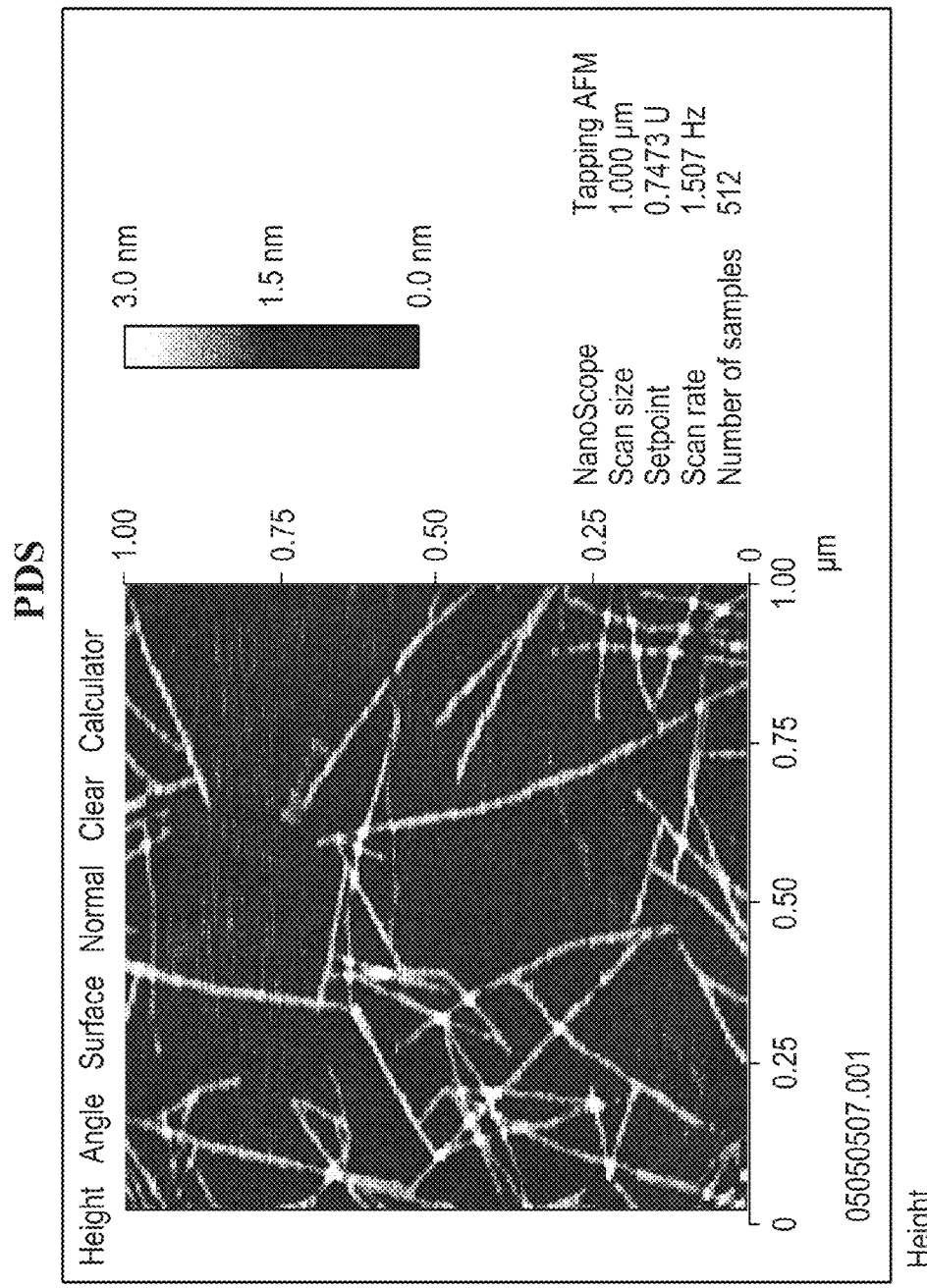
Figure 5E:
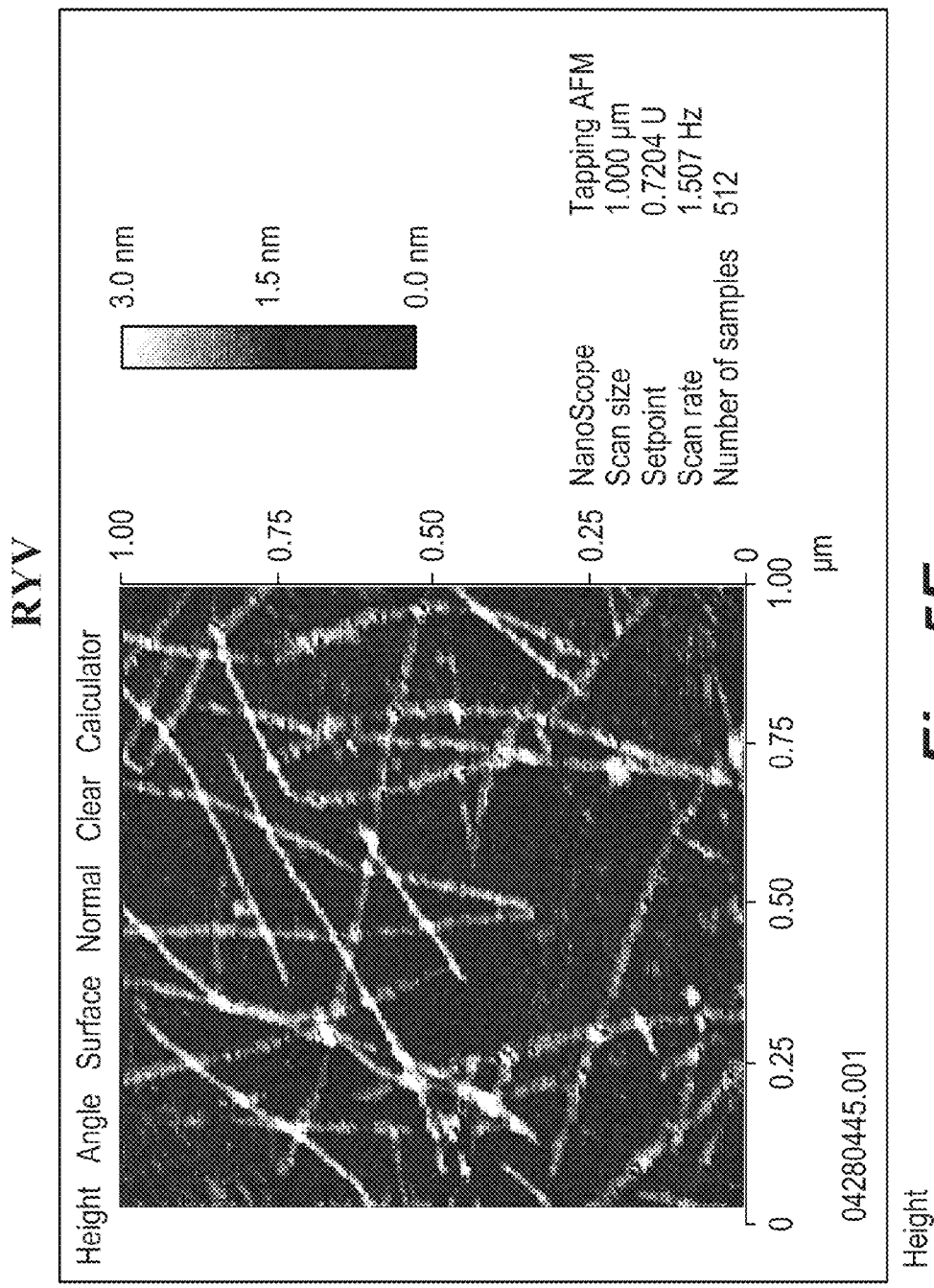
Figure 5F:
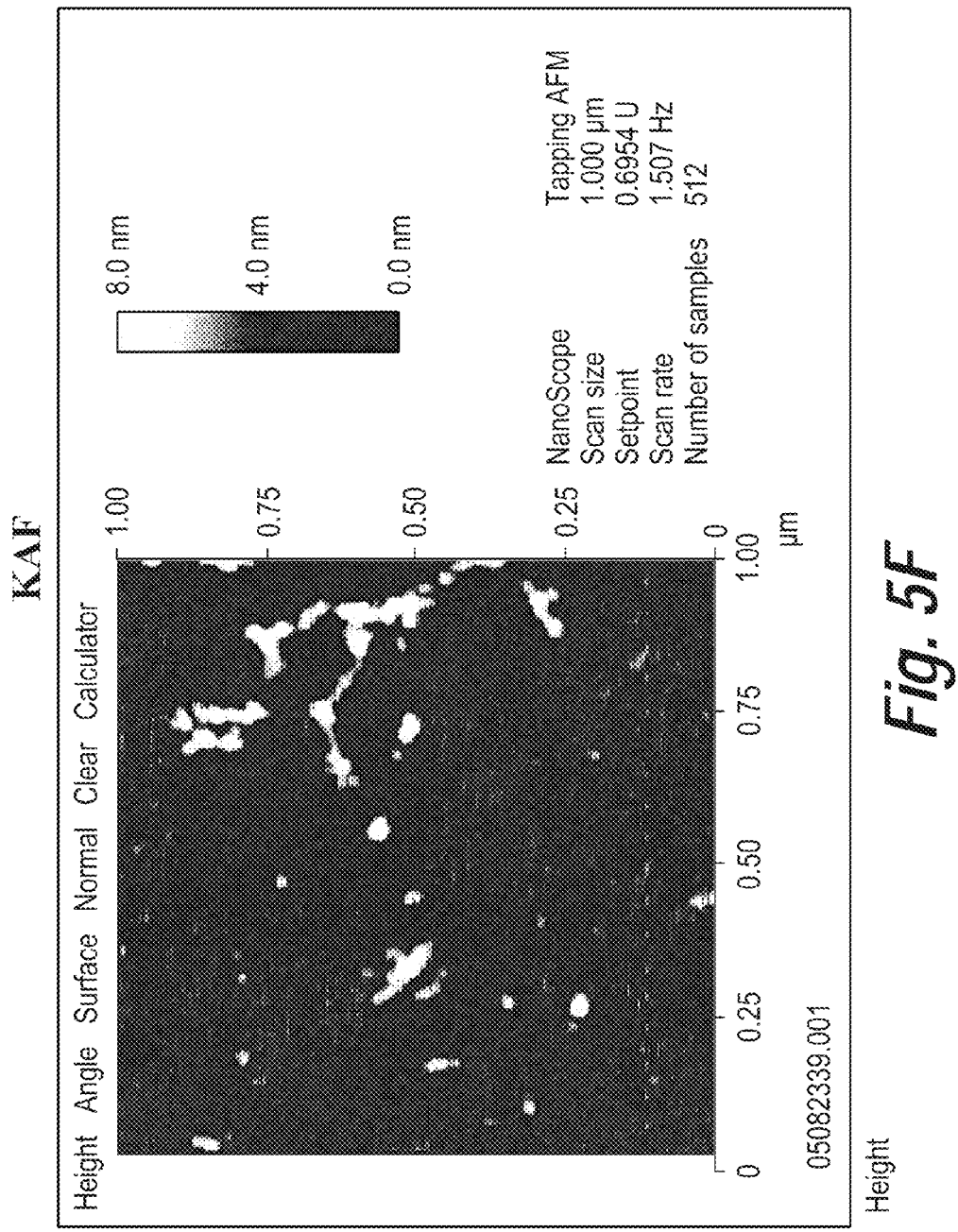
Figure 5G:
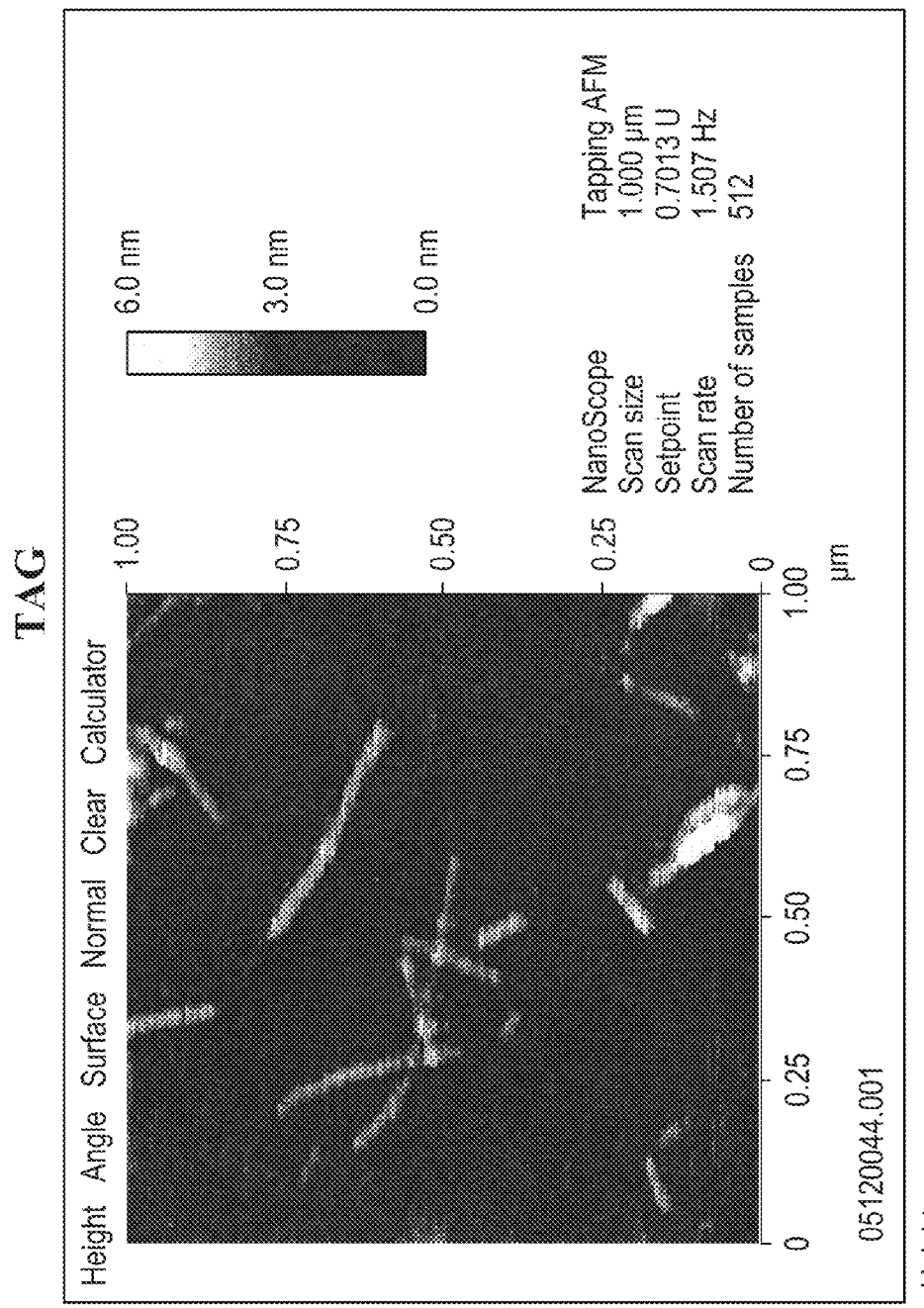

CD studies for most of the peptides showed a spectrum typical of a β-sheet structure with a minimum molar ellipticity (deg cm$^2$/decimole) around 218 nm (FIG. 4). The observed secondary structures are listed in Table 4. One peptide KAF, assumed a random coil configuration. In the other cases, the addition of the short peptide sequence resulted in a decrease in the intensity of the molar ellipticity at 218 nm. The structures assumed by the modified peptides displayed less beta-sheet character than the structure of RAD16-I.

Atomic Force Microscopy. Atomic force microscopy technique was employed to study the structures adopted by the peptide scaffolds. With the single exception of KAF, the presence of nanofibers was observed (FIGS. 5A-5G). AFM images shown in FIGS. 5A-5G are μm×1 μM in size, and the nanofibers are about 25 nm thick. The observation of such nanofibers supports the hypothesis that these new peptide sequences are suitable to use as scaffolds for cell culture. Without being bound by any theory, the fact that KAF does not self-assemble into nanofibers indicates that β-sheet structures of self-complementary peptides may be a requirement for the self-assembling process to give rise to nanofibers (Zhang et. al., 1993). In addition, we concluded that the hydrogel formed by the sequence KAF is a colloid.

Figure 19A:
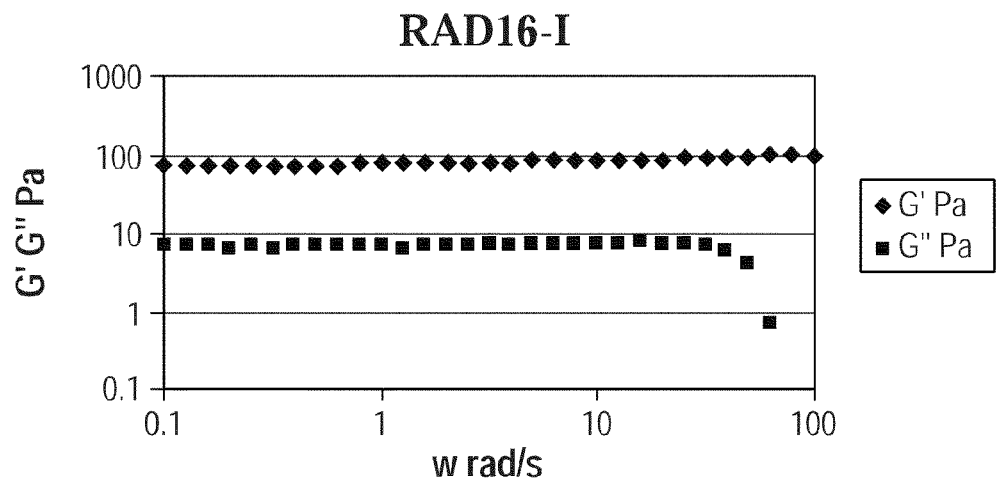
FIG. 19 shows a comparison of dynamic frequency sweep tests for RAD16-I before (A) and after (B) addition of PBS.
Figure 19B:
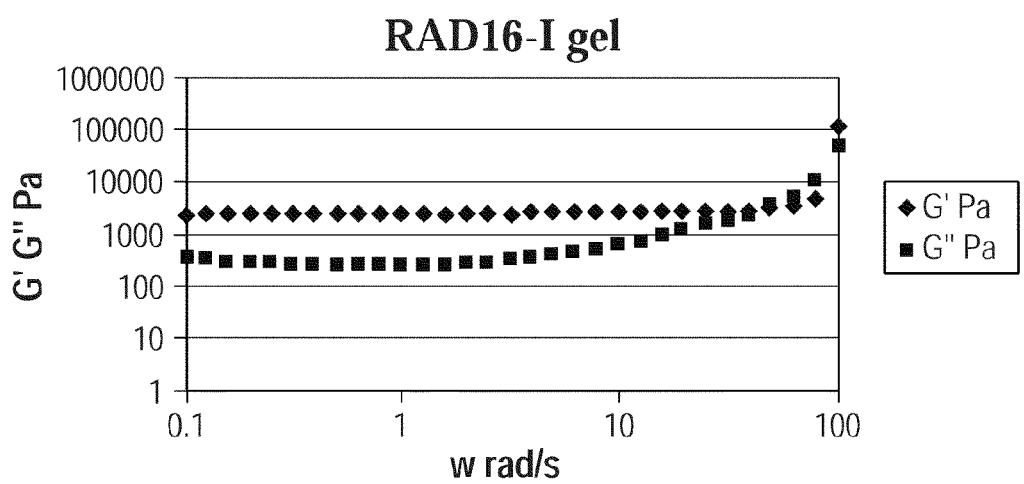

Rheology. A dynamic strain sweep was first performed on RAD16-I to set the linear viscoelastic region of the test and to select a fixed strain for the dynamic frequency sweep tests (FIG. 19). This linear viscoelastic range is defined by constant moduli, G' and G". It is important to select a strain within this range to obtain reliable results (Schramm, 1994). The strain selected was 0.01 (dimensionless) and was applied in all assays.

Figure 18:
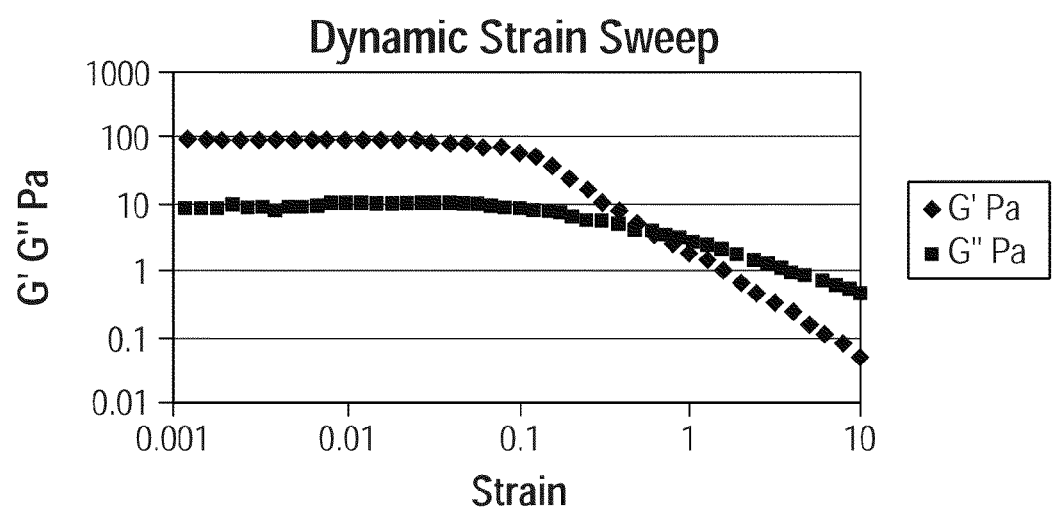
FIG. 18 shows a dynamic strain sweep performed on RAD16-I to establish a linear range.

After performing a test for RAD16-I in its liquid form, PBS was added around the plates to allow hydrogel formation for 10 minutes, and the test was performed once again. FIG. 18 shows the results obtained for this experiment. Although before adding PBS the peptide RAD16-I already displayed gel-like characteristics under the conditions (e.g., pH, temperature, etc.) tested (G'>G" and constant moduli), upon the addition of salts both moduli increased (≈10 fold) indicative of a significant increase in gel strength.

Figure 6A:
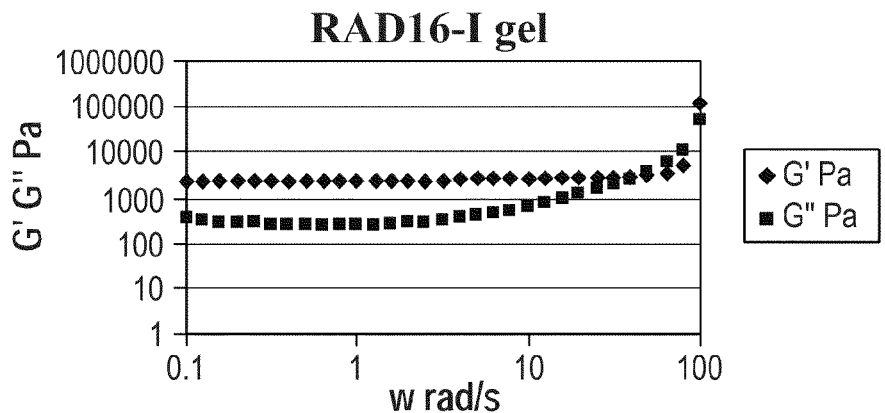
FIGS. 6A-6G show physicochemical characterization of peptides RAD16-I, RYV and TAG by rheology. The plots show a dynamic frequency sweep test for peptide scaffolds at a fixed strain of 0.01. G' (storage modulus) represents the elastic character of the material, and G" (loss modulus) represents its viscous character.
Figure 6B:
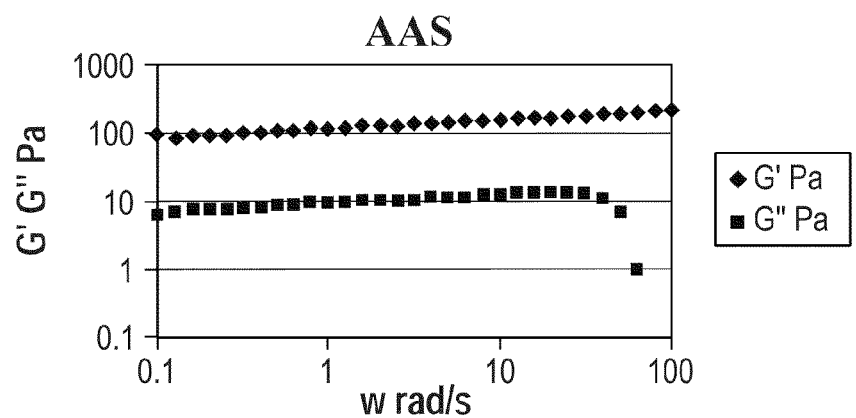
Figure 6C:
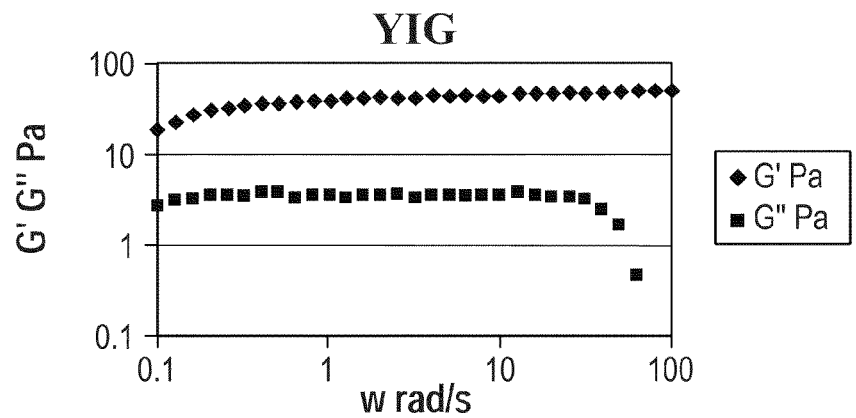
Figure 6D:
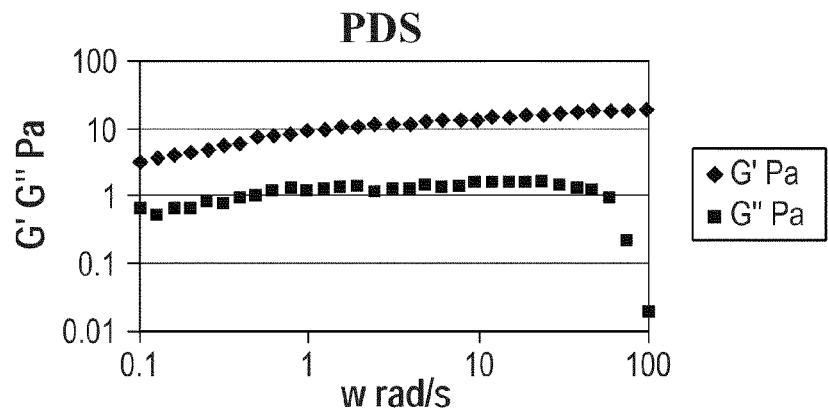
Figure 6E:
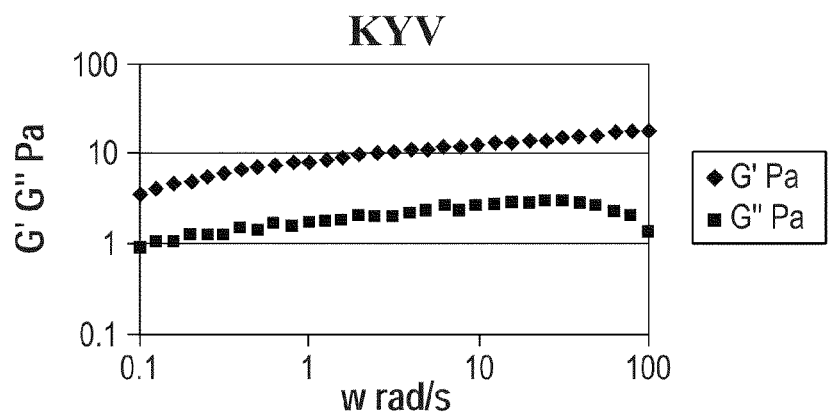
Figure 6F:
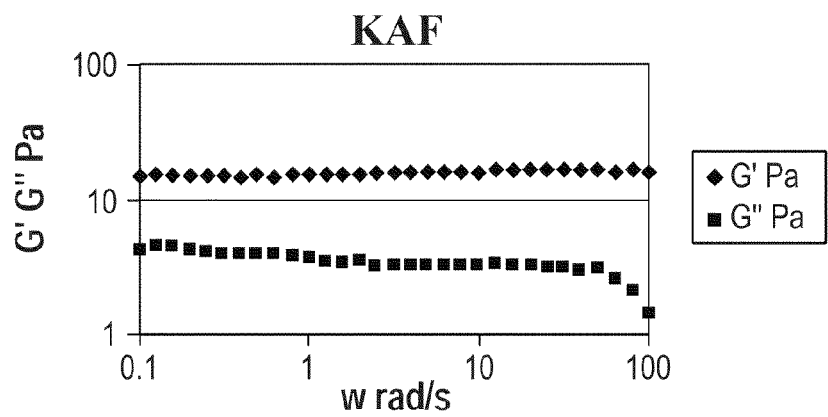
Figure 6G:
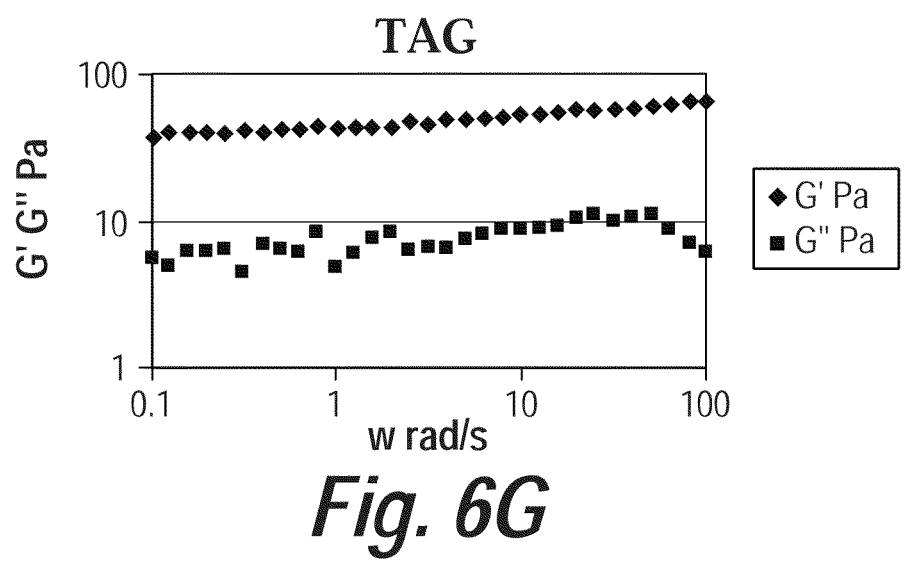
Figure 7A:
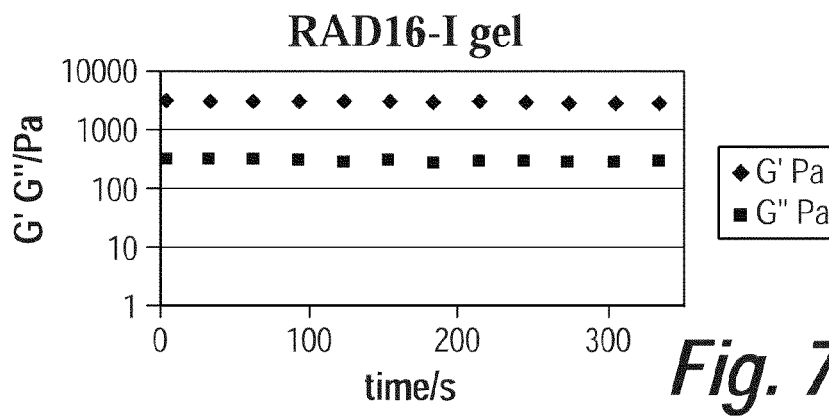
FIGS. 7A-7G show additional physicochemical characterization of peptides RAD16-I, YIG, RYV and TAG by rheology. The plots show a dynamic time sweep test for peptide scaffolds at a fixed frequency of 10 rad/s. G' (storage modulus) represents the elastic character of the material, and G" (loss modulus) represents its viscous character.
Figure 7B:
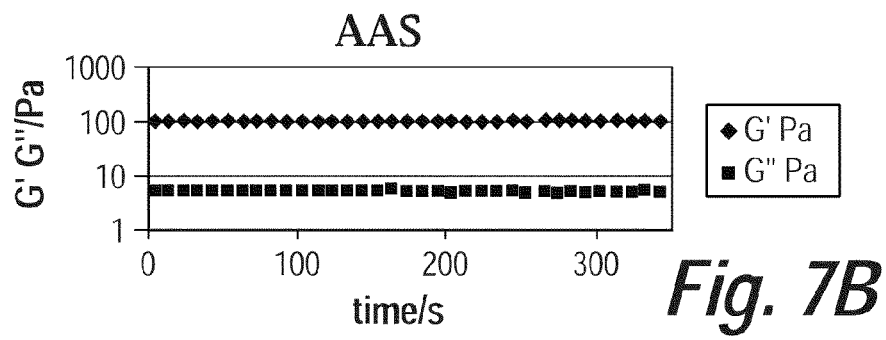
Figure 7C:
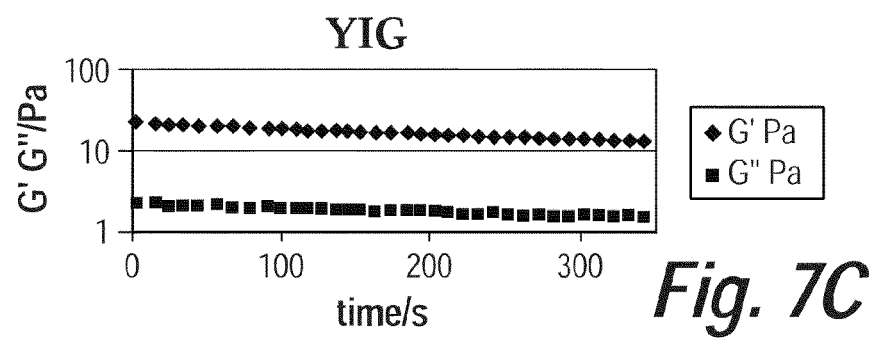
Figure 7D:
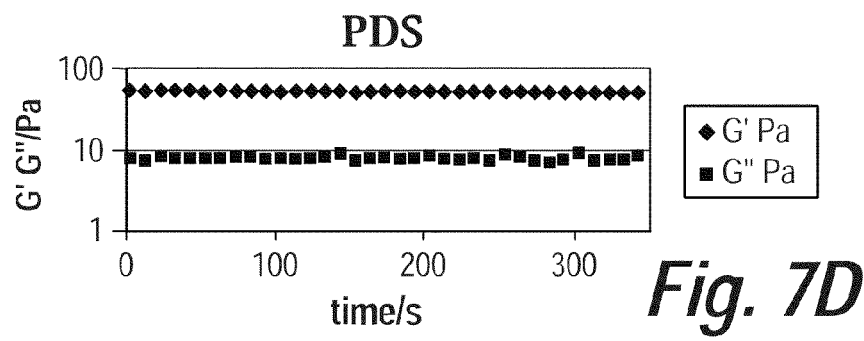
Figure 7E:
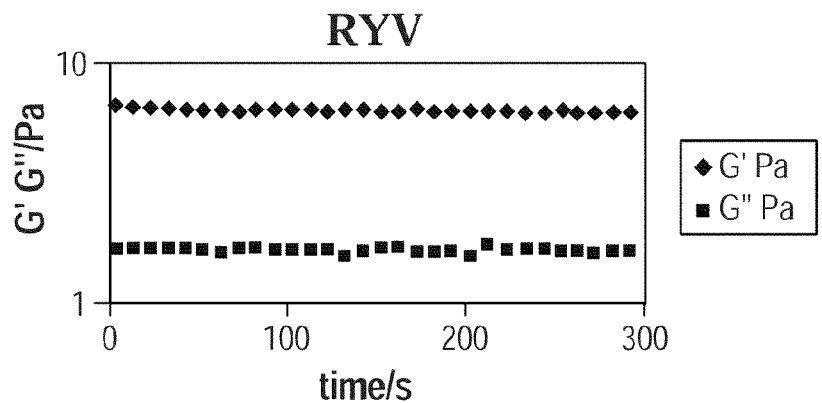
Figure 7F:
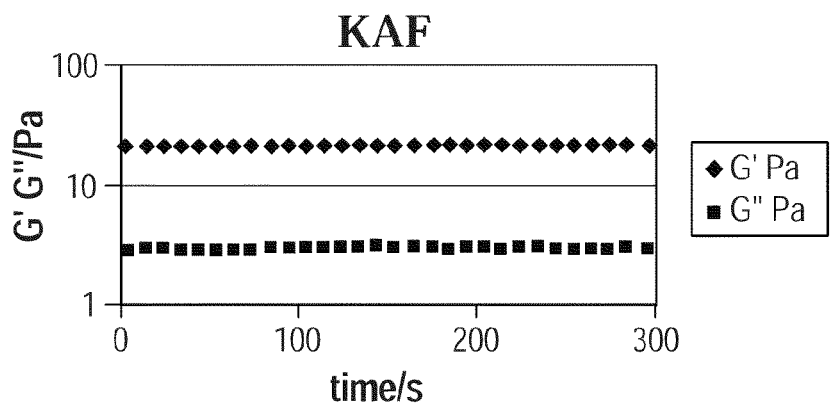
Figure 7G:
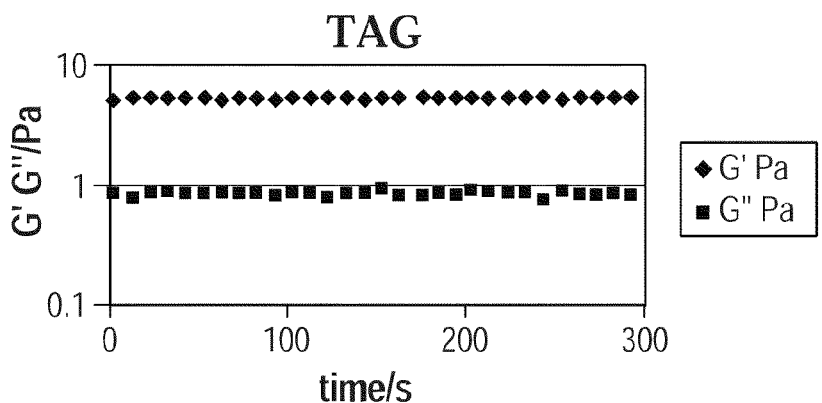

For the modified peptides, assays were performed after the addition of PBS to the peptide solution. Results from rheological measurements of all peptides are shown in FIGS. 6A-6G. As in the case of RAD16-I, G' is greater than G". In the case of the prototypic sequence, RAD16-I, the storage modulus G' reaches $2.5 \times 10^3$ Pa (FIG. 6A). The magnitude for the peptide AAS is about 10 fold lower ($1.5 \times 10^2$ Pa), and about 100 times lower for the rest of the sequences. These results show that the addition of a peptide motif that does not possess the features of alternating hydrophobic and hydrophilic amino acids that are complementary and structurally compatible characteristic of the self-assembling peptides described above may interfere to a certain extent with the self-assembly process. However, addition of such a motif does not, in general, eliminate the ability of the unmodified portion of the peptide to self-assemble, and the modified peptide itself is thus able to self-assemble also. However, the structures formed by the modified peptides are weaker than those resulting from self-assembly of the unmodified peptide. While not wishing to be bound by any theory, this may be due to a possible distortion of the β-sheet configuration of RAD16-I. The fact that a gel behavior is observed by rheometrical assays confirms the visual observation of gel formation (Table 4).

In FIGS. 7A-7G the behavior of the different peptide sequences with time is shown. At the selected frequency (10 rad/s), both moduli G' and G" remain constant with time, indicating that the gel is stable.

Example 2

Endothelial Cell Growth and Monolayer Formation on Peptide Scaffolds

Materials and Methods.

Endothelial cell culture system. Peptide scaffolds (0.5% w/v) were prepared at 100% peptide sequence for RAD16-I or blended with RAD16-I at a radio of 9:1 (RAD16-I: peptide sequence, on a volume/volume basis) for the three other cases (YIG, RYV, and TAG). Each solution was filtered (0.2 μm, Acrodysc filters, 4192, PALL, MI), loaded (30 μl) on top of a cell culture chamber insert (10 mm diameter, 136935, Nalge Nunc International, IL), and allowed to form a layer (average thickness=600 μm). Phosphate Buffer Saline (PBS) (600 μl) was added at the bottom of the well to induce hydrogel formation, and the system was incubated at room temperature for 30 min. PBS was replaced with culture medium, which was then replaced with fresh medium. The scaffolds were incubated for 1 hour with endothelial cell growth media (EGM-2, Cambrex, MD) in a cell culture incubator at 37° C. with 5% $CO_2$.

Meanwhile, human aortic endothelial cells (HAEC) (CC-2535, Cambrex, MD) that had been maintained under standard culture conditions (passage 5-6) were harvested at 80% confluence using trypsin and loaded on top of the preformed peptide scaffolds at a cell density of $8 \times 10^4$ cells/cm$^2$ and cultured in the cell culture incubator at 37° C. with 5% $CO_2$. Cell attachment assays were performed one hour after the initial cell loading. To perform the assays, the covering media was removed, and unattached cells were counted on a hematocytometer. Cell counting was performed by mechanically disrupting the scaffold containing cells by pipetting up and down and then counting cells on a hematocytometer after performing Trypan blue (T 9906, Sigma, Mo.) exclusion assay staining to assess cell viability. In some experiments, for comparison, EC were cultured on inserts coated with Matrigel or collagen (1.5 mg/ml, i.e 0.15%) according to standard protocols.

Competition assays with free soluble peptide sequences. HAEC were cultured as described on peptide scaffods in cell culture inserts as described above. For each scaffold, the corresponding soluble motif sequence, or one of the other motifs not present in the scaffold, was added to the media of HAEC cultures at a final concentration of 400 μg/ml. Half of the media was changed every other day. After the third day of culture, the media was removed, and fresh media without fetal bovine serum (FBS) or ascorbic acid containing 400 μg/ml of each soluble peptide motif was added. The next day, cell numbers were evaluated as described above. Each condition was tested in triplicate.

Cell isolation from peptide scaffolds. For the additional competition experiments, rather than mechanically disrupting disrupting the gels to collect cells from the surface, the gel surface was first gently washed with PBS free of $Mg^{2+}$ and $Ca^{2+}$. The monolayer was then exposed to a 1:1 mix of trypsin (0.25%) and Versene ($Na_4EDTA$) for 20-30 minutes in an incubator at 37° C. The cells were collected (normally more than 90% are floating and very few still attach to the gel surface). Thus the technique uses 0.125% Trypsin/0.125%/0.01% EDTA instead of 0.05% Trypsin/0.02% EDTA as is typically used to harvest cells from standard tissue culture plate. While not wishing to be bound by any theory, it appears that the basement membrane material synthesized by endothelial cells when cultured on the peptid gels results in increased adherence and thus a need to use more Trypsin to separate them from the gels. The concentration of EDTA is reduced in order to minimize cell death. However, including some EDTA is likely to be important because many cell-cell interactions involve calcium and EDTA binds $Ca^{++}$ with high affinity.

Collected cells were counted using the Trypan Blue exclusion technique. Viability was typically on the order of 85-90%.

Results

HAEC attachment and monolayer formation. One aspect of this study was to explore the possibility of obtaining functionalized biomimetic scaffolds that could be used as synthetic basement membrane analogs to culture endothelial cells. Experiments were therefore conducted to assess the ability of the peptide scaffolds to serve as instructive matrices to support growth and function of human aortic endothelial cells (HAEC). Since aortic endothelial cells normally form monolayers that cover the internal surface of blood vessels (arteries, veins, capillaries) and the chambers of the heart, we tested whether the peptide scaffolds would support monolayer formation, a function in which the basement membrane plays an important role in vivo.

In a first experiment, we tested the ability of HAEC to attach and form a monolayer when seeded on various peptide scaffolds generated by self-assembly of the peptides following addition of PBS to a 0.5% (w/v) solution of the peptide in water. In this assay, only one of the modified peptides, YIG, was able to support the formation of a monolayer although monolayer formation was observed when cells were cultured on the unmodified RAD16-I scaffold. HAEC cultured in the presence of scaffolds generated from peptides incorporating the other biologically active peptide motifs either died or formed isolated clusters (FIGS. 9A-9G).

The fact that scaffolds composed entirely of peptides modified to incorporate a biologically active motif did not support monolayer formation suggested that the effect of the biologically active motifs might be concentration dependent. We hypothesized that the presence of the motifs in 100% of the peptides resulted in presentation of too high a concentration to the cells, resulting in cell toxicity. We therefore decided to blend the peptides incorporating biologically active motifs with the prototypic RAD16-I sequence in order to reduce the overall concentration of the biologically active motif presented to cells. We selected a volume/volume ratio of 9:1 (RAD16-I:modified peptide sequence comprising biologically active peptide motif, where peptides were dissolved at equal concentrations on a w/w basis) and generated peptide scaffolds from solutions in which the unmodified and modified peptides were present in this ratio. Based on visual observation of gel formation and features and the characteristics observed during handling and manipulation of the scaffolds, we concluded that the mechanical properties of the composite scaffolds were very similar to those of scaffolds composed entirely of RAD16-I. This finding indicates that the mechanical properties of the scaffolds can be tuned by selecting an appropriate ratio of unmodified to modified peptide.

Cells were seeded at a subconfluent number (~30%) in order to permit good cell-material interaction. We observed that three of the scaffolds made from peptide blends, i.e., peptides in which the modified peptide incorporated YIG, RYV, or TAG, readily supported monolayer formation (Table 5, FIGS. 10A-10D). After one hour, the HAEC attachment to the surface was ~100% for these three scaffolds and RAD16-I, suggesting that the initial interaction of the cells with the material was not affected by the functionalization. We selected these three modified peptides and the unmodified RAD16-I alone to use in the following experiments.

Table 5 summarizes results obtained when the various scaffolds were tested for their ability to support HAEC monolayer formation.

TABLE 5

HAEC monolayer formation on peptide scaffolds.

| Peptide sequence | Peptide content | |
| --- | --- | --- |
| | 100% | Blending (9:1)* |
| RAD16-I | +¶ | |
| AAS | −§ | − |
| YIG | + | + |
| PDS | − | − |
| RYV | − | + |
| KAF | − | − |
| TAG | − | + |

¶(+) Score for optimal monolayer formation and cell survival
§(−) Score for poor or none monolayer formation and cell survival
*RAD16-I:Peptide sequence (at a ratio 9:1)

In other experiments, endothelial monolayer formation on RAD16-I (100%) and the RAD16-I:YIG, RAD16-I:RYV, and RAD16-I:TAG 9:1 blended scaffolds was compared with monolayer formation on Matrigel and collagen-coated substrates. FIGS. 16A-16L show HAEC monolayer formation on the various different gel systems after 3 days in culture. The figure shows phase contrast microscopy images of HAEC seeded on Collagen I gel (A), Matrigel (C), 100% peptide scaffold RAD16-I (E), blending 90% RAD16-I/10% (v/v) YIG (G), blending of 90% RAD16-I/10% (v/v) TAG (I), and blending of 90% RAD16-I/10% (v/v)RYV (J). Fluorescent staining with TRITC Phalloidin and DAPI to detect Actin fibers (yellow) and nucleus (blue), respectively, for A (B), C (D), E (F), G (H), I (J), K (L). Phase contrast images depict a typical cobblestone monolayer also observed with the acting/DAPI staining. As shown in the figure, HAEC cultured on scaffolds composed of the three tested peptide blends can develop a confluent monolayer with cobblestone phenotype in three days of culture, similar to what is seen with Matrigel and collagen I gels. Qualitatively, monolayer formation, morphology, and cell number appeared similar on the modified peptide scaffolds to the appearance on Matrigel or collagen. However, the degree of cobblestone morphology observed on 100% RAD16-I scaffold was less than on blended scaffolds or on Matrigel or collagen-I.

Figure 12A:
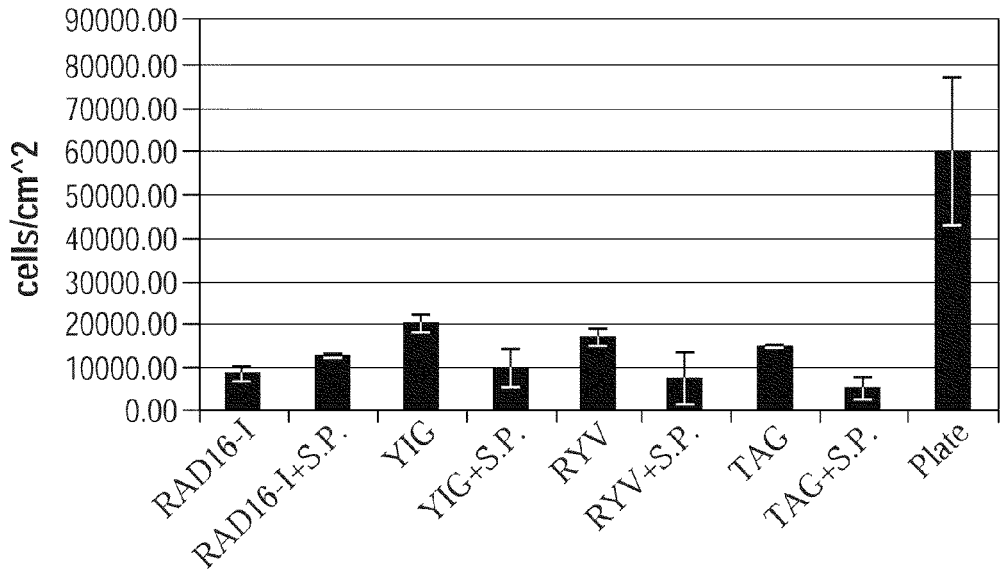
FIG. 12 shows data from a competition assay in which cell proliferation on an RAD16-I peptide scaffold or on peptide scaffolds formed from a 9:1 (v/v) blend of RAD16-I and each of various modified peptides was measured in the absence or presence of the corresponding soluble peptide (S.P.) motif. YIGSR (SEQ ID NO:33) was used as the soluble peptide for addition to cell cultures growing on pure RAD16-I scaffold. A comparison with cells grown on a conventional tissue culture plate is shown. RAD16-I, control peptide scaffold; RAD16-I+S.P, control peptide scaffold with soluble peptide YIGSR (SEQ ID NO:33) (400 µM); YIG, peptide scaffold YIG; YIG+S.P., peptide scaffold YIG with soluble peptide YIGSR (SEQ ID NO:33) (400 µM); RYV, peptide scaffold RYV; RYV+S.P., RYV peptide scaffold with soluble peptide RYVVLPR (SEQ ID NO: 35) (400 µM); TAG, peptide scaffold TAG; TAG+S.P., peptide scaffold TAG with soluble peptide TAGSCLRKFSTM (SEQ ID NO:37) (400 µM). Plate, conventional tissue culture plate with no soluble peptide.
Figure 12B:
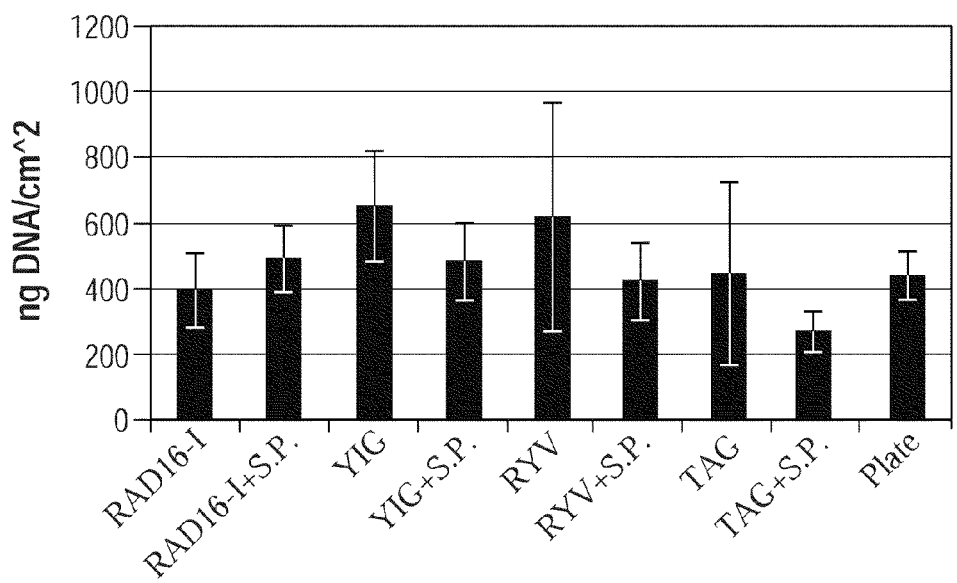
Figure 13:
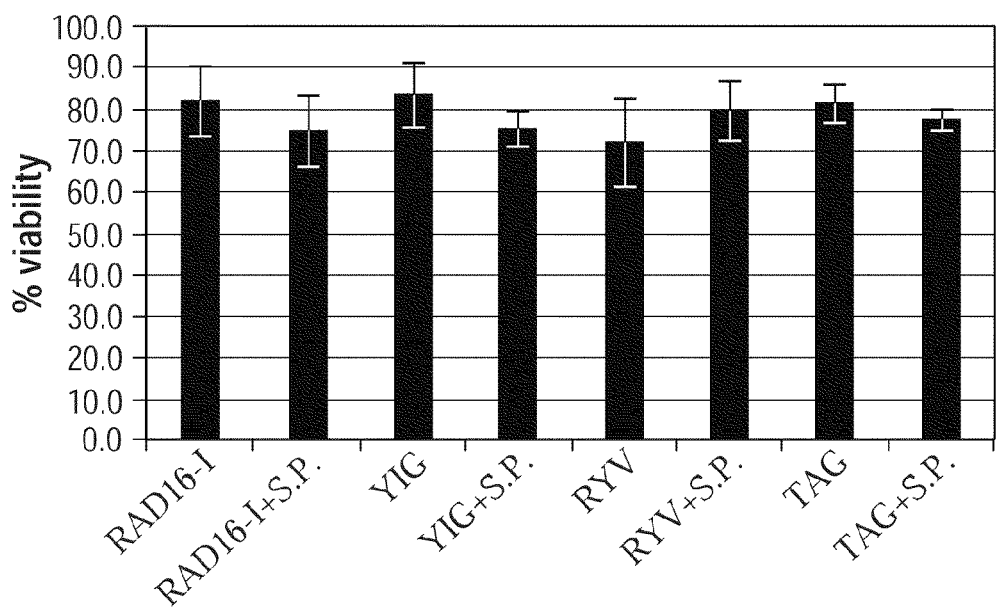
FIG. 13 shows cell viability of HAEC seeded on different peptide scaffolds in the absence or presence of soluble peptide (S.P.). RAD16-I was present at 100%; the other peptide scaffolds were formed from a 9:1 blend of RAD16-I:modified peptide. RAD16-I, control peptide scaffold; RAD16-I+S.P, control peptide scaffold with soluble peptide YIGSR (400 µM); YIG, peptide scaffold YIG; YIG+S.P., peptide scaffold YIG with soluble peptide YIGSR (SEQ ID NO:33) (400 µM); RYV, peptide scaffold RYV; RYV+S.P., RYV peptide scaffold with soluble peptide RYVVLPR (SEQ ID NO:35) (400 µM); TAG, peptide scaffold TAG; TAG+S.P., peptide scaffold TAG with soluble peptide TAGSCLRKFSTM (SEQ ID NO:37) (400 µM).

HAEC proliferation rate. In order to analyze the proliferation rate of HAEC on each scaffold surface, cells were seeded again under subconfluent conditions (~30%) to allow cell growth. After three days of culture, the proliferation rate was increased 2-3 fold on the scaffolds containing modified peptides with respect to the RAD16-I control (FIG. 12). This dramatic change in the proliferation rate accelerated the formation of a confluent monolayer on the modified surfaces, suggesting that the cells may sense and respond to the motif-modified material.

To confirm this idea, competition assays with the free peptide motif were performed in an effort to specifically block the interaction of the cell surface with the modified peptide scaffold. In all cases, soluble peptides YIGSR (SEQ ID NO:33), RYVVLPR (SEQ ID NO:35), and TAGSCLRKFSTM (SEQ ID NO:37) added to the culture medium of the corresponding scaffold (i.e., the scaffold composed of a 9:1 composite of RAD16-I:modified peptide) reduced the proliferation rate to similar levels to those observed on the RAD16-I scaffold, suggesting that the cells specifically recognized the functional sequence present in each of the three modified scaffolds (FIG. 12). Significantly, the cells were instructed through the biomimetic matrix only when the sequence was physically attached to the nanofiber. While not wishing to be bound by any theory, it is plausible that a mechano-signaling transduction event was involved in regulating the proliferation rate of HAEC. It is noted that in all cases tested, the cell density was much smaller than the density of HAEC cultured on conventional tissue culture plates, suggesting that cell proliferation may be reduced when cells are cultured on the scaffolds, relative to proliferation on plastic plates. However, it is likely that the number of cells growing on the scaffolds was underestimated due difficulties associated with cell recovery from the scaffolds. In addition, it is noted that a reduction in proliferation rate is not inconsistent with development of a more differentiated, functional state on the scaffolds, as evidenced by measurement of markers of endothelial cell function (see below). Both proliferation rate and functional state are important parameters in terms of evaluating the ability of a biomimetic culture material to serve as a useful substrate for endothelial cell culture.

Additional competition assays. Further studies were performed in which HAEC were cultured on either RAD16-I scaffold or 9:1 (v/v) blends of RAD16-I with YIG, TAG, or RYV in the presence or absence of either the corresponding biologically active peptide or a different biologically active peptide. Cells were harvested using the improved isolation technique described above, not involving mechanical disruption of the scaffold, in order to maximize cell recovery. The data is presented quantitatively in FIG. 17. As shown in the bar graphs, in the absence of added soluble biologically active peptide, HAEC proliferation on peptide scaffolds made from 100% RAD16-I peptide is significantly lower, by about 2-2.5 fold, than proliferation on scaffolds made from peptide blends. Adding a soluble biologically active peptide to cultures grown on a scaffold containing that peptide reduces HAEC proliferation to approximately the same level as on unmodified RAD16-I scaffolds. Importantly, the data also indicates that when HAEC are cultured on a scaffold containing peptides with a specific biologically active amino acid domain, the competition only reduces cell proliferation when the same amino acid domain is provided in soluble form, in other words, by competing with the same sequence tag on the nanofibers comprising the scaffold. Unfortunately it was almost impossible to recover more than 10% of the cells from Matrigel or collagen I gels because of the tightness with which they attached, and it was therefore not possible to quantitatively compare HAEC proliferation on Matrigel or collagen I with proliferation on the blended scaffolds. However, qualitatively proliferation appeared approximately equivalent for these conditions.

Example 3

Functional Characterization of Endothelial Cells Cultured on Peptide Scaffolds

Materials and Methods

NO release determination. Nitric oxide (NO) release was estimated by measuring nitrites ($NO_x$) by the Griess method. Briefly, the media was replaced after the third day of culture by new media without fetal bovine serum (FBS) or ascorbic acid. The next day, the media was used to analyze NO release using a commercially available kit (482702, Calbiochem, CA) following the manufacturer instructions. Each condition was tested in triplicate.

LDL uptake staining. Cells cultured on scaffolds assembled in 96 well dishes were used to perform cell staining. The scaffolds were assembled by placing peptide solution in the wells, followed addition of media to initiate scaffold formation. Cells were incubated for 4 hours with media containing 8 μg/ml of acetylated low density lipoprotein labeled with 1,1'-dioctadecyl-3,3,3',3'-tetramethylindo-carbocyanine perchlorate (DiI-Ac-LDL, BT-902, Biomedical Technologies Inc, MA). At that time, cells were fixed for 1 hour with 2% paraformaldehyde (PFA), permeabilized for 10 minutes with 0.1% Triton-X 100 and blocked for 1 hour with blocking solution (20% bovine calf serum, 0.1% Triton-x 100 and 1% dimethylsulfoxyde in PBS). DAPI staining (4',6-diamidino-2-phenylindole dihydrochloride, D-1306, Molecular Probes, OR) was used to visualize cell nuclei. Samples were incubated with 10 μg/ml DAPI in PBS for 5 minutes and analyzed under a Nikon Epi-Fluorescence microscope TE300.

Western blots. Harvested HAEC for each culture condition were counted and lysed with sample buffer (NP0007, Invitrogen, CA) containing 2% (v/v) β-mercaptoethanol and a cocktail of protease inhibitors (1836153, Complete Mini, Roche, Penzberg, Germany) to avoid proteolysis. Cell lysates were run on a 10% PAGE system in MOPS buffer (NP0301, NP0001 Invitrogen, CA), and proteins were transferred to PVDF membranes (LC2002, Invitrogen, CA) to perform western blots. Briefly, membranes were blocked with 2% BSA and 0.1% Triton-X 100 in PBS. Two primary antibodies were used: mouse monoclonal $IgG_1$ anti human laminin γ1[laminin B2 chain] (1 μg/ml, B1920, Chemicon, CA) and mouse monoclonal $IgG_1$ anti human collagen IV [7S domain] (2 μg/ml, MAB3326, Chemicon, CA). A secondary antibody, goat polyclonal anti-mouse IgG-HRP conjugated (1:5000 dilution, sc-2302, Santa Cruz Biotechnology, CA) was used for detection by chemiluminescence (sc-2048, Santa Cruz Biotechnology, CA). Protein bands were visualized by exposure to an X-ray film (Biomax Film, Kodak, NY).

Results

FIGS. 11A-11H show low density lipoprotein (LDL) uptake by HAEC and DAPI staining. LDL is a commonly used marker for vascular endothelial cells and confirms that the cell retained their vascular endothelial phenotype on the modified peptide scaffolds. DAPI staining was used to visualize cell nuclei.

Figure 15:
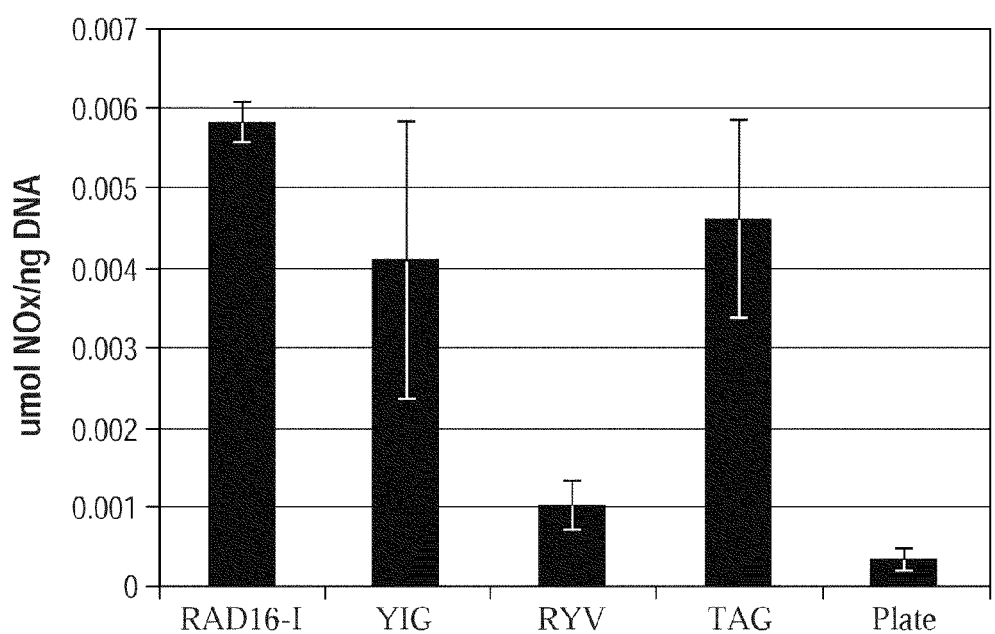
FIG. 15 shows nitric oxide (NO) production of HAEC cultured on different peptide scaffolds and control plate. RAD16-I was present at 100%; the other peptide scaffolds were formed from a 9:1 blend of RAD16-I:modified peptide.

Nitric oxide release. Nitric oxide (NO) release by HAEC was estimated by assessing nitrite ($NO_x$) concentrations in the cell culture supernatants. This parameter also estimates the endothelial cell activity of the HAEC cultured on the various peptide nanofiber scaffolds. These scaffold cultures, except for the functionalized peptide RYV, promote NO release (FIG. 15). Again, this suggests that the peptide hydrogel material in general is a good substrate for culturing endothelial cells. Nevertheless, there was little difference in NO release between the peptide scaffolds RAD16-I, YIG, and TAG. It is possible that in this case the functionalization does not play a crucial role in this particular aspect of endothelial cell phenotype and might suggest that the peptide scaffold RYV inhibits NO release.

Figure 14A:
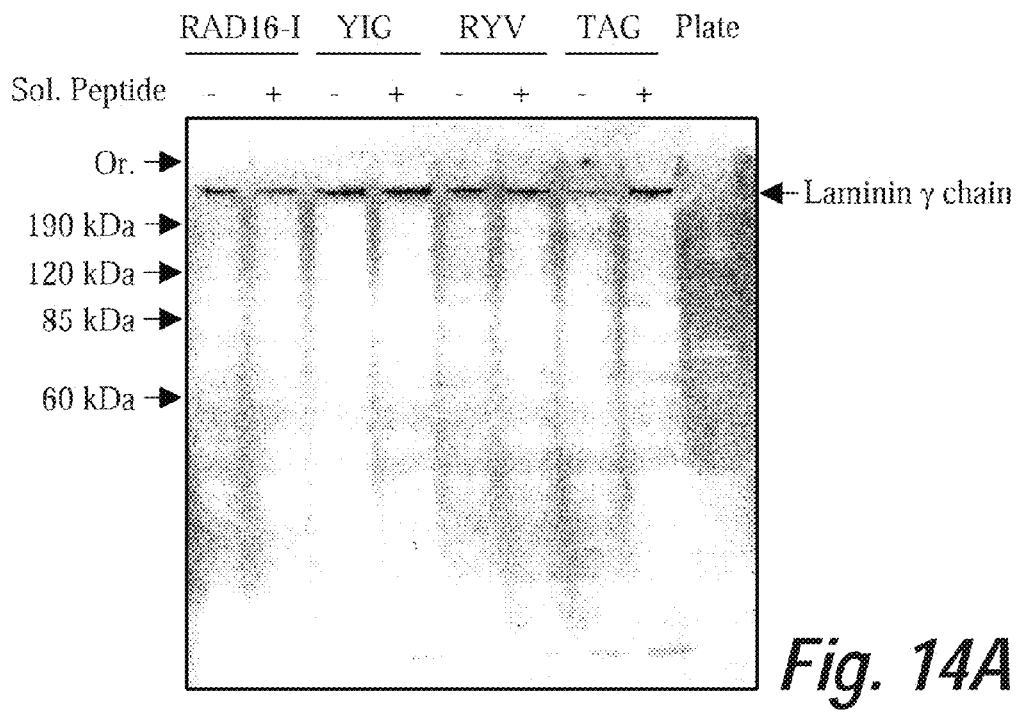
FIGS. 14A-14B show Western blot analysis of (A) Laminin-1 γ chain and (B) collagen IV production by HAEC cultured on different peptide scaffolds in the absence (−) and presence (+) of soluble peptide corresponding to the modification in the peptide or on a control plate. RAD16-I was present at 100%; the other peptide scaffolds were formed from a 9:1 blend of RAD16-I:modified peptide.
Figure 14B:
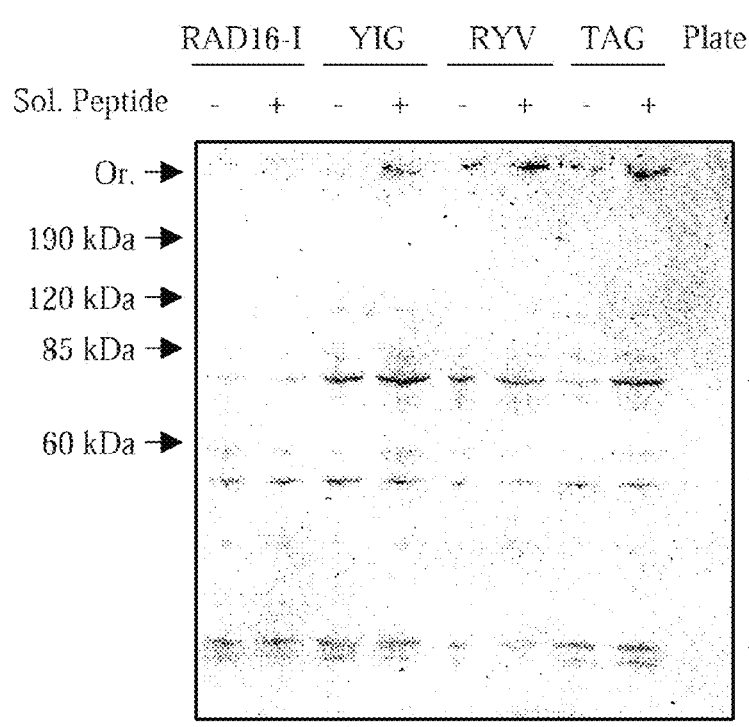

Production of basement membrane components. An important functional assay consisted of characterizing the production of laminin 1 and collagen IV by the HAEC to test the endothelial cell activity on each scaffold by measuring the capacity of the cells to deposit their own basement membrane components. In general, for all conditions tested, including scaffolds made from the unmodified RAD16-I peptide, significant enhancement of laminin 1 and collagen IV deposition was observed when compared to conventional 2D tissue culture plates (FIGS. 14A and 14B). Interestingly, only one band for laminin 1 (β2 chain) was observed while two bands of smaller molecular weight for collagen IV were observed, suggesting that the collagen molecule may be partially degraded under the culture conditions tested while the laminin molecule appears to be intact. These results suggest that the deposited basement membrane components may be selectively undergoing remodeling, as shown by the partial degradation of the collagen IV molecule component only.

We claim:

1. A self-assembling peptide comprising:
   (a) a first amino acid domain that mediates self-assembly, wherein the domain comprises a sequence of alternating hydrophobic and hydrophilic amino acids that are complementary and structurally compatible, and that self-assemble into a macroscopic structure when present in unmodified form, which sequence is selected from the group consisting of: SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 14, SEQ ID NO: 15, SEQ ID NO: 16, and SEQ ID NO: 18; and
   b) a second amino acid domain that does not self-assemble in isolated form,
   wherein the first and second amino acid domains are joined by a single peptide bond;
   wherein the peptide self-assembles when present as the only peptide in a solution; and
   wherein the total number of amino acids comprising the self-assembling peptide is less than 36 amino acids.

2. The self-assembling peptide of claim 1 wherein the second amino acid domain comprises a biologically active peptide motif or a target site for an interaction with a biomolecule.

3. The self-assembling peptide of claim 2, wherein the sequence of the second amino acid domain comprises a sequence selected from the group consisting of: SEQ ID NO: 31, SEQ ID NO: 33, SEQ ID NO: 34, SEQ ID NO: 35, SEQ ID NO: 36, and SEQ ID NO: 37.

4. The self-assembling peptide of claim 1, wherein the peptide is linear.

5. The self-assembling peptide of claim 1, wherein the first amino acid domain comprises multiple RADA (SEQ ID NO: 4) peptide subunits.

6. The self-assembling peptide of claim 1, wherein the total number of amino acids comprising the second amino acid domain is less than 20 amino acids.

7. The self-assembling peptide of claim 1, wherein the total number of amino acids comprising the second amino acid domain is less than 12 amino acids.

8. The self-assembling peptide of claim 1, wherein the total number of amino acids comprising the second amino acid domain is less than 7 amino acids.

9. The self-assembling peptide of claim 1, wherein the total number of amino acids comprising the second amino acid domain is less than 5 amino acids.

10. The self-assembling peptide of claim 1, wherein the first amino acid domain comprises RADA16-I peptide.

11. The self-assembling peptide of claim 1, wherein the peptide self-assembles to form a hydrogel.

12. The self-assembling peptide of claim 1, further comprising a third amino acid domain joined by a peptide bond to the first amino acid domain.

13. The self-assembling peptide of claim 1, further comprising a third amino acid domain joined by a peptide bond to the second amino acid domain.

14. A self-assembling peptide comprising:
   (a) a first amino acid domain that mediates self-assembly, wherein the domain comprises a sequence of alternating hydrophobic and hydrophilic amino acids that are complementary and structurally compatible, and that self-assemble into a macroscopic structure when present in unmodified form, which sequence is selected from the group consisting of: SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 14, SEQ ID NO: 15, SEQ ID NO: 16, and SEQ ID NO: 18; and
   b) a second amino acid domain that does not self-assemble in isolated form,
   wherein the first and second amino acid domains are joined by a linker domain,
   wherein the peptide self-assembles when present as the only peptide in a solution; and
   wherein the total number of amino acids comprising the self-assembling peptide is less than about 36 amino acids.

15. The self-assembling peptide of claim 14, wherein the linker domain is between 1 and 4 amino acids.

16. The self-assembling peptide of claim 14, wherein the linker domain is between 1 and 4 glycine residues.

17. The self-assembling peptide of claim 14, wherein the linker domain comprises one or more glycine residues.

18. The self-assembling peptide of claim 14, wherein the first amino acid domain comprises multiple RADA (SEQ ID NO: 4) peptide subunits.

19. The self-assembling peptide of claim 14, wherein the total number of amino acids comprising the second amino acid domain is less than 20 amino acids.

20. The self-assembling peptide of claim 14, wherein the total number of amino acids comprising the second amino acid domain is less than 12 amino acids.

21. The self-assembling peptide of claim 14, wherein the total number of amino acids comprising the second amino acid domain is less than 7 amino acids.

22. The self-assembling peptide of claim 14, wherein the total number of amino acids comprising the second amino acid domain is less than 5 amino acids.

23. The self-assembling peptide of claim 14, wherein the first amino acid domain comprises RADA16-I peptide.

24. The self-assembling peptide of claim 14, wherein the peptide self-assembles to form a hydrogel.

25. The self-assembling peptide of claim 14, further comprising a third amino acid domain joined by a peptide bond to the first amino acid domain.

26. The self-assembling peptide of claim 14, further comprising a third amino acid domain joined by a peptide bond to the second amino acid domain.

27. The self-assembling peptide of claim 2, wherein the sequence of the second amino acid domain comprises a sequence selected from the group consisting of: SEQ ID NO: 31, SEQ ID NO: 34, SEQ ID NO: 35, SEQ ID NO: 36, and SEQ ID NO: 37.

28. The self-assembling peptide of claim 14, wherein the sequence of the second amino acid domain comprises a sequence selected from the group consisting of: SEQ ID NO: 31, SEQ ID NO: 34, SEQ ID NO: 35, SEQ ID NO: 36, and SEQ ID NO: 37.

29. The self-assembling peptide of claim 1 having the sequence AcN-RYVVLPR-GG-(RADA)$_4$-CONH$_2$ (SEQ ID NO: 43).

30. A self-assembling peptide comprising:
(a) a first amino acid domain that mediates self-assembly, wherein the domain comprises alternating hydrophobic and hydrophilic amino acids that are complementary and structurally compatible, and that self-assemble into a macroscopic structure when present in unmodified form, which sequence is SEQ ID NO: 4 (RAD 16-I); and
(b) a second amino acid domain, wherein the sequence of the second amino acid domain comprises SEQ ID NO: 35 (RYVVLPR); and
Wherein the peptide forms a beta sheet upon self-assembly.

* * * * *

SEQUENCE LISTING

```
<160> NUMBER OF SEQ ID NOS: 68

<210> SEQ ID NO 1
<211> LENGTH: 16
<212> TYPE: PRT
<213> ORGANISM: Artificial Sequence
<220> FEATURE:
<223> OTHER INFORMATION: From self-assembling peptide - invented
      sequence.

<400> SEQUENCE: 1

Arg Ala Asp Ala Arg Ala Asp Ala Arg Ala Asp Ala Arg Ala Asp Ala
1               5                   10                  15
```

```
<210> SEQ ID NO 2
<211> LENGTH: 16
<212> TYPE: PRT
<213> ORGANISM: Artificial Sequence
<220> FEATURE:
<223> OTHER INFORMATION: From Self-Assembling peptide - invented
      sequence

<400> SEQUENCE: 2

Arg Ala Asp Ala Arg Gly Asp Ala Arg Ala Asp Ala Arg Gly Asp Ala
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: From Self-Assembling peptide - invented
      sequence.

<400> SEQUENCE: 3

Arg Ala Asp Ala Arg Ala Asp Ala
1               5

<210> SEQ ID NO 4
<211> LENGTH: 16
<212> TYPE: PRT
<213> ORGANISM: Artificial Sequence
<220> FEATURE:
<223> OTHER INFORMATION: From Self-Assembling peptide - invented
      sequence.

<400> SEQUENCE: 4

Arg Ala Arg Ala Asp Ala Asp Ala Arg Ala Arg Ala Asp Ala Asp Ala
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: From Self-Assembling peptide - invented
      sequence.

<400> SEQUENCE: 5

Arg Ala Arg Ala Asp Ala Asp Ala
1               5

<210> SEQ ID NO 6
<211> LENGTH: 20
<212> TYPE: PRT
<213> ORGANISM: Artificial Sequence
<220> FEATURE:
<223> OTHER INFORMATION: From Self-Assembling peptide - invented
      sequence.

<400> SEQUENCE: 6

Ala Glu Ala Lys Ala Glu Ala Lys Ala Glu Ala Lys Ala Glu Ala Lys
1               5                   10                  15

Ala Glu Ala Lys
            20

<210> SEQ ID NO 7
<211> LENGTH: 8
<212> TYPE: PRT
<213> ORGANISM: Artificial Sequence
<220> FEATURE:
```

```
<223> OTHER INFORMATION: From self-assembling peptide - invented
      sequence.

<400> SEQUENCE: 7

Ala Glu Ala Lys Ala Glu Ala Lys
1               5

<210> SEQ ID NO 8
<211> LENGTH: 16
<212> TYPE: PRT
<213> ORGANISM: Artificial Sequence
<220> FEATURE:
<223> OTHER INFORMATION: From self-assembling peptide - invented
      sequence.

<400> SEQUENCE: 8

Arg Ala Glu Ala Arg Ala Glu Ala Arg Ala Glu Ala Arg Ala Glu Ala
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: From self-assembling peptide

<400> SEQUENCE: 9

Arg Ala Glu Ala Arg Ala Glu Ala
1               5

<210> SEQ ID NO 10
<211> LENGTH: 16
<212> TYPE: PRT
<213> ORGANISM: Artificial Sequence
<220> FEATURE:
<223> OTHER INFORMATION: From self-assembling peptide

<400> SEQUENCE: 10

Lys Ala Asp Ala Lys Ala Asp Ala Lys Ala Asp Ala Lys Ala Asp Ala
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: From self-assembling peptide

<400> SEQUENCE: 11

Lys Ala Asp Ala Lys Ala Asp Ala
1               5

<210> SEQ ID NO 12
<211> LENGTH: 16
<212> TYPE: PRT
<213> ORGANISM: Artificial Sequence
<220> FEATURE:
<223> OTHER INFORMATION: From self-assembling peptide

<400> SEQUENCE: 12

Ala Glu Ala Glu Ala His Ala His Ala Glu Ala Glu Ala His Ala His
1               5                   10                  15

<210> SEQ ID NO 13
<211> LENGTH: 8
<212> TYPE: PRT
<213> ORGANISM: Artificial Sequence
```

```
<220> FEATURE:
<223> OTHER INFORMATION: From self-assembling peptide - invented
      sequence.

<400> SEQUENCE: 13

Ala Glu Ala Glu Ala His Ala His
1               5

<210> SEQ ID NO 14
<211> LENGTH: 16
<212> TYPE: PRT
<213> ORGANISM: Artificial Sequence
<220> FEATURE:
<223> OTHER INFORMATION: From self-assembling peptide - invented
      sequence.

<400> SEQUENCE: 14

Phe Glu Phe Glu Phe Lys Phe Lys Phe Glu Phe Glu Phe Lys Phe Lys
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: From self-assembling peptide - invented
      sequence.

<400> SEQUENCE: 15

Phe Glu Phe Lys Phe Glu Phe Lys
1               5

<210> SEQ ID NO 16
<211> LENGTH: 16
<212> TYPE: PRT
<213> ORGANISM: Artificial Sequence
<220> FEATURE:
<223> OTHER INFORMATION: From self-assembling peptide - invented
      sequence.

<400> SEQUENCE: 16

Leu Glu Leu Glu Leu Lys Leu Lys Leu Glu Leu Glu Leu Lys Leu Lys
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: From self-assembling peptide - invented
      sequence.

<400> SEQUENCE: 17

Leu Glu Leu Glu Leu Lys Leu Lys
1               5

<210> SEQ ID NO 18
<211> LENGTH: 16
<212> TYPE: PRT
<213> ORGANISM: Artificial Sequence
<220> FEATURE:
<223> OTHER INFORMATION: From self-assembling peptide - invented
      sequence.

<400> SEQUENCE: 18

Ala Glu Ala Glu Ala Lys Ala Lys Ala Glu Ala Glu Ala Lys Ala Lys
1               5                   10                  15
```

```
<210> SEQ ID NO 19
<211> LENGTH: 12
<212> TYPE: PRT
<213> ORGANISM: Artificial Sequence
<220> FEATURE:
<223> OTHER INFORMATION: From self-assembling peptide - invented
      sequence.

<400> SEQUENCE: 19

Ala Glu Ala Glu Ala Glu Ala Glu Ala Lys Ala Lys
1               5                   10

<210> SEQ ID NO 20
<211> LENGTH: 8
<212> TYPE: PRT
<213> ORGANISM: Artificial Sequence
<220> FEATURE:
<223> OTHER INFORMATION: From self-assembling peptide - invented
      sequence.

<400> SEQUENCE: 20

Ala Glu Ala Glu Ala Lys Ala Lys
1               5

<210> SEQ ID NO 21
<211> LENGTH: 16
<212> TYPE: PRT
<213> ORGANISM: Artificial Sequence
<220> FEATURE:
<223> OTHER INFORMATION: From self-assembling peptide - invented
      sequence.

<400> SEQUENCE: 21

Lys Ala Lys Ala Lys Ala Lys Ala Glu Ala Glu Ala Glu Ala Glu Ala
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: From self-assembling peptide - invented
      sequence.

<400> SEQUENCE: 22

Ala Glu Ala Glu Ala Glu Ala Glu Ala Lys Ala Lys Ala Lys Ala Lys
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: From self-assembling peptide - invented
      sequence.

<400> SEQUENCE: 23

Arg Ala Arg Ala Arg Ala Arg Ala Asp Ala Asp Ala Asp Ala Asp Ala
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: From self-assembling peptide - invented
      sequence.
```

```
<400> SEQUENCE: 24

Ala Asp Ala Asp Ala Asp Ala Asp Ala Arg Ala Arg Ala Arg Ala Arg
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: From self-assembling peptide - invented
      sequence.

<400> SEQUENCE: 25

Asp Ala Asp Ala Asp Ala Asp Ala Arg Ala Arg Ala Arg Ala Arg Ala
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: From self-assembling peptide - invented
      sequence.

<400> SEQUENCE: 26

Ala Asp Ala Asp Ala Asp Ala Asp Ala Arg Ala Arg Ala Arg Ala Arg
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: From self-assembling peptide - invented
      sequence.

<400> SEQUENCE: 27

His Glu His Glu His Lys His Lys His Glu His Glu His Lys His Lys
1               5                   10                  15

<210> SEQ ID NO 28
<211> LENGTH: 8
<212> TYPE: PRT
<213> ORGANISM: Artificial Sequence
<220> FEATURE:
<223> OTHER INFORMATION: From self-assembling peptide - invented
      sequence.

<400> SEQUENCE: 28

His Glu His Glu His Lys His Lys
1               5

<210> SEQ ID NO 29
<211> LENGTH: 20
<212> TYPE: PRT
<213> ORGANISM: Artificial Sequence
<220> FEATURE:
<223> OTHER INFORMATION: From self-assembling peptide - invented
      sequence.

<400> SEQUENCE: 29

Val Glu Val Glu Val Glu Val Glu Val Glu Val Glu Val Glu Val Glu
1               5                   10                  15

Val Glu Val Glu
            20
```

```
<210> SEQ ID NO 30
<211> LENGTH: 22
<212> TYPE: PRT
<213> ORGANISM: Artificial Sequence
<220> FEATURE:
<223> OTHER INFORMATION: From self-assembling peptide - invented
      sequence.

<400> SEQUENCE: 30

Arg Phe Arg Phe Arg Phe Arg Phe Arg Phe Arg Phe Arg Phe Arg Phe
1               5                   10                  15

Arg Phe Arg Phe Arg Phe
            20

<210> SEQ ID NO 31
<211> LENGTH: 12
<212> TYPE: PRT
<213> ORGANISM: Artificial Sequence
<220> FEATURE:
<223> OTHER INFORMATION: From laminin alpha chain peptide - various
      mammalian species.

<400> SEQUENCE: 31

Ala Ala Ser Ile Lys Val Ala Val Ser Ala Asp Arg
1               5                   10

<210> SEQ ID NO 32
<211> LENGTH: 19
<212> TYPE: PRT
<213> ORGANISM: Artificial Sequence
<220> FEATURE:
<223> OTHER INFORMATION: From laminin alpha chain peptide - various
      mammalian species.

<400> SEQUENCE: 32

Cys Ser Arg Ala Arg Lys Gln Ala Ala Ser Ile Lys Val Ala Val Ser
1               5                   10                  15

Ala Asp Arg

<210> SEQ ID NO 33
<211> LENGTH: 5
<212> TYPE: PRT
<213> ORGANISM: Artificial Sequence
<220> FEATURE:
<223> OTHER INFORMATION: From laminin beta1 peptide - various mammalian
      species.

<400> SEQUENCE: 33

Tyr Ile Gly Ser Arg
1               5

<210> SEQ ID NO 34
<211> LENGTH: 5
<212> TYPE: PRT
<213> ORGANISM: Artificial Sequence
<220> FEATURE:
<223> OTHER INFORMATION: From laminin-1 gamma chain peptide - various
      mammalian species.

<400> SEQUENCE: 34

Pro Asp Ser Gly Arg
1               5

<210> SEQ ID NO 35
<211> LENGTH: 7
<212> TYPE: PRT
<213> ORGANISM: Artificial Sequence
```

```
<220> FEATURE:
<223> OTHER INFORMATION: From laminin beta1 peptide - various mammalian
      species.

<400> SEQUENCE: 35

Arg Tyr Val Val Leu Pro Arg
1               5

<210> SEQ ID NO 36
<211> LENGTH: 12
<212> TYPE: PRT
<213> ORGANISM: Artificial Sequence
<220> FEATURE:
<223> OTHER INFORMATION: From laminin-1 gamma chain peptide - various
      mammalian species

<400> SEQUENCE: 36

Lys Ala Phe Asp Ile Thr Tyr Val Arg Leu Lys Phe
1               5                   10

<210> SEQ ID NO 37
<211> LENGTH: 12
<212> TYPE: PRT
<213> ORGANISM: Artificial Sequence
<220> FEATURE:
<223> OTHER INFORMATION: From collagen IV - various mammalian species.

<400> SEQUENCE: 37

Thr Ala Gly Ser Cys Leu Arg Lys Phe Ser Thr Met
1               5                   10

<210> SEQ ID NO 38
<211> LENGTH: 16
<212> TYPE: PRT
<213> ORGANISM: Artificial Sequence
<220> FEATURE:
<223> OTHER INFORMATION: From self-assembling peptide.

<400> SEQUENCE: 38

Arg Ala Asp Ala Arg Ala Asp Ala Arg Ala Asp Ala Arg Ala Asp Ala
1               5                   10                  15

<210> SEQ ID NO 39
<211> LENGTH: 26
<212> TYPE: PRT
<213> ORGANISM: Artificial Sequence
<220> FEATURE:
<223> OTHER INFORMATION: From self-assembling peptide with short motif
      from laminin.

<400> SEQUENCE: 39

Ala Ala Ser Ile Lys Val Ala Val Gly Gly Arg Ala Asp Ala Arg Ala
1               5                   10                  15

Asp Ala Arg Ala Asp Ala Arg Ala Asp Ala
            20                  25

<210> SEQ ID NO 40
<211> LENGTH: 33
<212> TYPE: PRT
<213> ORGANISM: Artificial Sequence
<220> FEATURE:
<223> OTHER INFORMATION: From self-assembling peptide with short motif
      from laminin.

<400> SEQUENCE: 40

Cys Ser Arg Ala Arg Lys Gln Ala Ala Ser Ile Lys Val Ala Val Gly
1               5                   10                  15
```

```
Gly Arg Ala Asp Ala Arg Ala Asp Ala Arg Ala Asp
        20                  25                  30

Ala

<210> SEQ ID NO 41
<211> LENGTH: 23
<212> TYPE: PRT
<213> ORGANISM: Artificial Sequence
<220> FEATURE:
<223> OTHER INFORMATION: From self-assembling peptide with short motif
      from laminin beta

<400> SEQUENCE: 41

Tyr Ile Gly Ser Arg Gly Gly Arg Ala Asp Ala Arg Ala Asp Ala Arg
1               5                   10                  15

Ala Asp Ala Arg Ala Asp Ala
            20

<210> SEQ ID NO 42
<211> LENGTH: 23
<212> TYPE: PRT
<213> ORGANISM: Artificial Sequence
<220> FEATURE:
<223> OTHER INFORMATION: From self-assembling peptide with short motif
      from laminin

<400> SEQUENCE: 42

Pro Asp Ser Gly Arg Gly Gly Arg Ala Asp Ala Arg Ala Asp Ala Arg
1               5                   10                  15

Ala Asp Ala Arg Ala Asp Ala
            20

<210> SEQ ID NO 43
<211> LENGTH: 25
<212> TYPE: PRT
<213> ORGANISM: Artificial Sequence
<220> FEATURE:
<223> OTHER INFORMATION: From self-assembling peptide with short motif
      from laminin beta

<400> SEQUENCE: 43

Arg Tyr Val Val Leu Pro Arg Gly Gly Arg Ala Asp Ala Arg Ala Asp
1               5                   10                  15

Ala Arg Ala Asp Ala Arg Ala Asp Ala
            20                  25

<210> SEQ ID NO 44
<211> LENGTH: 30
<212> TYPE: PRT
<213> ORGANISM: Artificial Sequence
<220> FEATURE:
<223> OTHER INFORMATION: From self-assembling peptide with short motif
      from laminin gamma 1

<400> SEQUENCE: 44

Lys Ala Phe Asp Ile Thr Tyr Val Arg Leu Lys Phe Gly Gly Arg Ala
1               5                   10                  15

Asp Ala Arg Ala Asp Ala Arg Ala Asp Ala Arg Ala Asp Ala
            20                  25                  30

<210> SEQ ID NO 45
<211> LENGTH: 30
<212> TYPE: PRT
<213> ORGANISM: Artificial Sequence
```

```
<220> FEATURE:
<223> OTHER INFORMATION: From self-assembling peptide with short motif
      from collagen IV.

<400> SEQUENCE: 45

Thr Ala Gly Ser Cys Leu Arg Lys Phe Ser Thr Met Gly Gly Arg Ala
1               5                   10                  15

Asp Ala Arg Ala Asp Ala Arg Ala Asp Ala Arg Ala Asp Ala
            20                  25                  30

<210> SEQ ID NO 46
<211> LENGTH: 16
<212> TYPE: PRT
<213> ORGANISM: Artificial Sequence
<220> FEATURE:
<223> OTHER INFORMATION: From self-assermbling peptide - invented
      sequence.

<400> SEQUENCE: 46

Arg Ala Asp Ala Arg Ala Asp Ala Arg Ala Asp Ala Arg Ala Asp Ala
1               5                   10                  15

<210> SEQ ID NO 47
<211> LENGTH: 12
<212> TYPE: PRT
<213> ORGANISM: Artificial Sequence
<220> FEATURE:
<223> OTHER INFORMATION: From self-assermbling peptide - invented
      sequence.

<400> SEQUENCE: 47

Lys Leu Asp Leu Lys Leu Asp Leu Lys Leu Asp Leu
1               5                   10

<210> SEQ ID NO 48
<211> LENGTH: 5
<212> TYPE: PRT
<213> ORGANISM: Artificial Sequence
<220> FEATURE:
<223> OTHER INFORMATION: From laminin - various mammalian species.

<400> SEQUENCE: 48

Ile Lys Val Ala Val
1               5

<210> SEQ ID NO 49
<211> LENGTH: 10
<212> TYPE: PRT
<213> ORGANISM: Artificial Sequence
<220> FEATURE:
<223> OTHER INFORMATION: From laminin gamma chain - various mammalian
      species.

<400> SEQUENCE: 49

Arg Asn Ile Ala Glu Ile Ile Lys Asp Ile
1               5                   10

<210> SEQ ID NO 50
<211> LENGTH: 4
<212> TYPE: PRT
<213> ORGANISM: Artificial Sequence
<220> FEATURE:
<223> OTHER INFORMATION: From laminin gamma chain - various mammalian
      species.

<400> SEQUENCE: 50

Tyr Val Arg Leu
```

```
<210> SEQ ID NO 51
<211> LENGTH: 6
<212> TYPE: PRT
<213> ORGANISM: Artificial Sequence
<220> FEATURE:
<223> OTHER INFORMATION: From laminin gamma chain - various mammalian
      species.

<400> SEQUENCE: 51

Ile Arg Val Thr Leu Asn
1               5

<210> SEQ ID NO 52
<211> LENGTH: 8
<212> TYPE: PRT
<213> ORGANISM: Artificial Sequence
<220> FEATURE:
<223> OTHER INFORMATION: From laminin gamma chain - various mammalian
      species.

<400> SEQUENCE: 52

Thr Thr Val Lys Tyr Ile Phe Arg
1               5

<210> SEQ ID NO 53
<211> LENGTH: 8
<212> TYPE: PRT
<213> ORGANISM: Artificial Sequence
<220> FEATURE:
<223> OTHER INFORMATION: From laminin gamma chain - various mammalian
      species.

<400> SEQUENCE: 53

Ser Ile Lys Ile Arg Gly Thr Tyr
1               5

<210> SEQ ID NO 54
<211> LENGTH: 13
<212> TYPE: PRT
<213> ORGANISM: Artificial Sequence
<220> FEATURE:
<223> OTHER INFORMATION: From laminin alpha chain - various mammalian
      species.

<400> SEQUENCE: 54

Arg Gln Val Phe Gln Val Ala Tyr Ile Ile Ile Lys Ala
1               5                   10

<210> SEQ ID NO 55
<211> LENGTH: 10
<212> TYPE: PRT
<213> ORGANISM: Artificial Sequence
<220> FEATURE:
<223> OTHER INFORMATION: From laminin alpha chain - various mammalian
      species.

<400> SEQUENCE: 55

Phe Gln Ile Ala Tyr Val Ile Val Lys Ala
1               5                   10

<210> SEQ ID NO 56
<211> LENGTH: 13
<212> TYPE: PRT
<213> ORGANISM: Artificial Sequence
<220> FEATURE:
<223> OTHER INFORMATION: From laminin alpha chain - various mammalian
```

```
               species.

<400> SEQUENCE: 56

Gly Gln Leu Phe His Val Ala Tyr Ile Ile Ile Lys Ala
1               5                   10

<210> SEQ ID NO 57
<211> LENGTH: 10
<212> TYPE: PRT
<213> ORGANISM: Artificial Sequence
<220> FEATURE:
<223> OTHER INFORMATION: From laminin alpha chain - various mammalian
      species.

<400> SEQUENCE: 57

Phe His Val Ala Tyr Val Leu Ile Lys Ala
1               5                   10

<210> SEQ ID NO 58
<211> LENGTH: 13
<212> TYPE: PRT
<213> ORGANISM: Artificial Sequence
<220> FEATURE:
<223> OTHER INFORMATION: From laminin alpha chain - various mammalian
      species.

<400> SEQUENCE: 58

Leu Glu Asn Gly Glu Ile Val Ser Leu Val Asn Gly Arg
1               5                   10

<210> SEQ ID NO 59
<211> LENGTH: 4
<212> TYPE: PRT
<213> ORGANISM: Artificial Sequence
<220> FEATURE:
<223> OTHER INFORMATION: From fibronectin - various mammalian species.

<400> SEQUENCE: 59

Arg Glu Asp Val
1

<210> SEQ ID NO 60
<211> LENGTH: 6
<212> TYPE: PRT
<213> ORGANISM: Artificial Sequence
<220> FEATURE:
<223> OTHER INFORMATION: From elastin - various mammalian species.

<400> SEQUENCE: 60

Leu Gly Thr Ile Pro Gly
1               5

<210> SEQ ID NO 61
<211> LENGTH: 4
<212> TYPE: PRT
<213> ORGANISM: Artificial Sequence
<220> FEATURE:
<223> OTHER INFORMATION: From collagen I - various mammalian species.

<400> SEQUENCE: 61

Asp Gly Glu Ala
1

<210> SEQ ID NO 62
<211> LENGTH: 5
<212> TYPE: PRT
<213> ORGANISM: Artificial Sequence
```

```
<220> FEATURE:
<223> OTHER INFORMATION: From elastin - various mammalian species.

<400> SEQUENCE: 62

Gly Val Gly Val Pro
1               5

<210> SEQ ID NO 63
<211> LENGTH: 6
<212> TYPE: PRT
<213> ORGANISM: Artificial Sequence
<220> FEATURE:
<223> OTHER INFORMATION: From elastin - various mammalian species.

<400> SEQUENCE: 63

Gly Val Gly Val Ala Pro
1               5

<210> SEQ ID NO 64
<211> LENGTH: 13
<212> TYPE: PRT
<213> ORGANISM: Artificial Sequence
<220> FEATURE:
<223> OTHER INFORMATION: From Collagen IV

<400> SEQUENCE: 64

Leu Ala Gly Ser Cys Leu Ser Ala Arg Phe Ser Thr Met
1               5                   10

<210> SEQ ID NO 65
<211> LENGTH: 12
<212> TYPE: PRT
<213> ORGANISM: Artificial Sequence
<220> FEATURE:
<223> OTHER INFORMATION: From collagen IV

<400> SEQUENCE: 65

Gly Glu Phe Tyr Asp Leu Arg Leu Lys Gly Asp Lys
1               5                   10

<210> SEQ ID NO 66
<211> LENGTH: 8
<212> TYPE: PRT
<213> ORGANISM: Artificial Sequence
<220> FEATURE:
<223> OTHER INFORMATION: From collagen I alpha chain.

<400> SEQUENCE: 66

Gly Pro Gln Gly Ile Trp Gly Gln
1               5

<210> SEQ ID NO 67
<211> LENGTH: 8
<212> TYPE: PRT
<213> ORGANISM: Artificial Sequence
<220> FEATURE:
<223> OTHER INFORMATION: From collagen I alpha chain

<400> SEQUENCE: 67

Gly Pro Gln Gly Ile Trp Gly Gln
1               5
```

```
<210> SEQ ID NO 68
<211> LENGTH: 6
<212> TYPE: PRT
<213> ORGANISM: Artificial Sequence
<220> FEATURE:
<223> OTHER INFORMATION: From fibrinogen

<400> SEQUENCE: 68

Leu Ile Lys Met Lys Pro
1               5
```